(12) United States Patent
Wenzl

(10) Patent No.: US 7,148,407 B2
(45) Date of Patent: Dec. 12, 2006

(54) FUNGAL BETA-GLUCURONIDASE GENES AND GENE PRODUCTS

(75) Inventor: Peter Wenzl, Canberra (AU)

(73) Assignee: Cambia, Act (AU)

( * ) Notice: Subject to any disclaimer, the term of this patent is extended or adjusted under 35 U.S.C. 154(b) by 38 days.

(21) Appl. No.: 10/757,093

(22) Filed: Jan. 14, 2004

(65) Prior Publication Data
US 2005/0153448 A1    Jul. 14, 2005

(51) Int. Cl.
*A01H 5/00* (2006.01)
*C12N 15/82* (2006.01)
*C12N 1/20* (2006.01)

(52) U.S. Cl. .................. 800/298; 435/70.1; 435/320.1; 435/419; 435/252.3; 536/23.74

(58) Field of Classification Search ............. 536/23.74; 800/278, 298; 435/69.1, 70.3, 71.1, 320.1, 435/252.1, 70.1, 419, 252.3
See application file for complete search history.

(56) References Cited

FOREIGN PATENT DOCUMENTS

WO      WO 00/55333      9/2000

OTHER PUBLICATIONS

Lazar et al., Transforming Growth Factor: Mutation of Aspartic Acid 47 and Leucine 48 Results in Different Biological Activities, Molecular and Cellular Biology, 8:1247-1252, 1988.*

Hill et al., Functional Analysis of Conserved Histidines in ADP-Glucose Pyrophosphorylase From *Escherichia coli*, Biochemical and Biophysical Research Communications, 244:573-577, 1998.*

Guo et al., Protein Tolerance to Random Amino Acid Change, PNAS., 101:9205-9210, 2004.*

Jefferson et al. "Beta-glucuronidase from *Escherichia coli* as a gene fusion marker." Proc. Natl. Acad. Sci. USA (Nov. 1986) vol. 83 pp. 8447-8451.

Kuroyama et al., "Purification and characterization of a beta-glucuronidase from *Aspergillus niger*." Carb. Res. (Jun. 22, 2001) vol. 333, No. 1, pp. 27-39.

Gallagher et al "The *Escherichia coli* gus operon: induction and expression of the gus operon in *E. coli* and the occurrence and use of GUS in other bacteria." Gus Protocols: Using the Gus gene as a reporter of gene expression. pp. 7-22, 1992.

Wenzl et al. "A Functional Screen Identifies Lateral Transfer of Beta-Glucuronidase (gus) from Bacteria to Fungi." Mol. Biol. Evol. vol. 22(2) pp. 306-316, 2005.

* cited by examiner

*Primary Examiner*—Elizabeth F. McElwain
(74) *Attorney, Agent, or Firm*—Cougar Patent Law; Carol Nottenburg

(57) ABSTRACT

Nucleic acid molecules encoding fungal β-glucuronidases are provided. Gene products, expression vectors and host cells suitable for expressing β-glucuronidase are also provided. In addition, uses of the β-glucuronidase as a visual and as a selectable marker for transformation are also described.

25 Claims, 31 Drawing Sheets

Socpulariopsis sp. isolate RP38.3

```
   1 GATATTGAGA GCACTTTTCT CTTGTATGTG GATGAGGAAG GGCGACGAAA TGAAAAAAAA AAAAAAAAAA
  71 AAAAGCCGGA GTTGACAAAC CCTGGCCTCG GCTTACCATA CACTAAAGTG ATAGATCTGG ATGTCACATT
                                                                        (dA)22
 141 ATACGTGACG ATCTCCGGGG TCTATTCCGC TGTTCATTAC CATTCAGTCG GAAAAGTCTG GTGCACTGGC
       (dA)8
 211 CTTGCGAACA AAAAAAATGC TGTCGTGTGT TACCCGACTA CCATGCTTCT ACTCATTTTT CGGCGATTTC
 281 GGAATCCAGT ATGCGGGGAC GGACTGTAAG TTGTAAGAAA GTTCTGACAA ATACAGAAAA TCCGGGGAGT
 351 GGAAGTTCAA TTGAATGTGG AGAAGAAATG CGAGTGTCCA GATGGGGAA TGCGGAGAC TCTTGTAGAC TCTGCAAAGA
 421 GCAGAAGTGC GGAAACACG GAGAGAGGA TAGGCGGAGAC TGCGGATAAG ACAAAGGGTA AGTGATCTTC
 491 GAGGTGTGTC TATTCGGGAA TAGTGTACAT CTCATAGGGA AACCACCGAG TCAAACCCAT
 561 GACTATATGA AGGAGCGACG ATCTCGAAAA AAAAAAGAGA AGAGCACACAA ACCTCCAGCC AGAGCAACCT
       TATAbox                        (dA)10      M  R  L  S  N  I  P  L  L  R  P
 631 GAGCCGTCAA CTCCCTGCTT GTCCATCATG CGCCTCTCTA CGCCTCTCTA ATATCCCCCT TCTGCGCCCT TGGGCCGCTC
      S  L  A  T  L  I  G  L  S  S   W  A  A  L
 701 TGTCCCTAGC CACCCTCATC GGCCTGTCCT CTGGGCCGA CACTGACCAA TGGAAGACGC TCAAGCCCCA
      A  N  A  I  R  E  L  L  S  L  D  G  T  W  N  F  A  L  P  Q  S  R  E
 771 AGCTAATGCT ATTCGGGAGC TACTCTCCCT TGATGGTACC TGGAACTTTG CCCTCCCGCA ATCACGCGAA
      I  E  E  D  Q  G  W  T  S  V  I  P  P  K  L  Q  I  P  V  P  A  S  Y  N
 841 ATTGAGGAAG ACCAGGGCTG GACTAGGGTT ATTCCACCCA AACTGCAAAT CCCAGTGCCC GCCAGCTACA
      D  I  F  T  D  P  A  I  R  N  N  V  G  W  A  Y  Y  Q  R  H  A  I  V
 911 ACGACATCTT CACCGATCCG GCGATCCGA ACAACGTTGG CTGGGCATAC TATCAGCGCC ACGCCATTGT
      P  Q  T  W  S  E  G  R  Y  Y  V  R  F  D  S  V  T  H  E  A  K  V  Y
 981 CCCCCAGACC TGGTCTGAGG GACGCTACTA TGTTCGCTTC GACTCTGTTA CGCACGAGGC CAAGGTCTAC
      V  N  D  E  E  V  G  G  H  V  G  G  Y  T  P  F  E  V  D  L  T  D  L  V
1051 GTCAACGACG AGGAAGTCGG AGGCCATGTC GGTGGATATA CTCCCTTCGA GGTTGACCTG ACCGACCTTG
```

FIG. 2A

| | | |
|---|---|---|
| | S P G E Q F R L T V A V N N I L T W Q T I P P | |
| 1121 | TGTCGCCGGG AGAGCAGTTC CGGCTGACTG TTGCTGTCAA CAATATCCTG ACTTGGCAGA CCATCCCCCC | |
| | G E V T N E A G K L R Q D Y N H D F Y N Y A | |
| 1191 | TGGTGAGGTC GTGACCAACG AGGCTGGTAA GCTTCGACAG GACTACAACC ACGACTTCTA CAACTACGCT | |
| | G I A R S V S L Y S V P D V H V S D V T V T T E | |
| 1261 | GGAATTGCAC GTTCGGTCTC GCTATACTCC GTGCCTGATG TTCATGTTAG CGAGGTCACT GTTACTACCG | |
| | N D D E G N E G T V N Y S V E T S G S N D T Q | |
| 1331 | AGAACGACGA CGAGGGCAAC GAGGGCACCG TCAACTACTC TGTCGAGACC AGCGGGTCTA ACGACACTCA | |
| | A R V T L I D E D G N E V A E A S E L E G S L | |
| 1401 | AGCTAGGGTC ACTTTGATTG ATGAGGACGG CAACGAGGTC GCCGAGGCAT CGGAGCTTGA GGGGAGCTTG | |
| | N V S P V N L W Q P G A A Y L Y T L R V E L L S | |
| 1471 | AACGTGAGCC CCGTGAATCT CTGGCAGCCG GGCGCGGCGT ACCTCTACAC TCTTCGCGT GAACTCCTTT | |
| | D D T V V D T Y D L P V G V R S V R V E G N Q | |
| 1541 | CGGACGATAC CGTCGTCGAC ACTTATGATT TACCGGTTGG TGTACGGTCC GTTAGGGTTG AAGGAAACCA | |
| | F L I N G K P F Y F T G F K H E D S P V R G | |
| 1611 | GTTCCTCATC AACGGCAAGC CCTTCTACTT CACCGGCTTT GGCAAGCACG AGGACAGCCC CGTCCGCGGA | |
| | K G Y D P A Y M I H D F E L M K W M G A N S F R | |
| 1681 | AAGGGCTACG ACCCGGCCTA CATGATCCAT GATTTTGAGC TCATGAAGTG GATGGGCGCC AACTCCTTCC | |
| | T S H Y P Y A E E V M E Y A D R H G I V V I D | |
| 1751 | GGACCTCCCA CTACCCCTAC GCCGAGGAGG TCATGGAGTA CGCCGACCGT CACGGCATCG TCGTCATCGA | |
| | E V A A V G L N L G I S A G L R G D E P P K T | |
| 1821 | CGAGGTCGCC GCCGTCGGTC TGAACCTGGG CATCAGCGCA GGCCTCAGGG GAGATGAGCC GCCCAAGACC | |
| | F T E D K V N N E T Q K T H A Q A L R E L I H R | |
| 1891 | TTCACGGAGG ACAAGGTTAA CAACGAGACG CAAAAGACAC ACGCCCAGGC CCTCCGTGAG TTGATCCACC | |
| | D K N H A S V V S W C V T N E P A S A E D G A | |
| 1961 | GTGACAAGAA CCACGCCTCC GTTGTCAGCT GGTGCGTCAC CAACGAGCCC GCCTCCGCCG AGGACGGTGC | |
| | R E Y F Q P L V E L T R E L D P T R P V T F T | |
| 2031 | CCGCGAGTAC TTCCAGCCCC TGGTCGAGCT TACCCGCGAG CTGGACCCCA CCCGCCCCGT CACCTTCACC | |
| | N V M G A T V D K C L I S D L F D F L S L N R Y | |
| 2101 | AACGTCATGG GGGCCACCGT CGACAAGTGC CTCATCTCCG ATCTTTTCGA CTTCCTTTCT CTCAACCGCT | |

FIG.2B

```
              Y  G  W  Y  V  Q   T  G  D  L   E  S  A  E   V  A  M  E   E  E  L  L   Q
2171       ACTACGGGTG GTACGTCCAA ACGGGCGACC TGGAGTCCGC CGAGGTCGCC ATGGAGGAGG AGCTCCTCCA
            W  V  D  E  Y  D  K   P  I  I  M   S  E  Y  G   A  D  T  L   A  G  L  H
2241       GTGGGTCGAC GAGTATGACA AGCCTATCAT CATGTCCGAG TACGGCGCCG ACACCCTGGC CGGTCTCCAC
            A  V  D  E  V  L  W   S  E  E  Y   Q  T  N  L   L  R  M  S   H  K  V  F  D
2311       GCGGTCGACG AGGTGCTCTG GTCCGAGGAG TACCAGACCA ACCTCCTGCG CATGTCGCAC AAGGTCTTTG
            S  I  D  S  I  V  G   E  H  V  W   N  F  A  D   F  Q  T  P   H  T  G  V
2381       ACAGCATTGA CTCCATTGTT GGCGAGCACG TGTGGAACTT TGCTGATTTC CAGACTCCTC ATACTGGTGT
            N  R  V  D  G  N  K   K  G  V  F   T  R  E  R   R  P  K  A   A  A  H  E
2451       CAACCGTGTT GATGGAAACA AGAAGGGTGT GTTTACGCGT GAGCGGAGGC CTAAGGCCGC GGCACATGAG
            L  K  R  R  W  L  D   E  G  F  P   K  L  G  N   G  T  S  G   A  *
2521       CTCAAGAGGC GGTGGCTGGA CGAGGGGTTC CCGAAGCTGG GGAACGGTAC TTCCGGTGCT TAAGTGGAGC
2591       ACGGGTATGA TAGGGTTTAA CTGCAAGCTA GAGGTTTTAG TGACATACAC CTGTTGAGAT CTGTTGAGAT
2661       CTGGAATTTA CGCCGTATGA ATTGCTTATG GACTTTATGC CAAGGACTTG TTGCCATCT AATACTTTGT
2731       AGAAAGCTAG TCGCTGCCGT GATTGCGAAG GGGCTTTAA GTCACCCAAC CTGGATCAAA GACATTATTC
2801       CACTATATCA CAACTTCATG AGTACGAGTG GGGATTGAAA GCAAACGGTC GCGGACTCTA CTCGGCAGCC
2871       GCGACTTCGG GCCAAGTTTG AGAAAAGGGC CATGTTATGATT CGGAAGTCTA TACATTAATA
2941       CAAGGTGCCC TGCTCTGTTA AACCCCTCT CACTCGCTTT TTAAAGACGC ACAGGGCCAT TTTGTGCCCT
                         Poly(dA) signal    Poly(dA) site
3011       TAACTCTGAA GACGTTGTTA GAATAAAAGT GGTGGAGCCA GCTGCCTACG CCTAGTTGGC CAGTTCTCCA
3081       GTCTCCACT TGCAAGCTAA TCCTGAGGAA AAGCTTGACG CGGTGAAACG CCGTTCCGTT CTGCGTGAGG
3151       TTTAGTATCC TAACTAAGCA CGTACGGTAA AATCTCGGCC GTGCCGTGCC ACCTTGTTTG GATCGTCACG
3221       AACTCGTAAA ATCCCGCACT TGATTTTACT TAAAACGAGA CCTTTTTACAT TCTGGAGTTG ATACCCCGGC
3291       GTATCCGCCA ACGTCGTNCN AGGTCGTTAC CCCTCATACA GGGCCGTTAC AAGCC
```

FIG.2C

Penicillium canescens isolate RPK

```
  1  GCCAAGCTCA TCAGTCACCG ATGAAAAACT ACTCAATTGC CGATGCATCG TCTGGAAAAC TATATAAATG
                                                     TATA box        TATA box
 71  CCTAAGTGCA GCCAGATATA ATACCCTCAT CAACTTATAC TAATTCATTA AATAAACAGT GGCTTTGTTA
                           ATACCCTT  AATAAAGCGG CAATGAAATT CCTTACGGGA TTGTCGCTGC TGTCCTCTTGC TGGTCCATCG
                              ───────►  M  K  F   N  E  M   T  Q  H   V  L  L    L  S  L   A  G  P  S
141  AATAAAGCGG CAATGAAATT CCTTACGGGA TTGTCGCTGC TGTCCTCTTGC TGGTCCATCG
        L  G  T  P    A  A  R    H  F  P   R  N  E  M    T  Q  H    V  L  L    L  S  L   A  G  P  S
211  TTGGGTACAC CTGCAGCTCG GCACTTTCCA CGCAATGAAA TGAACAGCCC TTGATCAAAG
        T  G  Y  T    C  S  S   S  H  F  P    R  N  E   M    N  S  P   L  I  K  V
211  TTGGGTACAC CTGCAGCTCG GCACTTTCCA CGCAATGAAA TGAACAGCCC TTGATCAAAG
         R  P  Q    R  T  S   S  R  E  L   V  N  L   D  G  L    W  K  F   A  L  A  S
281  TCAGGCCCCA ACGAACTTCA TCTCGAGAGC TTGTGAACCT TGATGGTCTA TGGAAATTCG CCCTCGCATC
         R  P  Q    R  T  S   S  R  E  L   V  N  L   D  G  L    W  K  F   A  L  A  S
351  TGGCCTCAAT GACACGGCCC AACCGTGGAC AGCGCCATTA CCCAAAGGTC TTGAATGTCC AGTCCCGGCC
         G  L  N   D  T  A  Q    P  W  T    A  P  L  P    K  G  L    E  C  P   V  P  A
421  TCTTACAACG ACATCTTCAT CAGGCGGGAG ATTCACGACC ATGTGGGATG GGTTTACTAT CAGGTGAGG
         S  Y  N   D    I  F   I  S  R  E    I  H  D  H    V  G  W    V  Y  Y   Q  R  E  V
491  TCATTGTCCC CAAAGGCTGG TCTCAGGAGC GATATCTCGT GGCGAGCCGAA TCCGCTACGC ACCATGGTCG
        I  V  P    K  G  W    S  Q  E  R   Y  L  V    R  A  E   S  A  T  H    H  G  R
561  CATCTATGTC AACAACCGGC TTGTGCCGA GCATGTGGGC NGCTATACAC CTTTTGAAGC GGACGTCACT
         I  Y  V  N   N  R  L    V  A  E   H  V  G  X    Y  T  P    F  E  A   D  V  T
631  GAATTAGTCG CCCCCGGAGA GAAATTTCGC TTGACGATTG GTGTCAACAA CGAGCTTACC CATGAGACTA
         E  L  V  A    P  G  E    K  F  R   L  T  I  G    V  N  N   E  L  T    H  E  T  I
701  TCCCCACCTGG AAAAATCACG ACAGGGAACG CGACTGGCAA GAGAATCCAG ACCTATCAAC ATGACTTTA
         P  P  G    K  I  T  T    G  N  A    T  G  K   R  I  Q    T  Y  Q  H   D  F  Y
771  CAACTATGCT GGTCTCGCCC GATCTATCTG GCTTTATTCT GTACCCCAGC AACATATCCA GGATATTACT
         N  Y  A    G  L  A  R    S  I  W    L  Y  S   V  P  Q  Q    H  I  Q  D    I  T
841  GTGGTTACAG ATGTTGATGG TGACAACGGT CTGATTAACT ACGAGGTCGA AGTGGCGAAC AGAGGACGG
         V  V  T  D    V  D  G    D  N  G   L  I  N  Y    E  V  E   V  A  N    Q  T  T  G
```

```
         I   R   V   D   G   N   K   K   G   V   F   T   R   D   R   K   P   K   A   A   A   H   S
1961 TCATCCGAGT AGAGGGTAAC AAGAAGGGTG TTTCACCCG TGACCGAAAG CCAAAGGCGG CAGCTCATAG
     L   R   A   R   W   T   S   I   D   K   N   *
2031 TTTGAGGGCA AGGTGGACTA GTATTGATAA GAATTAAGGA ATTGACATAC AAATGTTTGG
2101 CCTCACATTA CAAAACTATA TGCAATTAAA TGTACTGAAG ATTCGAGGGG TCGACCACTG ACAATGGAAC
2171 AAATGTGCT TAACAGACGT AAGTCTGGAT TCTACTTGAA CAGAGGTAAG TCTGGATTCT ACTTGATTGG
2241 ACTGCTTGTC ATATGTTCCA AATCGTATCG TAAACATTAT TGAAAATGGC CAGGAGACAG CGTGGAAAGA
2311 AAGGACAACA GTCTGGAAGA CAAGTTCGGA TGCGCGGATT CCCTGAAGCT CCCCCTTGCAA AACTCATTAC
2381 TGGGCCCCTC CATACAACAT TAAGGCTAT CATGATCTTC TCTACAAAGG GCCTCTGCCC AGGTGGACTG
                                                                      Poly(dA) signal
2451 CCTTCTCTGA GGATGTGGAG CGGGTCTACT TCCATCAAGT CCTCATCAAT AGAGCTATAT ACGATATTGG
          Poly(dA) site
2521 ACGAGCGGCA GAAGGCAACG AGACAATCAA CGAGTTCGTG GCTGTAGTCC AAGAGTCTGT CGGCGTTCAG
2591 AGCTGTTTCA TGCACTCAAT CGGAACGG
```

FIG.3C

*Penicillium canescens* strain DSM1215

MetLysPheLeuThrArgLeuSerLeuLeuSerLeuAlaAlaPro
ATGAAATTTCTTACGCGATTGTCGCTGCTATCTCTTGCTGCTCCA

SerLeuGlyThrProAlaAlaArgHisPheProArgAsnGluMet
TCGTTGGGTACACCTGCAGCTCGGCACTTTCCACGCAATGAAATG

XaaGlnAsnGleGlnProLeuIleLysIleArgProGlnArgThr
ATCCAAAATGAACAGCCCTTGATCAAAATCAGGCCCCAACGAACT

SerSerArgAspLeuValAsnLeuAspGlyLeuTrpLysPheAla
TCATCTCGAGACCTTGTGAACCTTGATGGTCTATGGAAATTCGCC

LeuAlaSerGlyProAsnAspThrAlaGlnProTrpThrAlaPro
CTCGCATCTGGCCCCAATGACACGGCCCAGCCGTGGACAGCGCCA

LeuProLysGlyLeuGluCysProValProAlaSerTyrAsnAsp
TTACCCAAAGGTCTTGAATGTCCAGTCCCGGCCTCTTACAATGAC

IlePheIleSerArgGluIleHisAspHisValGlyTrpValTyr
ATTTTCATCAGCCGGGAGATCCACGACCATGTGGGATGGGTTTAC

TyrGlnArgGluValIleValProLysGlyTrpSerGlnGluArg
TATCAGCGTGAGGTCATTGTCCCCAAAGGCTGGTCTCAGGAGCGA

TyrLeuValArgAlaGluSerAlaThrHisHisGlyArgIleTyr
TATCTTGTGCGAGCCGAATCCGCTACACACCATGGTCGCATCTAT

ValAsnAsnArgLeuValAlaGluHisValGlyGlyTyrThrPro
GTCAACAACCGGCTTGTTGCGGAGCATGTGGGCGGCTATACACCT

PheGluAlaAspIleThrAspLeuValValProGlyGluLysPhe
TTTGAAGCCGACATCACTGATTTGGTCGTCCCTGGAGAGAAATTT

ArgLeuThrIleGlyValAsnAsnGluLeuThrHisGluThrIle
CGTTTGACGATTGGTGTCAACAACGAGCTTACCCATGAGACTATC

ProProGlyGluIleThrThrAlaAsnAlaThrGlyLysArgIle
CCACCAGGAGAAATCACAACAGCGAACGCGACTGGCAAGAGAATC

GlnThrTyrGlnHisAspPheTyrAsnTyrAlaGlyLeuAlaArg
CAGACCTATCAACATGACTTTTACAACTATGCCGGTCTCGCCCGA

SerIleTrpLeuTyrSerValProGlnGlnHisIleGlnAspIle
TCTATCTGGCTTTATTCTGTACCCCAGCAACATATCCAGGATATT

FIG.4A

```
ThrValValThrAspValAspGlyAspAsnGlyLeuIleAsnTyr
ACTGTGGTTACAGATGTTGATGGTGACAATGGTCTGATCAACTAC

GluValGluValAlaAsnGlnThrThrGlyGlnIleGlnIleSer
GAGGTCGAAGTGGCGAACCAGACGACGGGGCAGATCCAGATCTCA

ValIleAspGluAspGlyAlaIleValAlaAsnAlaSerGlyAla
GTGATCGACGAGGATGGAGCTATTGTTGCAAATGCCTCGGGAGCT

GlnGlyThrValThrIleProSerValLysLeuTrpGlnProGly
CAGGGTACTGTCACAATTCCCTCAGTCAAGCTATGGCAACCTGGC

AlaAlaTyrLeuTyrGlnLeuGlnValAsnValValAspSerSer
GCCGCATATCTCTACCAACTCCAGGTCAACGTCGTGGATTCTAGC

GlyAspValValAspThrTyrAsnLeuAlaThrGlyValArgThr
GGCGATGTAGTCGACACCTATAATTTGGCTACGGGCGTGCGTACT

ValLysIleSerGlySerGlnPheLeuIleAsnGlyLysProPhe
GTCAAGATTTCCGGGTCACAATTCTTGATAAACGGCAAGCCTTTC

TyrPheThrGlyPheGlyArgHisGluAspThrAlaValArgGly
TACTTTACCGGTTTTGGCAGGCATGAAGACACAGCAGTACGTGGC

LysGlyHisAspProAlaTyrMetValHisAspPheGlnLeuMet
AAAGGACATGACCCAGCATATATGGTTCACGATTTCCAACTCATG

LysTrpIleGlyAlaAsnSerPheArgThrSerHisXaaProTyr
AAATGGATTGGAGCAAATTCTTTCCGGACTTCACACTACCCTTAT

AlaGluGluValMetAspPheAlaAspArgAsnGlyIleValVal
GCAGAAGAGGTCATGGATTTCGCAGATCGAAATGGAATTGTCGTG

IleAspGluThrProAlaValGlyLeuAsnIleAlaLeuMetGly
ATCGATGAAACTCCTGCCGTGGGTCTGAACATTGCCTTGATGGGT

ValSerGluSerGlyAlaProGlnThrPheThrProAspGlyIle
GTATCTGAGAGTGGTGCCCCACAAACATTTACGCCAGATGGGATT

AsnAspLysThrGlnGluAlaHisLysGlnAlaIleArgGluLeu
AACGATAAGACCCAAGAGGCCCACAAACAGGCGATTCGTGAGCTC

IleAlaArgAspLysAsnHisAlaSerValValMetTrpSerIle
ATTGCCCGAGACAAAAACCATGCCAGTGTTGTCATGTGGTCTATT
```

FIG.4B

```
AlaAsnGluProAlaSerGlnGluAspGlyAlaArgGluTyrPhe
GCCAATGAGCCTGCATCTCAGGAAGATGGGGCTCGCGAATACTTC

GluProLeuAlaAsnLeuThrArgGlnLeuAspProThrArgPro
GAGCCACTGGCCAATTTGACTCGTCAGCTTGATCCAACTCGCCCT

IleThrPheAlaAsnValGlyAlaAlaThrTyrGlnLeuAspArg
ATTACATTTGCTAATGTCGGCGCTGCAACATATCAGCTAGATCGG

IleSerAspLeuPheAspValSerCysIleAsnArgTyrPheGly
ATCTCTGATCTGTTTGATGTTAGTTGCATAAATCGGTATTTCGGA

TrpTyrSerGlnThrGlyAspLeuGluGluAlaGluAlaAlaLeu
TGGTATTCTCAGACAGGAGACCTTGAGGAAGCAGAGGCAGCTCTT

GluLysGluLeuArgGlyTrpGlnGluLysPheHisArgProIle
GAAAAGGAGTTGCGTGGGTGGCAAGAGAAATTCCACAGGCCGATC

IleMetSerGluTyrGlyAlaAspThrLeuAlaGlyLeuHisSer
ATTATGAGCGAATATGGTGCAGATACCCTTGCAGGTCTTCATTCT

IleLeuAlaLeuProTrpSerGluGluPheGlnValGlnMetLeu
ATCCTCGCACTGCCTTGGAGCGAAGAGTTCCAGGTACAAATGCTA

AspMetTyrHisArgValPheAspArgIleGluSerMetAlaGly
GACATGTACCATCGAGTGTTTGATCGCATTGAGTCGATGGCAGGC

GluHisValTrpAsnPheAlaAspPheGlnThrAsnLeuGlyVal
GAGCATGTTTGGAACTTCGCGGATTTCCAGACCAACTTGGGTGTC

IleArgValAspGlyAsnLysLysGlyValPheThrArgAspArg
ATCCGAGTAGATGGTAACAAGAAGGGTGTTTTCACGCGTGACCGA

LysProLysAlaAlaAlaHisSerLeuArgAlaArgTrpThrAsn
AAGCCAAAGGCGGCAGCTCATAGTTTGAGGGCAAGGTGGACGAAT

GlyAspLysAsn
GGTGATAAGAATTAG
```

FIG.4C

*Giberella zeae*

```
ATGTTGCGACCACAAGCCAACAGGGCTCGCGACCTTGTGTCACTAGACGGTGTTTGGAACTTTGCCCTCGCCA
AATCTCACGACATTGAAACTGAGCAAGCATGGAAGAAGCGAATCTCACCAGAGCTTCAAGTACCTGTTCCAGC
CAGCTACAACGACATCTTTGCTGACGAGACCATCCGCGACCACGTCGGCTGGGTCTACTATCAGCGTCAAGCA
GTTGTTCCCCGCGGTTGGGTTGCGCCTCAGCGTGTCTTTCTACGTGTAGATGCTGCAACCCACCACGGCAGAG
TTTACGTCAACGACAAGTTTGTCGTCGAGCATATCGGCGGCTATACACCGTTTGAGATTGAGCTTACTGGACT
TGTCGAACCGGGGTCAGAGTTTCGTCTTACGATTGCTGTGAACAATCAACTCACATGGGAGACTATTCCGCCG
GGTCGCATTGAGGCTCAAAGTGATGGTTCGCGGAAGCAGAGCTATCAGCATGACTTTTTCAACTATGCTGGAT
TGGCCCGTTCTGTGTGGCTTTACTCGGTACCAAAGGTCTTTATAAATGATATCAGCGTCGGCACAGATCTTCT
TGGGGACGGAACCGGCATTGTCGAATTTGATATTCGGACCTCTGGTGAACTTCAGGCTGACGCAAGATGGCGC
ATCCTGCTCGACGACGAAGAGGATGCGACAGTGTGTCAAGCCCAAGAGTCACATGGAAAACTTGAGGTTAAAA
ACGCTAAATACTGGGCACCTGGTGCTGCGTACCTTTATCAGCTTCGGGCTCAGCTCGTACGCGGCGAACACGA
CGAGATCCTCGACACATATAACCTTGCCGTAGGCATCCGTTCAGTCGAGATCCGAGATGGCCGCTTCTTCATC
AACGGGAAGCCATTTTATTTTACCGGCTTTGGCAAACACGAAGATGGCCCCGTCCGTGGACGCGGTTATGACG
CGTCATACATGATACACGACTACCGTCTGATGAAGTGGATAGGAGCCAACTCTTTCCGAACCTCCCACTACCC
CTACGCAGAGGAGGTTCTGGAATATGCCGACAGACACGGCGTGGTTGTTATTAACGAAACAGCCGCCGTTGGT
CTCAACCTCAATATTGTCTCGGGTATGTTTGGCAACAAGCAACTTGCCACATTCTCCCCGGATACCATGAGTA
GCAAAACACAGGCTTCACATGAACAAGCTATCCGTGAGCTTATCAGCCGGGATAAGAACCACCCTTGTGTTGT
GATGTGGATGCTGGCAAATGAGCCTGGGGCCAGCGAGCAGGGAAGTCGAGAATACTTTGAACCGCTCGTTACC
TTGGCGCGATCGCTGGACAGTCAGAAACGGCCAATGTGCTACTCCCACATGATCCACTCTAAGCCTGATACAG
ATCGCATCGCAGACCTTTTTGATGTAGTCTGTATGAACCGCTACTACGGGTGGTACACGCAAACAGGAAACCT
CAAAGCCGCAGAAGTCGCCCTTGAAGCCGAGCTACGCAGTTGGCAAGAAGCCTACGCCGCCAAACCCATAATC
ATGACGGAATATGGCACCGACACAGTCGCAGGTCTGCACACCGTTTGTGATGTGCCCTGGACTGAAGAGTACC
AGGTTCGCTTTTTGGACATGTATCACCGCGTCTTTGACCGCATTGATAATGTCGTCGGCGAGCATGTGTGGAA
CTTTGCTGATTTCCAGACATCGGCTATGATTATTAGGGTTGATGGGAACAAGAAGGGTATCTTTACTAGGGAT
CGCAGGCCAAAGAGTGCAGCTCATGCTTTGCGAGCGAGATGGACTGGGCCTGTTGGACCTCGCAAGATAGAGG
TGACCAAGCAATAA
```

```
MLRPQANRARDLVSLDGVWNFALAKSHDIETEQAWKKRISPELQVPVPASYNDIFADETIRDHVGWVYYQRQA
VVPRGWVAPQRVFLRVDAATHHGRVYVNDKFVVEHIGGYTPFEIELTGLVEPGSEFRLTIAVNNQLTWETIPP
GRIEAQSDGSRKQSYQHDFFNYAGLARSVWLYSVPKVFINDISVGTDLLGDGTGIVEFDIRTSGELQADARWR
ILLDDEEDATVCQAQESHGKLEVKNAKYWAPGAAYLYQLRAQLVRGEHDEILDTYNLAVGIRSVEIRDGRFFI
NGKPFYFTGFGKHEDGPVRGRGYDASYMIHDYRLMKWIGANSFRTSHYPYAEEVLEYADRHGVVVINETAAVG
LNLNIVSGMFGNKQLATFSPDTMSSKTQASHEQAIRELISRDKNHPCVVMWMLANEPGASEQGSREYFEPLVT
LARSLDSQKRPMCYSHMIHSKPDTDRIADLFDVVCMNRYYGWYTQTGNLKAAEVALEAELRSWQEAYAAKPII
MTEYGTDTVAGLHTVCDVPWTEEYQVRFLDMYHRVFDRIDNVVGEHVWNFADFQTSAMIIRVDGNKKGIFTRD
RRPKSAAHALRARWTGPVGPRKIEVTKQ
```

FIG.5

*Aspergillus nidulans*

```
ATGAGGGTCTTCCCAGTGTTATCTTTCTTGTCACTCGCACTCATCCCTCCCTCGCTCGGCGTCCCGTCGCCTC
AGCTCCGCGACGTCGAGCTCCCGCCAACACAACAAGCCCTAACCATCAACCTGAAACCCCAGCAGACGTCGAC
GAGAGACCTCGTTTCTCTCGACGGGCTGTGGTCCTTTGCCCTCGAAGACGCCACAAACAGCACCTCTGCTCCC
TGGACGGCGGCGCTCCCAAAGGGCCTGGAATGTCCCGTCCCTGCATCCTACAACGACATCTTCGTCGACAGGA
CCATTCACGATCACGTCGGCTGGGTATACTACCAACGCACTGTGACTGTCCCACGGGGCTGGGCAGATCAGCG
CGCTTTCCTCCGTCTGGAGTCAGCAACGCATCATGGCCGCGTCTATGTCAATGAGCACCTGGTTGCCGAGCAT
GTTGGCGGTTACACCCCGTTTGAAGCCGACATTACCTCTCTCGTGCAGCCTGGTGAAAGCTTCCGGTTGACAA
TCGGTGTGGACAACCAGCTGACGCACGAGACCATCCCTCCAGGTGATCTGGTGACTTCTGAGTATACAGGGAA
GAAACAGCAGAGCTACCAGCACGACTTTTACAATTACGCAGGGCTGGCGAGGTCCATATGGCTCTACTCTGTG
CCCAAGGATCAGTTCATCAAGGACATCACGGTCGTTCCAGATGTTGATTGGGATGGTGACGCAGAGACCGGAG
TGGTGAGCTATACCGTCCAGACTTCTAACGCGACGAGTGGCCCCATCCGGATCTCAATTCTCGATGAAGAAGG
AAACGAGGTCGCAACAGCGTCCGGAGCCACTGGGACAGCTACCATTCCCTCTGTCAACCTCTGGCAGCCTGGC
GCTCCCTACCTATACTCCTTCACTGTCAGCATCCTCTCCGCCTCCCAACGGCTGATCGACACATACACACTGC
CCATCGGTATCCGCACTGTGGCTGTCGGCAACGGCACTATCCTGGTCAACAATGAGCCGGTCTACCTGACCGG
GTTTGGCAAACACGAGGATAGTCCCATCCGCGGCAAAGGCCACGACATCGCGTACCTAGTCCACGACTTCCAG
CTGCTGGACTGGATCGGCGCGAACTCTTTCCGCACCAGCCACTATCCTTACGCGGAAGAGGTGATGGAATTTG
CAGACCGCCAGGGAATTCTTGTCATTGACGAAACGCCCGCCGTCGGACTGGCGTACAGCATTGGCGCGGGCAT
CTCAACGGACACAAGCAGGGTGACCTTCGCGCCGGACGGGATCAACAACAATACTCGCGCAGCCCACGCCCAG
GCTCTCCGGGAACTCATTGCACGGGACAAGAACCACCCCAGCGTTATCATGTGGTCGATCGCGAACGAACCCG
CGTCTGATGAGCCAGGTGCGCGCGCATACTTTGAGCCCCTCACGCGGCTCGCCCGCTCCCTCGATCCCGCGCA
CCGGCCCATAACTTTCGCCAACCTCGGCCTGGCAACCTATGAAACCGACACAATCTCTGACTTGTTCGATGTT
CTCTGCCTGAACCGATATTTCGGCTGGTACTCGTACACGGGAGACCTGGAGTCCGCCGGAAAGGCACTCCATG
AGGAACTGGACGGATGGGTGGCCAAGTACCCGACCAAACCAATCATCATCAGCGAGTACGGGGCAGACACAAT
GGCGGGACTGCACTCTGTGCTGGGACTGATCTGGAGCGAGGAGTTCCAAATCGAGTTGCTGGATGTGTATCAT
GGGGTGTTCGACCAGTTCCAGAATGTGGTTGGTGAGCATGTATGGAATTTCGCGGATTTCCAAACAAAGGAGG
GCATACAGCGGGTGGATGGGAACAAGAAGGGTGTCTTTACCAGAGACCGCAGACCCAAGGGGGCGGCGTTTGC
CTTGAGGAAGAGGTGGATGAATATGATGTCGAGTTAG
```

```
MRVFPVLSFLSLALIPPSLGVPSPQLRDVELPPTQQALTINLKPQQTSTRDLVSLDGLWSFALEDATNSTSAP
WTAALPKGLECPVPASYNDIFVDRTIHDHVGWVYYQRTVTVPRGWADQRAFLRLESATHHGRVYVNEHLVAEH
VGGYTPFEADITSLVQPGESFRLTIGVDNQLTHETIPPGDLVTSEYTGKKQQSYQHDFYNYAGLARSIWLYSV
PKDQFIKDITVVPDVDWDGDAETGVVSYTVQTSNATSGPIRISILDEEGNEVATASGATGTATIPSVNLWQPG
APYLYSFTVSILSASQRLIDTYTLPIGIRTVAVGNGTILVNNEPVYLTGFGKHEDSPIRGKGHDIAYLVHDFQ
LLDWIGANSFRTSHYPYAEEVMEFADRQGILVIDETPAVGLAYSIGAGISTDTSRVTFAPDGINNNTRAAHAQ
ALRELIARDKNHPSVIMWSIANEPASDEPGARAYFEPLTRLARSLDPAHRPITFANLGLATYETDTISDLFDV
LCLNRYFGWYSYTGDLESAGKALHEELDGWVAKYPTKPIIISEYGADTMAGLHSVLGLIWSEEFQIELLDVYH
GVFDQFQNVVGEHVWNFADFQTKEGIQRVDGNKKGVFTRDRRPKGAAFALRKRWMNMMSS
```

FIG. 6

| Organism | Sequence |
|---|---|
| Caenorhabditis elegans | (1) ----------------------------------MILKPTVLLLLLQSISTITCLH |
| Drosophila melanogaster | (1) MHLRIRLTCRKYEIWALSIFSLVTGLYVLHFSIALILVNKEVPQTRGMLY |
| Mus musculus | (1) --------------------------------MSLKWSACWVALGQLLCSCALALKGGMLF |
| Rattus norvegicus | (1) --------------------------------MSPRRSVCWFVLGQLLCSCAVALQGGMLF |
| Felis catus | (1) --------------------------------MLRGPAAVWAALGPLLWACGLALRGGMLY |
| Canis familiaris | (1) --------------------------------MSRGPAGAWVALGPLLWTCGLALEGGMLY |
| Cercopithecus aethiops | (1) ------------------------------------GLAMAWAVLGPLLWGCALALQGGMLY |
| Homo sapiens | (1) --------------------------------MARGSAVAWAALGPLLWGCALGLQGGMLY |
| Sulfolobus solfataricus | (-) ------------------------------------------------ |
| Thermotoga maritima | (1) ------------------------------------------------MVR |
| Lactobacillus gasseri | (1) --------------------------------------------MESALY |
| Escherichia coli | (1) ------------------------------------------------MLR |
| Staphylococcus sp. | (1) ------------------------------------------------MLY |
| Aspergillus nidulans | (1) -----MRVFPVLSFLSLALIPPSLGVPSPQLRDVELPPTQQALTINLK |
| Penicillium canescens | (1) -----MKFLTGLSLLSLAA--PSLGTPAARHFPRNEMTQHEQPLIKVR |
| Scopulariopsis sp. | (1) ------------------------------------------------ |
| Gibberella zeae | (1) ---------------------MRLSNIPLLRPWAALSLATLIGLS-SGADTDQWKTLK |
| Consensus |     L              L                           MLY |

FIG. 7A

| Organism | Sequence |
|---|---|
| Caenorhabditis elegans | (25) VQKNEIRTVDSLDGLWTFVREPHNGGDVGIIVNQWNTLDLERFQNATVMPV |
| Drosophila melanogaster | (51) PRESETREVRSLDGIWNFVRSDQANPTQGVRDEWYAKELSKSRPTIPMPV |
| Mus musculus | (30) PKESPSRELKADGLMHFRADLSNNRLQGFEQQWYRQPLRESGPVLDMPV |
| Rattus norvegicus | (30) PKETPSRELKVLDGLMSFRADYSNNRLQGFEKQWYRQPLRESGPTLDMPV |
| Felis catus | (30) PRESPSRERKELNGLMSFRADFSENRRGFEQQWYRTPLRESGPTLDMPV |
| Canis familiaris | (30) PRESPSRERKDLDGLMSFRADFSDGRRGFEQQWYRAPLRESGPTLDMPV |
| Cercopithecus aethiops | (27) PRESQSRERKELDGLMSFRADFSDNRRRGFEEQWYRRPLRESGPTLDMPV |
| Homo sapiens | (30) PQESPSRECKELDGLMSFRADFSDNRRRGFEEQWYRRPLWESGPTVDMPV |
| Sulfolobus solfataricus | (1) -MRSFYRPKIDLQGFMKFKIDNEN---TGEENGWYKGLESED----IIYV |
| Thermotoga maritima | (4) PQRNKKRFILILNEVMNLEVTSK---------DR--P----IAV |
| Lactobacillus gasseri | (7) PIQNKYRFNTLMNGTWQFETDPN----SVGLDEGWNKEPDP---EEMPV |
| Escherichia coli | (4) PVETPTREIKKLDGLWAFSLDREN--QIDQRMWESALQES---RAIAV |
| Staphylococcus sp. | (4) PINTETRGVFDLNGVWNFKLDYG-----KGIEKWYESKLTDT---ISMAV |
| Aspergillus nidulans | (44) PQQTSTRDLVSLDGLMSFALEDA----TNSTSAPWTAALPKG---LECPV |
| Penicillium canescens | (42) PQRTSSRELVNLDGLMWKFALASG----LNDTAQPWTAPLPKG---LECPV |
| Scopulariopsis sp. | (37) PQANAIRELSSLDGTWNFALPQSR---EIEDQGWTSVIPPK---LQIPV |
| Gibberella zeae | (4) PQANRARDLVSLDGVWNFALAKSH---DIETEQAWKKRISPE---LQVPV |
| Consensus | P S SREL LDGLW F D S G E QWY L ES LDMPV |

FIG.7B

| | | |
|---|---|---|
| Caenorhabditis elegans | (75) | PSAYND LGTGSEL RDHIG WVW YEKKEF VPL RDRNMR---HVLRFGSVNYF |
| Drosophila melanogaster | (101) | PASYND ITTDN-LRDH VGTIV WYDRKF FVP RSWSKDQ--RIWLRFGSVHYE |
| Mus musculus | (80) | PSSFND ITQEAALRDFIG VVW YEREAIL PRR WTQDTDMR WLRINSAHYY |
| Rattus norvegicus | (80) | PSSFND ITQEAALRDFIG VVW YEREAVL PQR WTQDTDRR WLRINSAHYY |
| Felis catus | (80) | PSSFND VGQDRQLRSFVG WVW YEREATL PQR WTQDLGTR WLRIGSAHYY |
| Canis familiaris | (80) | PSSFND VGQDRQLRSFVG WVW YEREATL PRR WSQDPGTR WLRIGSAHYY |
| Cercopithecus aethiops | (77) | PSSFND ISQDWRLRHFVG WVW YEREVIL PER WTQDLSTR WLRIGSAHAY |
| Homo sapiens | (80) | PSSFND ISQDWRLRHFVG WVW YEREVIL PER WTQDLRTR WLRIGSAHSY |
| Sulfolobus solfataricus | (43) | PASWNEQNPKWD--QFSGIA WYQKDLF VSNDNGNRK---AWMVFEGAGYI |
| Thermotoga maritima | (33) | PGSWNEQYQDL--CYEEGPFT VY QKOFF IPSFLKKE---IRLYFAAVNTD |
| Escherichia coli | (50) | PGTFAELTTKRDRKYYTG DFW YQREVF IPK WAG-QR--LYIRFGSVTHR |
| Staphylococcus sp. | (48) | PSSFND QFADADIR NYAG NMW YQREFT VRAYLKDQR---IVLRFDAVTHY |
| Aspergillus nidulans | (47) | PSSYND IGVTKEIR NHIG YVW YYYQRT VTVPRG WAD-QR--AFLRLESATHK |
| Penicillium canescens | (87) | PASYND IFV QRTIHDH VGW VYY QREV IVPKG WSQ-ER--YLVRAESATHH |
| Scopulariopsis sp. | (85) | PASYND IFISREIHDH VGW VYY QRE IVPKG WSQ-ER--YLVRAESATHH |
| Gibberella zeae | (81) | PASYND IFT DPAIR NNVG WAYY QRH AIV PQT WSE-GR--YYVRFDSVTHE |
| | (48) | PASYND IFADETIRDH VGW VYY QQA VVPRG WAPQR--VFLRVDAATHH |
| Consensus | (101) | PSSFNDI  D  LR FVGWVWYERE   VP  WSQ     VVLR GSA HY |

FIG. 7C

| | | |
|---|---|---|
| Caenorhabditis elegans | (122) | AVVYISEKMTSHLGGHLPFEMDJSAQIKFGAENK---FTMAVNNTLSWS |
| Drosophila melanogaster | (148) | AYVWLGQKMVKHEMGHLPFEAEVTDLSYGAENR----ITMCDMALIQT |
| Mus musculus | (130) | AVVWVGIHMVEHEGGHLPFEADISKLVQSGPLTT-CRITIAINNTLTPI- |
| Rattus norvegicus | (130) | AVVWVGIHMVEHEGGHLPFEADISKLVQSGPLTT-FRVTIAINNTLTPY |
| Felis catus | (130) | AIVWVGVHMAEHEGGHLPFEADISKLVQSGPLAS-CRITIAINNTLTPI- |
| Canis familiaris | (130) | AIVWVGVHMAEHEGGHLPFEADISKLVQSGPLSS-CRITIAINNTLTPI- |
| Cercopithecus aethiops | (127) | AIVWVGVHTLEHEGGYLPFEADISNLVQVGPLSSHVRITIAINNTLTPI- |
| Homo sapiens | (130) | AIVWVGVDTLEHEGGYLPFEADISNLVQVGPLPSRLRITIAINNTLJPT |
| Sulfolobus solfataricus | (88) | TKLMIGEYGGTHEGSFTQLKFPIKLKVNEFNKIV-----VKIDNTPSPY |
| Thermotoga maritima | (78) | CEVFLNGEKVGENHIEYLPFEMDVTGKMKSGENELR----VVVENRKVG |
| Lactobacillus gasseri | (97) | AKVFINGHEHVGQHEGGFLPLQVKISNYINYDQTNR---VTMLVNNELSEK |
| Escherichia coli | (95) | GKVWVINQEMVEHQGGYTPEADVTPYMIAGKSVR----ITMCVNNELNWC |
| Staphylococcus sp. | (94) | AIVMVNGELVMEHKGGFLPFEAETNNSLRDGMNRV----TMAVDNILDDS |
| Aspergillus nidulans | (134) | GRMYMNEHLVAEHMGGYTPFEADITSLVQPGESFR----LTIGVDNQLTHE |
| Penicillium canescens | (132) | GRIYMNNRLVAEHMGGYTPFEADVTELVAPGEKFR----LTIGVNNELTHE |
| Scopulariopsis sp. | (128) | AKVYMADEEVGGHMGGYTPFEMDLTDLVSPGEQFR----LTMAVNNILTWC |
| Gibberella zeae | (96) | GRMYMDKFLVEHIGGYTPFEIELTGLVEPGSEFR----LTIAVNNQLIWE |
| Consensus | (151) | A VWVNG V EHEGGYLPFEADIT LVQ G ITIAVNN LT |

FIG. 7D

```
Caenorhabditis elegans    (169) TIPQGDFNYQSVAPRNISQRILSRLPAGAVKNVGNFDFFNYAGILRSVQI
Drosophila melanogaster   (195) TVPQG---RIIEVPNDGGMTIVQS--------------YTFDFNVAGIHRSVH
Mus musculus              (179) TLPPGTIVYKIDTSMYPKGYFVQD--------------TSFDFNVAGIHRSVM
Rattus norvegicus         (179) TLPPGTIVYKIDPSMYPKGYFVQD--------------ISFDFNVAGIHRSVM
Felis catus               (179) TLPPGTILYQIDTSKYPKGYFVQN--------------INFDFNVAGIHRPVL
Canis familiaris          (179) TLPPGTIVYKIDASKYPKGYFVQN--------------TYFDFNVAGIHRPVL
Cercopithecus aethiops    (177) TLPPGTIVYKIDISKYPKGYFIQN--------------TYFDFNVAGIQRSVL
Homo sapiens              (180) TLPPGTIQYLIDTSKYPKGYFVQN--------------TYFDFNVAGIQRSVL
Sulfolobus solfataricus   (133) NLPPAR-----------------DLNN-----------AAFDFNGGIHRPVYI
Thermotoga maritima       (124) GFPSKVPDSGTHTVGFFGSFPPAN--------------FDFPVGIIRPVL_I
Lactobacillus gasseri     (144) AIPCG------IEEILDNGQKLAQP--------------YEFFNVSGIMRNVW
Escherichia coli          (142) TIPPG------MVITDENGKKKQS--------------YFHDFNVAIHRSVM
Staphylococcus sp.        (140) TL-PVG------LYSERHEEGLGKVIRNK---------PNFDFNVASIHRPVKI
Aspergillus nidulans      (181) IIPPGD------LVTSEYTGKKQS--------------YQHDFYNVAGIARSIW
Penicillium canescens     (179) IIPPGK------ITTGNATGKRIQT--------------YQHDFYNVAGIARSIW
Scopulariopsis sp.        (175) IIPPG-------EVVTNEAGKLRQD--------------YNHDFYNVAGIARSVSL
Gibberella zeae           (143) UIPPG-------RIEAQSDGSRKQS--------------YQHDFYNVAGIARSVWL Consensus                 (201) TLPPG        TD          G         VQ         FDFFNYAGL RSV L
```

FIG.7E

| Caenorhabditis elegans | (219) | MKIP-SVYTQNINIVADHTGS----FFFETAVSSLDG------VRVE |
|---|---|---|
| Drosophila melanogaster | (233) | YTTP-RTFIEEVEMINLSKDAT--VGEMFTYSVSINGSAANEADNVLQIQ |
| Mus musculus | (220) | YTTP-TTYIDDITVITNVEQDI---GLMITMWTSVQG------SEHFQLE |
| Rattus norvegicus | (220) | YTTP-TTYIDDITVITDVRDV---GLVNVWISVQG------SDHFQLE |
| Felis catus | (220) | YTTP-TTYIDDITISTSVNQDT---GLVDYQIFVEG------GEHFQLE |
| Canis familiaris | (220) | YTTP-TTYIDDITVITGDQDT---GLVDYQIFVQG------SEHFQLE |
| Cercopithecus aethiops | (218) | YTTP-TAYIDDITVITGVEHDT---GLVNYQISVKG------SNLFELE |
| Homo sapiens | (221) | YTTP-TTYIDDITVITSVEQDS---GLVMVQISVKG------SNLFKLE |
| Sulfolobus solfataricus | (160) | EFVD-ECHVEDITVMTKSYGHLK---MEILSECNQR------FSLR |
| Thermotoga maritima | (163) | EFID-HARTLDIWDISESEPEK-KLGKVKVKIEVSEEAVG------QEMT |
| Lactobacillus gasseri | (179) | LALP-QSQTNFKLNYQLANN----KATITNIEANN------NAEFK |
| Escherichia coli | (177) | YTTP-NTWVDDITVTHMAQCN--HASVDWQVVANGDVS--------- |
| Staphylococcus sp. | (179) | YTTP-FTYVEDISWTDFNGPT---GTMITVDFQG------KAETVK |
| Aspergillus nidulans | (217) | YSVPKDQFIKDITVPDDMGDAETGWVSYTVQTSNAT------SGPIR |
| Penicillium canescens | (215) | YSVP-QQHIQDITVTDVDGD----NGLINYEVEVANQT------TGQIQ |
| Scopulariopsis sp. | (210) | YSVP-DVHVSDVTVITENDDEGN--EGTWNYSVETSGSN------DTQAR |
| Gibberella zeae | (178) | YSVP-KVFINDISMGTDLLGDG--TGIMEFDIRTSGELQA----DARWR |
| Consensus | (251) | YTTP  TYIDDITV T V  D       GLV YIVG              L |

| | | |
|---|---|---|
| Caenorhabditis elegans | (310) | ILDG---ELADIYREQFGFRTVTWSDSQLFINSKPFYCLGFGMHEDFEI |
| Drosophila melanogaster | (330) | LATND--ELLDVYRLKMGIRLSWNSQQFLINGKPWYFRGFGRHEDSDI |
| Mus musculus | (306) | VTTTES---VTDYYTLPVGIRTVAVTKSKFLINGKPFYFQGVNKHEDSDI |
| Rattus norvegicus | (306) | MTTPES---VSDFYTLPVGIRTVAVTKSKFLINGKPFYFQGVNKHEDSDI |
| Felis catus | (306) | TAQTAAGSVSDFYTLPVGIRTVAVTEHQFLINGKPFYFHGVNKHEDADI |
| Canis familiaris | (306) | TAQMAAGPVSDFYTLPVGIRTVAVTERQFLINGKPFYFHGVNKHEDADI |
| Cercopithecus aethiops | (304) | TAQTSLGPVSDFYTLPVGIRTVAVTESQFLINGKPFYFHGVNKHEDADI |
| Homo sapiens | (307) | TAQTSLGPVSDFYTLPVGIRTVAVTKSQFLINGKPFYFHGVNKHEDADI |
| Sulfolobus solfataricus | (240) | MYVGGN--LKDSVVERIGFRDVEVKDGKIYLNGKPIFLKGFGRHEDFPI |
| Thermotoga maritima | (248) | EK------DEYTLDIGIRTLSWDEKRLYLNGKPVFLKGFGKHEEFPV |
| Lactobacillus gasseri | (258) | MLEDG---KTVDEYTDKIGIRTKIVNDKILNNHPIYLKGFGKHEDFNV |
| Escherichia coli | (256) | AKS----QTECDIYPLRVGIRSVAVKGEQFLINKPYFIGFGRHEDADL |
| Staphylococcus sp. | (259) | VNDG---LTIDVYEEPFCVRIVEVNDGKFLINNKPYFKGFGKHEDTPI |
| Aspergillus nidulans | (303) | ILSA-S-QRLIDIYTLPIGIRTVAVGNGTILMNEPVYLTGFGKHEDSPI |
| Penicillium canescens | (296) | IVGS-S-GDVVDIYNLATGVRTVKVAGSQFLINGKPFYFIGFGKHEDTAV |
| Scopulariopsis sp. | (293) | LS--D-DTVVDIYDLPVGVRSVREGNQFLINGKPYFIGFGKHEDSPV |
| Gibberella zeae | (262) | VRGEH-DEILDIYNLAVGIRSVEIRDGRFLINGKPFYFIGFGKHEDGPV |
| Consensus | (351) | L V D YTLPVGIRTVAV QFLINGKPYYF GFGKHEDADI |

FIG.7H

|  | | Signature 1 | |
|---|---|---|---|
| Caenorhabditis elegans | (347) | IGRGFNQAIMTKDLNLEEMGGNCYRTLHYPYSEERMFENDRRGTAVIVE |
| Drosophila melanogaster | (378) | RGKGFDNALMVRDFNLLKWIGANAYRTSHYPYSEESMQFADEHGIMIDE |
| Mus musculus | (353) | RGKGFDWPLLIKDFNLLKWIGANSFRTSHYPYAEEVLQLCDRYGIVVDE |
| Rattus norvegicus | (353) | RGKGFDWPLLIKDFNLLKWIGANSFRTSHYPYSEEVLQLCDRYGIVVDE |
| Felis catus | (356) | RGKGFDWPLLVKDFNLLRWIGANAFRTSHYPYAEEVMQLCDRYGIVVDE |
| Canis familiaris | (356) | RGKGFDWPLLVKDFNLLRWIGANAFRTSHYPYAEEVMQLCDRYGIVVDE |
| Cercopithecus aethiops | (354) | RGKGFDWPLLVKDFNLLRWIGANAFRTSHYPYAEEVMQMCDRYGIVVDE |
| Homo sapiens | (357) | RGKGFDWPLLVKDFNLLRWIGANAFRTSHYPYAEEVMQMCDRYGIVVDE |
| Sulfolobus solfataricus | (287) | LGKFTYGAVLVRDFMRKIGANSFRTSHYPYSNEHLDLADEMGFLVLE |
| Thermotoga maritima | (290) | LGQGIFYPLMIKDFNLLKWINANSFRTSHYPYSEEWLDLADRLGIVIDE |
| Lactobacillus gasseri | (305) | LGFAVNESIIKRDYECMKWIGANQFRSSHYPYAEEWYQYADKYGFLIDE |
| Escherichia coli | (302) | RGKGFDNVLMHDHALMDWIGANSYRTSHYPYAEEMLDWADEHGIVVDE |
| Staphylococcus sp. | (306) | NGRGFNEASNMVDFNILKWIGANSFRTSHYPYSEEVMRLADREGLVIDE |
| Aspergillus nidulans | (351) | RGKG-HDIAYLVHDFQLDWIGANSFRTSHYPYAEEVMEFADRQGILIDE |
| Penicillium canescens | (344) | RGKG-HDPAYMHDFQMKWIGANSFRTSHYPYAEEVMDFADRNGIVVIDE |
| Scopulariopsis sp. | (340) | RGKGYDPAYMHDFFEMKWIGANSFRTSHYPYAEEVMEYADRIGIVVDE |
| Gibberella zeae | (311) | RGRGVDASYMIHDYRLMKWIGANSFRTSHYPYAEEVMEYADRHGVVINE |
| Consensus | (401) | RGKGFD ALLVKDFNLLKWIGANSFRTSHYPYAEEVM LADRYGIVVIDE |

FIG. 71

| | | | |
|---|---|---|---|
| Caenorhabditis elegans | (397) | TPAVGL KGFSKANN---------------- | ----------------NL VKMLQDM DRDKN |
| Drosophila melanogaster | (428) | CP---SVDTENFSQ---------------- | ----------------ELLGK KSSLEQ IHRDN |
| Mus musculus | (403) | CPGVGIV PQSFGN---------------- | ----------------ESLRH LEVMEEL VRRDKN |
| Rattus norvegicus | (403) | CPGVGIV PQSFGN---------------- | ----------------VSLRH LEVMDEL VRRDKN |
| Felis catus | (406) | CPGVGIV VESYSN---------------- | ----------------VSLQH LEVMEEL VRRDKN |
| Canis familiaris | (406) | SPGVGIM VQSYSN---------------- | ----------------VSLQH LEVMGEL VRRDKN |
| Cercopithecus aethiops | (404) | CPGVGL AL PQFFNN---------------- | ----------------VSLQN MRVMEE VRRDKN |
| Homo sapiens | (407) | CPGVGL AL PQFFNN---------------- | ----------------VSLHH MQVMEE VRRDKN |
| Sulfolobus solfataricus | (337) | PPLCYSNISRVMSQEE--------IAKMFGDVKYFEKVRDTIK MRQHKN | |
| Thermotoga maritima | (340) | APHVGI TRYH-------------YN----PETQKIAEDNIRRMIDR KN | |
| Lactobacillus gasseri | (355) | VPAVGL NRSITNFLNVTSNQSHFFASKTVPELKKV EQEIKEM DRDQR | |
| Escherichia coli | (352) | TAAVGFN SLGIGFEAGNKPKELYSEEAVNGETQQAH LQAIKELI ARDKN | |
| Staphylococcus sp. | (356) | TPAVGVH NFMATTGLGEGSE--RVSTWEKIRTFEH QDVLREL VSRDKN | |
| Aspergillus nidulans | (401) | TPAVG LAYSIGAGISTDTSRV-TFAPDGINNNTRAA AQALREL IARDKN | |
| Penicillium canescens | (394) | TPAVG NIAL-MGVSESGAPQ-TFTPDAINDKTQEA KQAIREL IARDKN | |
| Scopulariopsis sp. | (390) | VAAVGL N GISAGLRGDEPPK-TFTEDKVNNETQKT AQALREL IHRDKN | |
| Gibberella zeae | (361) | TAAVGL N NIVSGMFGNKQLA-TFSPDTMSSKTQASH EQAIREL ISRDKN | |
| Consensus | | PAVGL L N T H IRELI RDKN | |

```
Caenorhabditis elegans    (474)  -NFDNDQTADLMQFCVNRYYGWYIDMG-YIPWINQSVYWDISLWRETFH
Drosophila melanogaster   (504)  -SNTQDKAGRSLDIISFNRVNAWYSNAG-RDMITQNVIDAIAWNKRYN
Mus musculus              (482)  -KYDADLGAPYVDVICVNSYFSWVHDYG-HLEVIQPQNSQFENWYKTHQ
Rattus norvegicus         (482)  -RYDADMGAPYVDVICVNSYLSWVHDYG-HLEVIQLQTSQFENWYKMYQ
Felis catus               (485)  -NYEADLGAPYVDVICVNSYYSWVHDYG-HMEVIQLQATQFENWYRTYQ
Canis familiaris          (485)  -NYEADLGAPYVDVICVNSYYSWVHDYG-HMEVIQLQLATFFENWYRTYQ
Cercopithecus aethiops    (483)  -NYAADKGAPYVDVICLNSYYSWVHDYG-HLEIQRQLTTQFENWYKTMQ
Homo sapiens              (486)  -NYAADKGAPYVDVICLNSYYSWVHDYG-HLEIIQLQLATQFENWYKKMQ
Sulfolobus solfataricus   (426)  --SVRDLALEYVDVISLNIYH-GWYTEWG-DIDSGVKVVAIELEEIHKKFP
Thermotoga maritima       (421)  DERTRDVALKYFDIVCVRYGWVIYQG-RIEEGLQAIEKDIEELYARHR
Lactobacillus gasseri     (454)  -GPKVDKLHPLCDFVCLNRYGWVVAGGPEIVNAKKMEDEIDGWQNLKL
Escherichia coli          (450)  -DAHIDTISDLFDWLCINRYGWVQSE-DIETAEKVLEKEILAWQEKLH
Staphylococcus sp.        (453)  -TPETDKVAELIDVIALNRVNGWVIFDGG-DLEAAKVHLRQEFHAWNKRCP
Aspergillus nidulans      (499)  -TYETDTISDLFDVCLNRYFGWVSYTG-DLESAGKALHEELDGWVAKYP
Penicillium canescens     (490)  -TYQLDRISDLFDVSCINRYFGWVSQTG-DLEEEAAALEKELHQWQEKFH
Scopulariopsis sp.        (487)  -TVDKCLISDLFDFLSLNRYGWVIVQTG-DLSAEVAMEEELLQWVDEMD
Gibberella zeae           (459)  -KPDTDRIADLFDWCMRYYGWVTQTG-NLKAAEVALEAIRSWQEAMA
Consensus                 (551)        YD D GA VDVICLNRYYGWY D G     LE A   L   ELE WK Y
```

FIG.7L

| | | |
|---|---|---|
| Caenorhabditis elegans | (522) | -KPITIVTEYGADSIPGLNQEPSVDFSEQMNEVIQETDHAFDALVKDHTI |
| Drosophila melanogaster | (552) | -KPIIMSEYGADTLEGLHMQPAYVWSEEFQTEVFSRHFKAFDELRKKGWF |
| Mus musculus | (530) | -KPIIQSEYGADAIPGHEDPPRMFSEEYQKAVLENVHSMDQKRKE-YV |
| Rattus norvegicus | (530) | -KPIIQSEYGADAVSGLHEDPPRMFSEEYQTALLENVHLILDEKRKE-YV |
| Felis catus | (533) | -KPIIQSEYGADTIAGFHQDPPLMFSEEYQKGLLEQMYLMDQKRKE-YV |
| Canis familiaris | (533) | -KPIIQSEYGAETIAGFHQDPPLMFSEEYQKGLLEQMYLMDQKRKE-YV |
| Cercopithecus aethiops | (531) | -KPIIQSEYGAETIVGFHQDPPLMFTEEYQKSLLEQYHVMDQKRRK-YV |
| Homo sapiens | (534) | -KPIIQSEYGAETIAGFHQDPPLMFTEEYQKSLLEQYHLGLDQKRRK-YV |
| Sulfolobus solfataricus | (473) | EKPIIITTEFGADAIYGLHSDPPQWSEEYQSEMIRKMIEALREKDYI--- |
| Thermotoga maritima | (470) | -KPIFVTEFGADAIAGIHYDPPQMFSEEYQAELVEKTIRLLLKKDYI--- |
| Lactobacillus gasseri | (503) | NKPFVFVTEFGADTLSSSHRLPDEMSQFYQNEYYQMFDIFKKYPPFI--- |
| Escherichia coli | (498) | -QPIIMTEYGVDTLAGLHSMYTDMSEEYQCAWLDMYHRVFDRVSAV--- |
| Staphylococcus sp. | (501) | GKPIIMTEYGADTIAGLHDIDPMFIEEYQVEYYQANMVFDEFENF--- |
| Aspergillus nidulans | (547) | TKPIIISEYGADTIAGLHSVLGLIWSEEFQIELDVYHGVFDQFQNV--- |
| Penicillium canescens | (538) | -RPIVMTEYGADTLAGLHSILGLPWSEEFQVQMLDMYHRVFDRIESM--- |
| Scopulariopsis sp. | (535) | -KPIIMTEYGADTLAGLHAVDEVLWSEEYQTNLLRMSHKVFDSIDSI--- |
| Gibberella zeae | (507) | AKPLIMTEYGTDIVAGLHTVCDVPWTEEYQVRFLDMYHRVFDRIDNV--- |
| Consensus | (601) | KPIIISEYGADTIAGLH DPPLMFSEEYQ LLE YH VFD |

| Organism | Pos | Sequence |
|---|---|---|
| Caenorhabditis elegans | (620) | SNIDTTIWT--------------- |
| Drosophila melanogaster | (650) | RDLDQCSFPEDLFTYIADLIS- |
| Mus musculus | (627) | NETGGHGSGPRTQCFGSRPFTF |
| Rattus norvegicus | (627) | NETRGYGSVPRTQCMGSRPFTF |
| Felis catus | (630) | NETRYPWSAVKSQCLENSPFTL |
| Canis familiaris | (630) | NETGHHRSAAKSQCLENSPFAL |
| Cercopithecus aethiops | (628) | NETRYPHSIAKSQCLENSPFT- |
| Homo sapiens | (631) | NETRYPHSVAKSQCLENSPFT- |
| Sulfolobus solfataricus | (569) | RS-------------------- |
| Thermotoga maritima | (564) | ---------------------- |
| Lactobacillus gasseri | (599) | ---------------------- |
| Escherichia coli | (593) | FGEKPQQGGKQ----------- |
| Staphylococcus sp. | (597) | DFGYKN---------------- |
| Aspergillus nidulans | (643) | SS-------------------- |
| Penicillium canescens | (633) | KN-------------------- |
| Scopulariopsis sp. | (631) | FPKLGNGTSGA----------- |
| Gibberella zeae | (603) | GPRKIEVTKQ------------ |
| Consensus | (701) | |

SEQUENCE LISTING

```
<160> NUMBER OF SEQ ID NOS: 37

<210> SEQ ID NO 1
<211> LENGTH: 1926
<212> TYPE: DNA
<213> ORGANISM: Scopulariopsis sp. isoate RP38.3

<400> SEQUENCE: 1
atgcgcctct ctaatatccc ccttctgcgc ccttgggccg ctctgtccct agccaccctc      60
atcggcctgt cctctggtgc cgacactgac caatggaaga cgctcaagcc ccaagctaat     120
gctattcggg agctactctc ccttgatggt acctggaact ttgccctccc gcaatcacgc     180
gaaattgagg aagaccaggg ctggactagc gttattccac ccaaactgca aatcccagtg     240
cccgccagct acaacgacat cttcaccgat ccggcgatcc ggaacaacgt tggctgggca     300
tactatcagc gccacgccat tgtcccccag acctggtctg agggacgcta ctatgttcgc     360
ttcgactctg ttacgcacga ggccaaggtc tacgtcaacg acgaggaagt cggaggccat     420
gtcggtggat atactccctt cgaggttgac ctgaccgacc ttgtgtcgcc cggagagcag     480
ttccgcctga ctgttgctgt caacaatatc ctgacttggc agaccatccc ccctggtgag     540
gtcgtgacca acgaggctgg taagcttcga caggactaca accacgactt ctacaactac     600
gctggaattg cacgttccgt ctcgctatac tccgtgcctg atgttcatgt tagcgacgtc     660
actgttacta ccgagaacga cgacgagggc aacgagggca ccgtcaacta ctctgtcgag     720
accagcgggt ctaacgacac tcaggctagg gtcactttga ttgatgagga cggcaacgag     780
gtcgccgagg catcggagct ggaggggagc ttgaacgtga gccccgtgaa tctctggcag     840
ccgggcgcgg cgtacctcta cactcttcgc gttgaactcc tttcggacga taccgtcgtc     900
gacacttatg atttaccggt tggtgtacgg tccgttaggg ttgaaggaaa ccagttcctc     960
atcaacggca agcccttcta cttcaccggc tttggcaagc acgaggacag ccccgtccgc    1020
ggaaagggct acgacccggc ctacatgatc catgattttg agctcatgaa gtggatgggc    1080
gccaactcct tccggacctc ccactacccc tacgccgagg aggtcatgga gtacgccgac    1140
```

-continued

```
cgtcacggca tcgtcgtcat cgacgaggtc gccgccgtcg gtctgaacct gggcatcagc   1200
gcaggcctca ggggagatga gccgcccaag accttcacgg aggacaaggt taacaacgag   1260
acgcaaaaga cacacgccca ggccctccgt gagttgatcc accgtgacaa gaaccacgcc   1320
tccgttgtca gctggtgcgt caccaacgag cccgcctccg ccgaggacgg tgcccgcgag   1380
tacttccagc ccctggtcga gctaacccgc gagctggacc ccacccgccc cgtcaccttc   1440
accaacgtca tgggcgccac cgtcgacaag tgcctcatct ccgatctttt cgacttcctt   1500
tctctcaacc gctactacgg gtggtacgtc caaacgggcg acctggagtc cgccgaggtc   1560
gccatggagg aggagctcct ccagtgggtc gacgagtatg acaagcctat catcatgtcc   1620
gagtacggcg ccgacaccct ggccggtctc cacgcggtcg acgaggtgct ctggtccgag   1680
gagtaccaga ccaacctcct cgcatgtcg cacaaggtct tgacagcat tgactccatt    1740 gttggcgagc acgtgtggaa ctttgctgat tccagactc ctcatactgg tgtcaaccgt    1800
gttgatggaa acaagaaggg tgtgtttacg cgtgagcgga ggcctaaggc cgcggcacat   1860
gagctcaaga ggcggtggct ggacgagggg ttcccgaagc tggggaacgg tacttccggt   1920
gcttaa                                                              1926
```

<210> SEQ ID NO 2
<211> LENGTH: 641
<212> TYPE: PRT
<213> ORGANISM: Scopulariopsis sp. isolate RP38.3

<400> SEQUENCE: 2

```
Met Arg Leu Ser Asn Ile Pro Leu Leu Arg Pro Trp Ala Ala Leu Ser
 1               5                  10                  15

Leu Ala Thr Leu Ile Gly Leu Ser Ser Gly Ala Asp Thr Asp Gln Trp
            20                  25                  30

Lys Thr Leu Lys Pro Gln Ala Asn Ala Ile Arg Glu Leu Leu Ser Leu
        35                  40                  45

Asp Gly Thr Trp Asn Phe Ala Leu Pro Gln Ser Arg Glu Ile Glu Glu
    50                  55                  60

Asp Gln Gly Trp Thr Ser Val Ile Pro Lys Leu Gln Ile Pro Val
65                  70                  75                  80

Pro Ala Ser Tyr Asn Asp Ile Phe Thr Asp Pro Ala Ile Arg Asn Asn
                85                  90                  95

Val Gly Trp Ala Tyr Tyr Gln Arg His Ala Ile Val Pro Gln Thr Trp
            100                 105                 110

Ser Glu Gly Arg Tyr Tyr Val Arg Phe Asp Ser Val Thr His Glu Ala
        115                 120                 125

Lys Val Tyr Val Asn Asp Glu Glu Val Gly Gly His Val Gly Gly Tyr
    130                 135                 140

Thr Pro Phe Glu Val Asp Leu Thr Asp Leu Val Ser Pro Gly Glu Gln
145                 150                 155                 160

Phe Arg Leu Thr Val Ala Val Asn Asn Ile Leu Thr Trp Gln Thr Ile
                165                 170                 175

Pro Pro Gly Glu Val Val Thr Asn Glu Ala Gly Lys Leu Arg Gln Asp
            180                 185                 190

Tyr Asn His Asp Phe Tyr Asn Tyr Ala Gly Ile Ala Arg Ser Val Ser
        195                 200                 205

Leu Tyr Ser Val Pro Asp Val His Val Ser Asp Val Thr Val Thr Thr
    210                 215                 220
```

```
Glu Asn Asp Asp Glu Gly Asn Glu Gly Thr Val Asn Tyr Ser Val Glu
225                 230                 235                 240

Thr Ser Gly Ser Asn Asp Thr Gln Ala Arg Val Thr Leu Ile Asp Glu
            245                 250                 255

Asp Gly Asn Glu Val Ala Glu Ala Ser Glu Leu Glu Gly Ser Leu Asn
        260                 265                 270

Val Ser Pro Val Asn Leu Trp Gln Pro Gly Ala Ala Tyr Leu Tyr Thr
    275                 280                 285

Leu Arg Val Glu Leu Leu Ser Asp Asp Thr Val Val Asp Thr Tyr Asp
290                 295                 300

Leu Pro Val Gly Val Arg Ser Val Arg Val Glu Gly Asn Gln Phe Leu
305                 310                 315                 320

Ile Asn Gly Lys Pro Phe Tyr Phe Thr Gly Phe Gly Lys His Glu Asp
                325                 330                 335

Ser Pro Val Arg Gly Lys Gly Tyr Asp Pro Ala Tyr Met Ile His Asp
            340                 345                 350

Phe Glu Leu Met Lys Trp Met Gly Ala Asn Ser Phe Arg Thr Ser His
        355                 360                 365

Tyr Pro Tyr Ala Glu Glu Val Met Glu Tyr Ala Asp Arg His Gly Ile
    370                 375                 380

Val Val Ile Asp Glu Val Ala Ala Val Gly Leu Asn Leu Gly Ile Ser
385                 390                 395                 400

Ala Gly Leu Arg Gly Asp Glu Pro Pro Lys Thr Phe Thr Glu Asp Lys
                405                 410                 415

Val Asn Asn Glu Thr Gln Lys Thr His Ala Gln Ala Leu Arg Glu Leu
            420                 425                 430

Ile His Arg Asp Lys Asn His Ala Ser Val Val Ser Trp Cys Val Thr
        435                 440                 445

Asn Glu Pro Ala Ser Ala Glu Asp Gly Ala Arg Glu Tyr Phe Gln Pro
    450                 455                 460

Leu Val Glu Leu Thr Arg Glu Leu Asp Pro Thr Arg Pro Val Thr Phe
465                 470                 475                 480

Thr Asn Val Met Gly Ala Thr Val Asp Lys Cys Leu Ile Ser Asp Leu
                485                 490                 495

Phe Asp Phe Leu Ser Leu Asn Arg Tyr Tyr Gly Trp Tyr Val Gln Thr
            500                 505                 510

Gly Asp Leu Glu Ser Ala Glu Val Ala Met Glu Glu Glu Leu Leu Gln
        515                 520                 525

Trp Val Asp Glu Tyr Asp Lys Pro Ile Ile Met Ser Glu Tyr Gly Ala
    530                 535                 540

Asp Thr Leu Ala Gly Leu His Ala Val Asp Glu Val Leu Trp Ser Glu
545                 550                 555                 560

Glu Tyr Gln Thr Asn Leu Leu Arg Met Ser His Lys Val Phe Asp Ser
                565                 570                 575

Ile Asp Ser Ile Val Gly Glu His Val Trp Asn Phe Ala Asp Phe Gln
            580                 585                 590

Thr Pro His Thr Gly Val Asn Arg Val Asp Gly Asn Lys Lys Gly Val
        595                 600                 605

Phe Thr Arg Glu Arg Arg Pro Lys Ala Ala His Glu Leu Lys Arg
    610                 615                 620

Arg Trp Leu Asp Glu Gly Phe Pro Lys Leu Gly Asn Gly Thr Ser Gly
625                 630                 635                 640

Ala
```

<210> SEQ ID NO 3
<211> LENGTH: 1905
<212> TYPE: DNA
<213> ORGANISM: Penicillium canescens isolate RPK

<400> SEQUENCE: 3

| | | |
|---|---|---|
| atgaaattcc ttacgggatt gtcgctgctg tctcttgctg ctccatcgtt gggtacacct | 60 |
| gcagctcggc actttccacg caatgaaatg acccaacatg aacagcccct gatcaaagtc | 120 |
| aggccccaac gaacttcatc tcgagagctt gtgaaccttg atggtctatg gaaattcgcc | 180 |
| ctcgcatctg gcctcaatga cacggcccaa ccgtggacag cgccattacc caaaggtctt | 240 |
| gaatgtccag tcccggcctc ttacaacgac atcttcatca gccgggagat tcacgaccat | 300 |
| gtgggatggg tttactatca gcgtgaggtc attgtcccca aggctggtc tcaggagcga | 360 |
| tatctcgtgc gagccgaatc cgctacgcac catggtcgca tctatgtcaa caaccggctt | 420 |
| gttgccgagc atgtgggcgg ctatacacct tttgaagcgg acgtcactga attagtcgcc | 480 |
| cccggagaga aatttcgctt gacgattggt gtcaacaacg agcttaccca tgagactatc | 540 |
| ccacctggaa aaatcacgac agggaacgcg actggcaaga gaatccgac ctatcaacat | 600 |
| gactttaca actatgctgg tctcgcccga tctatctggc tttattctgt accccagcaa | 660 |
| catatccagg atattactgt ggttacagat gttgatggtg acaatggtct gattaactac | 720 |
| gaggtcgaag tggcgaacca gacgacgggg cagatccaga tctcagtgat cgacgaggat | 780 |
| ggagctattg ttgcaaaggc ctcgggagct cagggtactg tcacaattcc ctcagtcaag | 840 |
| ctatggcaac ctggcgccgc atatctctac caactccagg tcaacatcgt gggttctagc | 900 |
| ggcgatgtag tcgacaccta caatttggct acgggcgtgc gtactgtcaa ggttgccggg | 960 |
| tcacaattct aataaatgg aaagcctttc tactttaccg gttttggcaa acatgaagac | 1020 |
| acagcagtac gtggcaaagg acatgaccca gcatacatgg ttcacgatt ccaactcatg | 1080 |
| aaatggattg gagcaaattc ttttcggact tcacactatc cttacgcgga agaggtcatg | 1140 |
| gatttcgcag atcgaaatgg aattgtcgtg atcgatgaaa cacctgccgt tggtctgaac | 1200 |
| attgccttga tgggcgtatc tgagagtggt gccccacaaa catttacgcc agatgcgatt | 1260 |
| aacgataaaa cccaagaggc ccacaagcag gcgattcgtg agctcattgc ccgagacaaa | 1320 |
| aaccatgcca gtgttgtcat gtggtctatt gccaacgagc ccgcatctca tgaagatgga | 1380 |
| gctcgcgaat acttcgagcc actgaccaat ttgactcgtc aacttgatcc aactcgccct | 1440 |
| attacatttg ctaacgtcgg cacggcgaca tatcagctgg atcggatctc tgatctgttt | 1500 |
| gatgtcagtt gcataaatcg gtatttcgga tggtattctc aaacaggaga ccttgaggaa | 1560 |
| gcagaggcag ctcttgaaaa ggagctgcat ggatggcaag agaaattcca caggccgatc | 1620 |
| gtcatgaccg aatatggtgc agatacccct gcaggcctc actctatcct cggactgcct | 1680 |
| tggagcgaag agttccaagt acaaatgcta gacatgtacc atcgagtgtt tgatcgcatt | 1740 |
| gagtcgatgg caggcgagca tgtttggaac ttcgccgatt ccagaccaa cttgggtatc | 1800 |
| atccgagtag acggtaacaa gaagggtgtt ttcacccgtg accgaaagcc aaaggcggca | 1860 |
| gctcatagtt tgagggcaag gtggactagt attgataaga attaa | 1905 |

<210> SEQ ID NO 4
<211> LENGTH: 634
<212> TYPE: PRT
<213> ORGANISM: Penicillium canescens isolate RPK -continued

<400> SEQUENCE: 4

```
Met Lys Phe Leu Thr Gly Leu Ser Leu Leu Ser Leu Ala Ala Pro Ser
1               5                   10                  15

Leu Gly Thr Pro Ala Ala Arg His Phe Pro Arg Asn Glu Met Thr Gln
            20                  25                  30

His Glu Gln Pro Leu Ile Lys Val Arg Pro Gln Arg Thr Ser Ser Arg
        35                  40                  45

Glu Leu Val Asn Leu Asp Gly Leu Trp Lys Phe Ala Leu Ala Ser Gly
    50                  55                  60

Leu Asn Asp Thr Ala Gln Pro Trp Thr Ala Pro Leu Pro Lys Gly Leu
65                  70                  75                  80

Glu Cys Pro Val Pro Ala Ser Tyr Asn Asp Ile Phe Ile Ser Arg Glu
                85                  90                  95

Ile His Asp His Val Gly Trp Val Tyr Tyr Gln Arg Glu Val Ile Val
            100                 105                 110

Pro Lys Gly Trp Ser Gln Glu Arg Tyr Leu Val Arg Ala Glu Ser Ala
        115                 120                 125

Thr His His Gly Arg Ile Tyr Val Asn Asn Arg Leu Val Ala Glu His
    130                 135                 140

Val Gly Gly Tyr Thr Pro Phe Glu Ala Asp Val Thr Glu Leu Val Ala
145                 150                 155                 160

Pro Gly Glu Lys Phe Arg Leu Thr Ile Gly Val Asn Asn Glu Leu Thr
                165                 170                 175

His Glu Thr Ile Pro Pro Gly Lys Ile Thr Thr Gly Asn Ala Thr Gly
            180                 185                 190

Lys Arg Ile Gln Thr Tyr Gln His Asp Phe Tyr Asn Tyr Ala Gly Leu
        195                 200                 205

Ala Arg Ser Ile Trp Leu Tyr Ser Val Pro Gln Gln His Ile Gln Asp
    210                 215                 220

Ile Thr Val Val Thr Asp Val Asp Gly Asp Asn Gly Leu Ile Asn Tyr
225                 230                 235                 240

Glu Val Glu Val Ala Asn Gln Thr Thr Gly Gln Ile Gln Ile Ser Val
                245                 250                 255

Ile Asp Glu Asp Gly Ala Ile Val Ala Lys Ala Ser Gly Ala Gln Gly
            260                 265                 270

Thr Val Thr Ile Pro Ser Val Lys Leu Trp Gln Pro Gly Ala Ala Tyr
        275                 280                 285

Leu Tyr Gln Leu Gln Val Asn Ile Val Gly Ser Ser Gly Asp Val Val
    290                 295                 300

Asp Thr Tyr Asn Leu Ala Thr Gly Val Arg Thr Val Lys Val Ala Gly
305                 310                 315                 320

Ser Gln Phe Leu Ile Asn Gly Lys Pro Phe Tyr Phe Thr Gly Phe Gly
                325                 330                 335

Lys His Glu Asp Thr Ala Val Arg Gly Lys His Asp Pro Ala Tyr
            340                 345                 350

Met Val His Asp Phe Gln Leu Met Lys Trp Ile Gly Ala Asn Ser Phe
        355                 360                 365

Arg Thr Ser His Tyr Pro Tyr Ala Glu Glu Val Met Asp Phe Ala Asp
    370                 375                 380

Arg Asn Gly Ile Val Val Ile Asp Glu Thr Pro Ala Val Gly Leu Asn
385                 390                 395                 400

Ile Ala Leu Met Gly Val Ser Glu Ser Gly Ala Pro Gln Thr Phe Thr
                405                 410                 415
```

```
Pro Asp Ala Ile Asn Asp Lys Thr Gln Glu Ala His Lys Gln Ala Ile
            420                 425                 430

Arg Glu Leu Ile Ala Arg Asp Lys Asn His Ala Ser Val Val Met Trp
        435                 440                 445

Ser Ile Ala Asn Glu Pro Ala Ser His Glu Asp Gly Ala Arg Glu Tyr
    450                 455                 460

Phe Glu Pro Leu Thr Asn Leu Thr Arg Gln Leu Asp Pro Thr Arg Pro
465                 470                 475                 480

Ile Thr Phe Ala Asn Val Gly Thr Ala Thr Tyr Gln Leu Asp Arg Ile
                485                 490                 495

Ser Asp Leu Phe Asp Val Ser Cys Ile Asn Arg Tyr Phe Gly Trp Tyr
            500                 505                 510

Ser Gln Thr Gly Asp Leu Glu Glu Ala Glu Ala Leu Glu Lys Glu
        515                 520                 525

Leu His Gly Trp Gln Glu Lys Phe His Arg Pro Ile Val Met Thr Glu
    530                 535                 540

Tyr Gly Ala Asp Thr Leu Ala Gly Leu His Ser Ile Leu Gly Leu Pro
545                 550                 555                 560

Trp Ser Glu Glu Phe Gln Val Gln Met Leu Asp Met Tyr His Arg Val
                565                 570                 575

Phe Asp Arg Ile Glu Ser Met Ala Gly Glu His Val Trp Asn Phe Ala
            580                 585                 590

Asp Phe Gln Thr Asn Leu Gly Ile Ile Arg Val Asp Gly Asn Lys Lys
        595                 600                 605

Gly Val Phe Thr Arg Asp Arg Lys Pro Lys Ala Ala His Ser Leu
    610                 615                 620

Arg Ala Arg Trp Thr Ser Ile Asp Lys Asn
625                 630

<210> SEQ ID NO 5
<211> LENGTH: 1905
<212> TYPE: DNA
<213> ORGANISM: Penicillium canescens isolate DSM1215

<400> SEQUENCE: 5
atgaaatttc ttacgcgatt gtcgctgcta tctcttgctg ctccatcgtt gggtacacct      60
gcagctcggc actttccacg caatgaaatg ayccaaaatg aacagccctt gatcaaaatc     120
aggccccaac gaacttcatc tcgagaccct gtgaacttg atggtctatg gaaattcgcc      180
ctcgcatctg gccccaatga cacggcccag ccgtggacag cgccattacc caaaggtctt     240
gaatgtccag tcccggcctc ttacaatgac attttcatca gccgggagat ccacgaccat     300
gtgggatggg tttactatca gcgtgaggtc attgtcccca aaggctggtc tcaggagcga     360
tatcttgtgc gagccgaatc cgctacacac catggtcgca tctatgtcaa caaccggctt     420
gttgcggagc atgtgggcgg ctatacacct tttgaagccg acatcactga tttggtcgtc     480
cctggagaga aatttcgttt gacgattggt gtcaacaacg agcttaccca tgagactatc     540
ccaccaggag aaatcacaac agcgaacgcg actggcaaga aatccagac ctatcaacat      600 gacttttaca actatgccgg tctcgcccga tctatctggc tttattctgt accccagcaa     660
catatccagg atattactgt ggttacagat gttgatggtg acaatggtct gatcaactac     720
gaggtcgaag tggcgaacca gacgacgggg cagatccaga tctcagtgat cgacgaggat     780
ggagctattg ttgcaaatgc ctcgggagct cagggtactg tcacaattcc ctcagtcaag     840
ctatggcaac ctggcgccgc atatctctac caactccagg tcaacgtcgt ggattctagc     900
```

-continued

```
ggcgatgtag tcgacaccta taatttggct acgggcgtgc gtactgtcaa gatttccggg    960
tcacaattct tgataaacgg caagcctttc tactttaccg gttttggcag gcatgaagac   1020
acagcagtac gtggcaaagg acatgaccca gcatatatgg ttcacgattt ccaactcatg   1080
aaatggattg gagcaaattc tttccggact tcacacyacc cttatgcaga agaggtcatg   1140
gatttcgcag atcgaaatgg aattgtcgtg atcgatgaaa ctcctgccgt gggtctgaac   1200
attgccttga tgggtgtatc tgagagtggt gccccacaaa catttacgcc agatgggatt   1260
aacgataaga cccaagaggc ccacaaacag gcgattcgtg agctcattgc ccgagacaaa   1320
aaccatgcca gtgttgtcat gtggtctatt gccaatgagc ctgcatctca ggaagatggg   1380
gctcgcgaat acttcgagcc actggccaat ttgactcgtc agcttgatcc aactcgccct   1440
attacatttg ctaatgtcgg cgctgcaaca tatcagctag atcggatctc tgatctgttt   1500
gatgttagtt gcataaatcg gtatttcgga tggtattctc agacaggaga ccttgaggaa   1560
gcagaggcag ctcttgaaaa ggagttgcgt gggtggcaag agaaattcca caggccgatc   1620
attatgagcg aatatggtgc agataccctt gcaggtcttc attctatcct cgcactgcct   1680
tggagcgaag agttccaggt acaaatgcta gacatgtacc atcgagtgtt tgatcgcatt   1740
gagtcgatgg caggcgagca tgtttggaac ttcgcggatt ccagaccaa cttgggtgtc    1800 atccgagtag atggtaacaa gaagggtgtt ttcacgcgtg accgaaagcc aaaggcggca   1860
gctcatagtt tgagggcaag gtggacgaat ggtgataaga attag                  1905
```

<210> SEQ ID NO 6
<211> LENGTH: 634
<212> TYPE: PRT
<213> ORGANISM: Penicillium canescens
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (373)..(373)
<223> OTHER INFORMATION: Xaa can be any naturally occurring amino acid

<400> SEQUENCE: 6

```
Met Lys Phe Leu Thr Arg Leu Ser Leu Leu Ser Leu Ala Ala Pro Ser
 1               5                  10                  15

Leu Gly Thr Pro Ala Ala Arg His Phe Pro Arg Asn Glu Met Xaa Gln
            20                  25                  30

Asn Glu Gln Pro Leu Ile Lys Ile Arg Pro Gln Arg Thr Ser Ser Arg
        35                  40                  45

Asp Leu Val Asn Leu Asp Gly Leu Trp Lys Phe Ala Leu Ala Ser Gly
    50                  55                  60

Pro Asn Asp Thr Ala Gln Pro Trp Thr Ala Pro Leu Pro Lys Gly Leu
65                  70                  75                  80

Glu Cys Pro Val Pro Ala Ser Tyr Asn Asp Ile Phe Ile Ser Arg Glu
                85                  90                  95

Ile His Asp His Val Gly Trp Val Tyr Tyr Gln Arg Glu Val Ile Val
            100                 105                 110

Pro Lys Gly Trp Ser Gln Glu Arg Tyr Leu Val Arg Ala Glu Ser Ala
        115                 120                 125

Thr His His Gly Arg Ile Tyr Val Asn Asn Arg Leu Val Ala Glu His
    130                 135                 140

Val Gly Gly Tyr Thr Pro Phe Glu Ala Asp Ile Thr Asp Leu Val Val
145                 150                 155                 160
```

```
Pro Gly Glu Lys Phe Arg Leu Thr Ile Gly Val Asn Asn Glu Leu Thr
            165                 170                 175

His Glu Thr Ile Pro Pro Gly Glu Ile Thr Thr Ala Asn Ala Thr Gly
            180                 185                 190

Lys Arg Ile Gln Thr Tyr Gln His Asp Phe Tyr Asn Tyr Ala Gly Leu
            195                 200                 205

Ala Arg Ser Ile Trp Leu Tyr Ser Val Pro Gln Gln His Ile Gln Asp
    210                 215                 220

Ile Thr Val Val Thr Asp Val Asp Gly Asp Asn Gly Leu Ile Asn Tyr
225                 230                 235                 240

Glu Val Glu Val Ala Asn Gln Thr Thr Gly Gln Ile Gln Ile Ser Val
                245                 250                 255

Ile Asp Glu Asp Gly Ala Ile Val Ala Asn Ala Ser Gly Ala Gln Gly
                260                 265                 270

Thr Val Thr Ile Pro Ser Val Lys Leu Trp Gln Pro Gly Ala Ala Tyr
            275                 280                 285

Leu Tyr Gln Leu Gln Val Asn Val Val Asp Ser Ser Gly Asp Val Val
    290                 295                 300

Asp Thr Tyr Asn Leu Ala Thr Gly Val Arg Thr Val Lys Ile Ser Gly
305                 310                 315                 320

Ser Gln Phe Leu Ile Asn Gly Lys Pro Phe Tyr Phe Thr Gly Phe Gly
                325                 330                 335

Arg His Glu Asp Thr Ala Val Arg Gly Lys Gly His Asp Pro Ala Tyr
                340                 345                 350

Met Val His Asp Phe Gln Leu Met Lys Trp Ile Gly Ala Asn Ser Phe
            355                 360                 365

Arg Thr Ser His Xaa Pro Tyr Ala Glu Glu Val Met Asp Phe Ala Asp
    370                 375                 380

Arg Asn Gly Ile Val Val Ile Asp Glu Thr Pro Ala Val Gly Leu Asn
385                 390                 395                 400

Ile Ala Leu Met Gly Val Ser Glu Ser Gly Ala Pro Gln Thr Phe Thr
                405                 410                 415

Pro Asp Gly Ile Asn Asp Lys Thr Gln Glu Ala His Lys Gln Ala Ile
            420                 425                 430

Arg Glu Leu Ile Ala Arg Asp Lys Asn His Ala Ser Val Val Met Trp
    435                 440                 445

Ser Ile Ala Asn Glu Pro Ala Ser Gln Glu Asp Gly Ala Arg Glu Tyr
450                 455                 460

Phe Glu Pro Leu Ala Asn Leu Thr Arg Gln Leu Asp Pro Thr Arg Pro
465                 470                 475                 480

Ile Thr Phe Ala Asn Val Gly Ala Ala Thr Tyr Gln Leu Asp Arg Ile
                485                 490                 495

Ser Asp Leu Phe Asp Val Ser Cys Ile Asn Arg Tyr Phe Gly Trp Tyr
            500                 505                 510

Ser Gln Thr Gly Asp Leu Glu Glu Ala Glu Ala Leu Glu Lys Glu
    515                 520                 525

Leu Arg Gly Trp Gln Glu Lys Phe His Arg Pro Ile Ile Met Ser Glu
    530                 535                 540

Tyr Gly Ala Asp Thr Leu Ala Gly Leu His Ser Ile Leu Ala Leu Pro
545                 550                 555                 560

Trp Ser Glu Glu Phe Gln Val Gln Met Leu Asp Met Tyr His Arg Val
                565                 570                 575
```

```
Phe Asp Arg Ile Glu Ser Met Ala Gly Glu His Val Trp Asn Phe Ala
            580                 585                 590
Asp Phe Gln Thr Asn Leu Gly Val Ile Arg Val Asp Gly Asn Lys Lys
        595                 600                 605
Gly Val Phe Thr Arg Asp Arg Lys Pro Lys Ala Ala His Ser Leu
    610                 615                 620
Arg Ala Arg Trp Thr Asn Gly Asp Lys Asn
625                 630

<210> SEQ ID NO 7
<211> LENGTH: 1839
<212> TYPE: DNA
<213> ORGANISM: Gibberella zeae

<400> SEQUENCE: 7
atgttgcgac cacaagccaa cagggctcgc gaccttgtgt cactagacgg tgtttggaac      60
tttgccctcg ccaaatctca cgacattgaa actgagcaag catggaagaa gcgaatctca     120
ccagagcttc aagtacctgt tccagccagc tacaacgaca tctttgctga cgagaccatc     180
cgcgaccacg tcggctgggt ctactatcag cgtcaagcag ttgttccccg cggttgggtt     240
gcgcctcagc gtgtctttct acgtgtagat gctgcaaccc accacggcag agtttacgtc     300
aacgacaagt ttgtcgtcga gcatatcggc ggctatacac cgtttgagat tgagcttact     360
ggacttgtcg aaccggggtc agagtttcgt cttacgattg ctgtgaacaa tcaactcaca     420
tgggagacta ttccgccggg tcgcattgag gctcaaagtg atggttcgcg gaagcagagc     480
tatcagcatg acttttttcaa ctatgctgga ttggcccgtt ctgtgtggct ttactcggta     540
ccaaaggtct ttataaatga tatcagcgtc ggcacagatc ttcttgggga cggaaccggc     600
attgtcgaat ttgatattcg gacctctggt gaacttcagg ctgacgcaag atggcgcatc     660
ctgctcgacg acgaagagga tgcgacagtg tgtcaagccc aagagtcaca tggaaaactt     720
gaggttaaaa acgctaaata ctgggcacct ggtgctgcgt accttttatca gcttcgggct     780
cagctcgtac gcggcgaaca cgacgagatc ctcgacacat ataaccttgc cgtaggcatc     840
cgttcagtcg agatccgaga tggccgcttc ttcatcaacg ggaagccatt ttattttacc     900
ggctttggca aacacgaaga tggccccgtc cgtggacgcg ttatgacgc gtcatacatg     960
atacacgact accgtctgat gaagtggata ggagccaact cttccgaac ctccccactac    1020
ccctacgcag aggaggttct ggaatatgcc gacagacacg gcgtggttgt tattaacgaa    1080
acagccgccg ttggtctcaa cctcaatatt gtctcgggta tgtttggcaa caagcaactt    1140
gccacattct ccccggatac catgagtagc aaaacacagg cttcacatga caagctatc     1200
cgtgagctta tcagccggga taagaaccac ccttgtgttg tgatgtggat gctggcaaat    1260
gagcctgggg ccagcgagca gggaagtcga gaatactttg aaccgctcgt taccttggcg    1320
cgatcgctgg acagtcagaa acggccaatg tgctactccc acatgatcca ctctaagcct    1380
gatacagatc gcatcgcaga cctttttgat gtagtctgta tgaaccgcta ctacgggtgg    1440
tacacgcaaa caggaaacct caaagccgca gaagtcgccc ttgaagccga gctacgcagt    1500
tggcaagaag cctacgccgc caaacccata atcatgacgg aatatggcac cgacacagtc    1560
gcaggtctgc acaccgtttg tgatgtgccc tggactgaag agtaccaggt tcgcttttg     1620
gacatgtatc accgcgtctt tgaccgcatt gataatgtcg tcggcgagca tgtgtggaac    1680
tttgctgatt tccagacatc ggctatgatt attagggttg atgggaacaa gaagggtatc    1740
```

-continued

```
tttactaggg atcgcaggcc aaagagtgca gctcatgctt tgcgagcgag atggactggg    1800
cctgttggac ctcgcaagat agaggtgacc aagcaataa                           1839
```

<210> SEQ ID NO 8
<211> LENGTH: 612
<212> TYPE: PRT
<213> ORGANISM: Gibberella zeae

<400> SEQUENCE: 8

```
Met Leu Arg Pro Gln Ala Asn Arg Ala Arg Asp Leu Val Ser Leu Asp
1               5                   10                  15

Gly Val Trp Asn Phe Ala Leu Ala Lys Ser His Asp Ile Glu Thr Glu
            20                  25                  30

Gln Ala Trp Lys Lys Arg Ile Ser Pro Glu Leu Gln Val Pro Val Pro
        35                  40                  45

Ala Ser Tyr Asn Asp Ile Phe Ala Asp Glu Thr Ile Arg Asp His Val
    50                  55                  60

Gly Trp Val Tyr Tyr Gln Arg Gln Ala Val Val Pro Arg Gly Trp Val
65                  70                  75                  80

Ala Pro Gln Arg Val Phe Leu Arg Val Asp Ala Ala Thr His His Gly
                85                  90                  95

Arg Val Tyr Val Asn Asp Lys Phe Val Val Glu His Ile Gly Gly Tyr
            100                 105                 110

Thr Pro Phe Glu Ile Glu Leu Thr Gly Leu Val Glu Pro Gly Ser Glu
        115                 120                 125

Phe Arg Leu Thr Ile Ala Val Asn Asn Gln Leu Thr Trp Glu Thr Ile
    130                 135                 140

Pro Pro Gly Arg Ile Glu Ala Gln Ser Asp Gly Ser Arg Lys Gln Ser
145                 150                 155                 160

Tyr Gln His Asp Phe Phe Asn Tyr Ala Gly Leu Ala Arg Ser Val Trp
                165                 170                 175

Leu Tyr Ser Val Pro Lys Val Phe Ile Asn Asp Ile Ser Val Gly Thr
            180                 185                 190

Asp Leu Leu Gly Asp Gly Thr Gly Ile Val Glu Phe Asp Ile Arg Thr
        195                 200                 205

Ser Gly Glu Leu Gln Ala Asp Ala Arg Trp Arg Ile Leu Leu Asp Asp
    210                 215                 220

Glu Glu Asp Ala Thr Val Cys Gln Ala Gln Glu Ser His Gly Lys Leu
225                 230                 235                 240

Glu Val Lys Asn Ala Lys Tyr Trp Ala Pro Gly Ala Ala Tyr Leu Tyr
                245                 250                 255

Gln Leu Arg Ala Gln Leu Val Arg Gly Glu His Asp Glu Ile Leu Asp
            260                 265                 270

Thr Tyr Asn Leu Ala Val Gly Ile Arg Ser Val Glu Ile Arg Asp Gly
        275                 280                 285

Arg Phe Phe Ile Asn Gly Lys Pro Phe Tyr Phe Thr Gly Phe Gly Lys
    290                 295                 300

His Glu Asp Gly Pro Val Arg Gly Arg Gly Tyr Asp Ala Ser Tyr Met
305                 310                 315                 320

Ile His Asp Tyr Arg Leu Met Lys Trp Ile Gly Ala Asn Ser Phe Arg
                325                 330                 335

Thr Ser His Tyr Pro Tyr Ala Glu Glu Val Leu Glu Tyr Ala Asp Arg
            340                 345                 350
```

-continued

```
His Gly Val Val Ile Asn Glu Thr Ala Ala Val Gly Leu Asn Leu
        355                 360                 365

Asn Ile Val Ser Gly Met Phe Gly Asn Lys Gln Leu Ala Thr Phe Ser
    370                 375                 380

Pro Asp Thr Met Ser Ser Lys Thr Gln Ala Ser His Glu Gln Ala Ile
385                 390                 395                 400

Arg Glu Leu Ile Ser Arg Asp Lys Asn His Pro Cys Val Val Met Trp
                405                 410                 415

Met Leu Ala Asn Glu Pro Gly Ala Ser Glu Gln Gly Ser Arg Glu Tyr
            420                 425                 430

Phe Glu Pro Leu Val Thr Leu Ala Arg Ser Leu Asp Ser Gln Lys Arg
        435                 440                 445

Pro Met Cys Tyr Ser His Met Ile His Ser Lys Pro Asp Thr Asp Arg
    450                 455                 460

Ile Ala Asp Leu Phe Asp Val Val Cys Met Asn Arg Tyr Tyr Gly Trp
465                 470                 475                 480

Tyr Thr Gln Thr Gly Asn Leu Lys Ala Ala Glu Val Ala Leu Glu Ala
                485                 490                 495

Glu Leu Arg Ser Trp Gln Glu Ala Tyr Ala Ala Lys Pro Ile Ile Met
            500                 505                 510

Thr Glu Tyr Gly Thr Asp Thr Val Ala Gly Leu His Thr Val Cys Asp
        515                 520                 525

Val Pro Trp Thr Glu Glu Tyr Gln Val Arg Phe Leu Asp Met Tyr His
    530                 535                 540

Arg Val Phe Asp Arg Ile Asp Asn Val Val Gly Glu His Val Trp Asn
545                 550                 555                 560

Phe Ala Asp Phe Gln Thr Ser Ala Met Ile Ile Arg Val Asp Gly Asn
                565                 570                 575

Lys Lys Gly Ile Phe Thr Arg Asp Arg Arg Pro Lys Ser Ala Ala His
            580                 585                 590

Ala Leu Arg Ala Arg Trp Thr Gly Pro Val Gly Pro Arg Lys Ile Glu
        595                 600                 605

Val Thr Lys Gln
    610
```

<210> SEQ ID NO 9
<211> LENGTH: 1935
<212> TYPE: DNA
<213> ORGANISM: Aspergillus nidulans

<400> SEQUENCE: 9

| | | | | |
|---|---|---|---|---|
| atgagggtct | tcccagtgtt | atctttcttg | tcactcgcac | tcatccctcc ctcgctcggc | 60 |
| gtcccgtcgc | tcagctccg | cgacgtcgag | ctcccgccaa | cacaacaagc cctaaccatc | 120 |
| aacctgaaac | cccagcagac | gtcgacgaga | gacctcgttt | ctctcgacgg gctgtggtcc | 180 |
| tttgccctcg | aagacgccac | aaacagcacc | tctgctccct | ggacggcggc gctcccaaag | 240 |
| ggcctggaat | gtcccgtccc | tgcatcctac | aacgacatct | tcgtcgacag gaccattcac | 300 |
| gatcacgtcg | gctgggtata | ctaccaacgc | actgtgactg | tcccacgggg ctgggcagat | 360 |
| cagcgcgctt | tcctccgtct | ggagtcagca | acgcatcatg | ccgcgtcta tgtcaatgag | 420 |
| cacctggttg | ccgagcatgt | tggcggttac | accccgtttg | aagccgacat acctctctc | 480 |
| gtgcagcctg | gtgaaagctt | ccggttgaca | atcggtgtgg | acaaccagct gacgcacgag | 540 |
| accatccctc | caggtgatct | ggtgacttct | gagtatacag | ggaagaaaca gcagagctac | 600 |

```
cagcacgact tttacaatta cgcagggctg gcgaggtcca tatggctcta ctctgtgccc    660
aaggatcagt tcatcaagga catcacggtc gttccagatg ttgattggga tggtgacgca    720
gagaccggag tggtgagcta taccgtccag acttctaacg cgacgagtgg ccccatccgg    780
atctcaattc tcgatgaaga aggaaacgag gtcgcaacag cgtccggagc cactgggaca    840
gctaccattc cctctgtcaa cctctggcag cctggcgctc cctacctata ctccttcact    900
gtcagcatcc tctccgcctc ccaacggctg atcgacacat acacactgcc catcggtatc    960
cgcactgtgg ctgtcggcaa cggcactatc ctggtcaaca atgagccggt ctacctgacc   1020
gggtttggca aacacgagga tagtcccatc cgcggcaaag ccacgacat cgcgtaccta    1080 gtccacgact tccagctgct ggactggatc ggcgcgaact ctttccgcac cagccactat   1140
ccttacgcgg aagaggtgat ggaatttgca gaccgccagg gaattcttgt cattgacgaa   1200
acgcccgccg tcggactggc gtacagcatt ggcgcgggca tctcaacgga cacaagcagg   1260
gtgaccttcg cgccggacgg gatcaacaac aatactcgcg cagcccacgc ccaggctctc   1320
cgggaactca ttgcacggga caagaaccac cccagcgtta tcatgtggtc gatcgcgaac   1380
gaacccgcgt ctgatgagcc aggtgcgcgc gcatactttg agcccctcac gcggctcgcc   1440 cgctcccctcg atcccgcgca ccggcccata actttcgcca acctcggcct ggcaacctat   1500
gaaaccgaca caatctctga cttgttcgat gttctctgcc tgaaccgata tttcggctgg   1560
tactcgtaca cgggagacct ggagtccgcc ggaaaggcac tccatgagga actggacgga   1620
tgggtggcca agtacccgac caaaccaatc atcatcagcg agtacggggc agacacaatg   1680
gcgggactgc actctgtgct gggactgatc tggagcgagg agttccaaat cgagttgctg   1740
gatgtgtatc atggggtgtt cgaccagttc cagaatgtgg ttggtgagca tgtatggaat   1800 tcgcggatt tccaaacaaa ggagggcata cagcgggtgg atgggaacaa gaagggtgtc   1860
tttaccagag accgcagacc caaggggggcg gcgtttgcct tgaggaagag gtggatgaat   1920
atgatgtcga gttag                                                   1935
```

<210> SEQ ID NO 10
<211> LENGTH: 644
<212> TYPE: PRT
<213> ORGANISM: Aspergillus nidulans

<400> SEQUENCE: 10

```
Met Arg Val Phe Pro Val Leu Ser Phe Leu Ser Leu Ala Leu Ile Pro
 1               5                  10                  15

Pro Ser Leu Gly Val Pro Ser Pro Gln Leu Arg Asp Val Glu Leu Pro
            20                  25                  30

Pro Thr Gln Ala Leu Thr Ile Asn Leu Lys Pro Gln Gln Thr Ser
        35                  40                  45

Thr Arg Asp Leu Val Ser Leu Asp Gly Leu Trp Ser Phe Ala Leu Glu
    50                  55                  60

Asp Ala Thr Asn Ser Thr Ser Ala Pro Trp Thr Ala Ala Leu Pro Lys
65                  70                  75                  80

Gly Leu Glu Cys Pro Val Pro Ala Ser Tyr Asn Asp Ile Phe Val Asp
                85                  90                  95

Arg Thr Ile His Asp His Val Gly Trp Val Tyr Tyr Gln Arg Thr Val
               100                 105                 110

Thr Val Pro Arg Gly Trp Ala Asp Gln Arg Ala Phe Leu Arg Leu Glu
           115                 120                 125
```

-continued

```
Ser Ala Thr His His Gly Arg Val Tyr Val Asn Glu His Leu Val Ala
    130                 135                 140
Glu His Val Gly Gly Tyr Thr Pro Phe Glu Ala Asp Ile Thr Ser Leu
145                 150                 155                 160
Val Gln Pro Gly Glu Ser Phe Arg Leu Thr Ile Gly Val Asp Asn Gln
                165                 170                 175
Leu Thr His Glu Thr Ile Pro Pro Gly Asp Leu Val Thr Ser Glu Tyr
            180                 185                 190
Thr Gly Lys Lys Gln Gln Ser Tyr Gln His Asp Phe Tyr Asn Tyr Ala
        195                 200                 205
Gly Leu Ala Arg Ser Ile Trp Leu Tyr Ser Val Pro Lys Asp Gln Phe
    210                 215                 220
Ile Lys Asp Ile Thr Val Val Pro Asp Val Asp Trp Asp Gly Asp Ala
225                 230                 235                 240
Glu Thr Gly Val Val Ser Tyr Thr Val Gln Thr Ser Asn Ala Thr Ser
                245                 250                 255
Gly Pro Ile Arg Ile Ser Ile Leu Asp Glu Gly Asn Glu Val Ala
            260                 265                 270
Thr Ala Ser Gly Ala Thr Gly Thr Ala Thr Ile Pro Ser Val Asn Leu
        275                 280                 285
Trp Gln Pro Gly Ala Pro Tyr Leu Tyr Ser Phe Thr Val Ser Ile Leu
    290                 295                 300
Ser Ala Ser Gln Arg Leu Ile Asp Thr Tyr Thr Leu Pro Ile Gly Ile
305                 310                 315                 320
Arg Thr Val Ala Val Gly Asn Gly Thr Ile Leu Val Asn Asn Glu Pro
                325                 330                 335
Val Tyr Leu Thr Gly Phe Gly Lys His Glu Asp Ser Pro Ile Arg Gly
            340                 345                 350
Lys Gly His Asp Ile Ala Tyr Leu Val His Asp Phe Gln Leu Leu Asp
        355                 360                 365
Trp Ile Gly Ala Asn Ser Phe Arg Thr Ser His Tyr Pro Tyr Ala Glu
    370                 375                 380
Glu Val Met Glu Phe Ala Asp Arg Gln Gly Ile Leu Val Ile Asp Glu
385                 390                 395                 400
Thr Pro Ala Val Gly Leu Ala Tyr Ser Ile Gly Ala Gly Ile Ser Thr
                405                 410                 415
Asp Thr Ser Arg Val Thr Phe Ala Pro Asp Gly Ile Asn Asn Asn Thr
            420                 425                 430
Arg Ala Ala His Ala Gln Ala Leu Arg Glu Leu Ile Ala Arg Asp Lys
        435                 440                 445
Asn His Pro Ser Val Ile Met Trp Ser Ile Ala Asn Glu Pro Ala Ser
    450                 455                 460
Asp Glu Pro Gly Ala Arg Ala Tyr Phe Glu Pro Leu Thr Arg Leu Ala
465                 470                 475                 480
Arg Ser Leu Asp Pro Ala His Arg Pro Ile Thr Phe Ala Asn Leu Gly
                485                 490                 495
Leu Ala Thr Tyr Glu Thr Asp Thr Ile Ser Asp Leu Phe Asp Val Leu
            500                 505                 510
Cys Leu Asn Arg Tyr Phe Gly Trp Tyr Ser Tyr Thr Gly Asp Leu Glu
        515                 520                 525
Ser Ala Gly Lys Ala Leu His Glu Glu Leu Asp Gly Trp Val Ala Lys
    530                 535                 540
```

-continued

Tyr Pro Thr Lys Pro Ile Ile Ser Glu Tyr Gly Ala Asp Thr Met
545                 550                 555                 560

Ala Gly Leu His Ser Val Leu Gly Leu Ile Trp Ser Glu Glu Phe Gln
            565                 570                 575

Ile Glu Leu Leu Asp Val Tyr His Gly Val Phe Asp Gln Phe Gln Asn
            580                 585                 590

Val Val Gly Glu His Val Trp Asn Phe Ala Asp Phe Gln Thr Lys Glu
        595                 600                 605

Gly Ile Gln Arg Val Asp Gly Asn Lys Lys Gly Val Phe Thr Arg Asp
        610                 615                 620

Arg Arg Pro Lys Gly Ala Ala Phe Ala Leu Arg Lys Arg Trp Met Asn
625                 630                 635                 640

Met Met Ser Ser

<210> SEQ ID NO 11
<211> LENGTH: 628
<212> TYPE: PRT
<213> ORGANISM: Caenorhabditis elegans

<400> SEQUENCE: 11

Met Ile Leu Lys Pro Thr Val Leu Leu Leu Leu Leu Gln Ser Ile
1               5                   10                  15

Ser Thr Ile Thr Cys Leu Leu His Val Gln Lys Asn Glu Ile Arg Thr
            20                  25                  30

Val Asp Ser Leu Asp Gly Leu Trp Thr Phe Val Arg Glu Pro His Asn
        35                  40                  45

Gly Gly Asp Val Gly Ile Val Asn Gln Trp Asn Thr Leu Asp Leu Glu
    50                  55                  60

Arg Phe Gln Asn Ala Thr Val Met Pro Val Pro Ser Ala Tyr Asn Asp
65                  70                  75                  80

Leu Gly Thr Gly Ser Glu Leu Arg Asp His Ile Gly Trp Val Trp Tyr
                85                  90                  95

Glu Lys Lys Glu Phe Val Pro Leu Arg Asp Arg Asn Met Arg His Val
            100                 105                 110

Leu Arg Phe Gly Ser Val Asn Tyr Phe Ala Val Val Tyr Ile Asn Ser
        115                 120                 125

Glu Lys Val Thr Ser His Ile Gly Gly His Leu Pro Phe Glu Val Asp
    130                 135                 140

Ile Ser Ala Gln Ile Lys Phe Gly Ala Glu Asn Lys Phe Thr Val Ala
145                 150                 155                 160

Val Asn Asn Thr Leu Ser Trp Ser Thr Ile Pro Gln Gly Asp Phe Asn
                165                 170                 175

Tyr Gln Ser Val Ala Pro Arg Asn Ile Ser Gly Arg Ile Leu Ser Arg
            180                 185                 190

Leu Pro Ala Gly Ala Val Lys Asn Val Gly Asn Phe Asp Phe Phe Asn
        195                 200                 205

Tyr Ala Gly Ile Leu Arg Ser Val Gln Leu Met Lys Ile Pro Ser Val
    210                 215                 220

Tyr Ile Gln Asn Ile Asn Ile Val Ala Asp His Thr Gly Ser Phe Phe
225                 230                 235                 240

Phe Glu Thr Ala Val Ser Ser Leu Asp Gly Val Arg Val Glu Val Lys
                245                 250                 255

```
Met Phe Asp Gly Glu Gly Ser Leu Val Tyr Thr Gly Asn Gln Thr Lys
            260                 265                 270

Ser Glu Gly Gln Ile Ser Asn Pro Lys Leu Trp Trp Pro Arg Gly Met
        275                 280                 285

Gly Lys Pro Asp Leu Tyr Ser Leu Glu Val Ser Leu Ile Leu Asp Gly
    290                 295                 300

Glu Leu Ala Asp Ile Tyr Arg Glu Gln Phe Gly Phe Arg Thr Val Thr
305                 310                 315                 320

Trp Ser Asp Ser Gln Ile Phe Ile Asn Ser Lys Pro Phe Tyr Cys Leu
                325                 330                 335

Gly Phe Gly Met His Glu Asp Phe Glu Ile Ile Gly Arg Gly Phe Asn
            340                 345                 350

Gln Ala Ile Met Thr Lys Asp Leu Asn Leu Leu Glu Trp Met Gly Gly
            355                 360                 365

Asn Cys Tyr Arg Thr Thr His Tyr Pro Tyr Ser Glu Glu Arg Met Phe
370                 375                 380

Glu Asn Asp Arg Arg Gly Ile Ala Val Ile Val Glu Thr Pro Ala Val
385                 390                 395                 400

Gly Leu Lys Gly Phe Ser Lys Ala Asn Asn Asn Leu His Val Lys Met
                405                 410                 415

Leu Gln Asp Met Ile Asp Arg Asp Lys Asn His Pro Ser Val Ile Ala
            420                 425                 430

Trp Ser Leu Ala Asn Glu Pro Gln Thr Met Lys Lys Glu Ser Arg Asn
            435                 440                 445

Tyr Phe Lys Thr Leu Val Asp Thr Ala His Gly Ile Asp Arg Thr Arg
        450                 455                 460

Pro Val Thr Thr Val Tyr Gly Pro Thr Asn Phe Asp Asn Asp Gln Thr
465                 470                 475                 480

Ala Asp Leu Met Asp Phe Ile Cys Val Asn Arg Tyr Tyr Gly Trp Tyr
                485                 490                 495

Ile Asp Met Gly Tyr Ile Pro Trp Ile Asn Gln Ser Val Tyr Trp Asp
            500                 505                 510

Ile Ser Leu Trp Arg Glu Thr Phe His Lys Pro Ile Ile Val Thr Glu
        515                 520                 525

Tyr Gly Ala Asp Ser Ile Pro Gly Leu Asn Gln Glu Pro Ser Val Asp
    530                 535                 540

Phe Ser Glu Gln Tyr Gln Asn Glu Val Ile Gln Glu Thr His His Ala
545                 550                 555                 560

Phe Asp Ala Leu Val Lys Asp His Thr Ile Thr Gly Glu Met Ile Trp
                565                 570                 575

Asn Phe Ala Asp Phe Met Thr Gly Met Thr Thr Thr Arg Ala Val Gly
            580                 585                 590

Asn His Lys Gly Val Phe Thr Arg Ser Arg Gln Ala Lys Ile Ala Ala
        595                 600                 605

Tyr Thr Leu Arg Asn Arg Tyr Leu Lys Lys Gly Ser Asn Ile Asp Thr
    610                 615                 620

Thr Ile Trp Thr
625

<210> SEQ ID NO 12
<211> LENGTH: 670
<212> TYPE: PRT
<213> ORGANISM: Drosophila melanogaster
```

-continued

<400> SEQUENCE: 12

```
Met His Leu Arg Ile Arg Leu Thr Cys Arg Lys Tyr Glu Ile Trp Ala
1               5                   10                  15

Leu Ser Ile Phe Ser Leu Val Thr Gly Leu Tyr Val Leu His Phe Ser
            20                  25                  30

Ile Ala Leu Ile Leu Val Asn Lys Glu Val Pro Gln Thr Arg Gly Met
        35                  40                  45

Leu Tyr Pro Arg Glu Ser Glu Thr Arg Glu Val Arg Ser Leu Asp Gly
    50                  55                  60

Ile Trp Asn Phe Val Arg Ser Asp Gln Ala Asn Pro Thr Gln Gly Val
65                  70                  75                  80

Arg Asp Glu Trp Tyr Ala Lys Glu Leu Ser Lys Ser Arg Pro Thr Ile
                85                  90                  95

Pro Met Pro Val Pro Ala Ser Tyr Asn Asp Ile Thr Thr Asp Asn Leu
            100                 105                 110

Arg Asp His Val Gly Thr Val Trp Tyr Asp Arg Lys Phe Phe Val Pro
        115                 120                 125

Arg Ser Trp Ser Lys Asp Gln Arg Ile Trp Leu Arg Phe Gly Ser Val
    130                 135                 140

His Tyr Glu Ala Tyr Val Trp Ile Asn Gly Gln Lys Val Val Lys His
145                 150                 155                 160

Glu Met Gly His Leu Pro Phe Glu Ala Glu Val Thr Asp Leu Leu Ser
                165                 170                 175

Tyr Gly Ala Glu Asn Arg Ile Thr Val Met Cys Asp Asn Ala Leu Ile
            180                 185                 190

Gln Thr Thr Val Pro Gln Gly Arg Ile Thr Glu Val Pro Asn Asp Gly
        195                 200                 205

Gly Met Thr Ile Val Gln Ser Tyr Thr Phe Asp Phe Asn Tyr Ala
    210                 215                 220

Gly Ile His Arg Ser Val His Leu Tyr Thr Thr Pro Arg Thr Phe Ile
225                 230                 235                 240

Glu Glu Val Glu Val Thr Thr Asn Leu Ser Lys Asp Ala Thr Val Gly
                245                 250                 255

Glu Val Phe Tyr Ser Val Ser Val Asn Gly Ser Ala Ala Asn Glu Ala
            260                 265                 270

Asp Asn Val Leu Gln Ile Gln Ala Asn Leu Tyr Asp Lys Asp Gly Ile
        275                 280                 285

Leu Val Ala Asn Ala Thr Ser Asp Gln Lys Leu Gly Gly Lys Leu Gln
    290                 295                 300

Val Asn Pro Val Lys Pro Trp Trp Pro Tyr Leu Met His Ser Glu Pro
305                 310                 315                 320

Gly Tyr Leu Tyr Gln Leu Glu Ile Lys Leu Leu Ala Thr Asn Asp Glu
                325                 330                 335

Leu Leu Asp Val Tyr Arg Leu Lys Val Gly Ile Arg Thr Leu Ser Trp
            340                 345                 350

Asn Ser Gln Gln Phe Leu Ile Asn Gly Lys Pro Val Tyr Phe Arg Gly
        355                 360                 365

Phe Gly Arg His Glu Asp Ser Asp Ile Arg Gly Lys Gly Leu Asp Asn
    370                 375                 380

Ala Leu Met Val Arg Asp Phe Asn Leu Leu Lys Trp Ile Gly Ala Asn
385                 390                 395                 400

Ala Tyr Arg Thr Ser His Tyr Pro Tyr Ser Glu Glu Ser Met Gln Phe
                405                 410                 415
```

```
Ala Asp Glu His Gly Ile Met Ile Ile Asp Glu Cys Pro Ser Val Asp
            420                 425                 430

Thr Glu Asn Phe Ser Gln Glu Leu Leu Gly Lys His Lys Ser Ser Leu
        435                 440                 445

Glu Gln Leu Ile His Arg Asp Arg Asn His Pro Ser Val Val Met Trp
    450                 455                 460

Ser Ile Ala Asn Glu Pro Arg Thr Gly Ser Val Ser Ala Asp Ser Tyr
465                 470                 475                 480

Phe Glu Leu Val Ala Asn Phe Thr Arg Ser Leu Asp Lys Thr Arg Pro
                485                 490                 495

Ile Thr Ala Ala Ile Ala Val Ser Asn Thr Gln Asp Lys Ala Gly Arg
                    500                 505                 510

Ser Leu Asp Ile Ile Ser Phe Asn Arg Tyr Asn Ala Trp Tyr Ser Asn
            515                 520                 525

Ala Gly Arg Leu Asp Met Ile Thr Gln Asn Val Ile Asp Glu Ala Ile
    530                 535                 540

Ala Trp Asn Lys Arg Tyr Asn Lys Pro Ile Ile Met Ser Glu Tyr Gly
545                 550                 555                 560

Ala Asp Thr Leu Glu Gly Leu His Met Gln Pro Ala Tyr Val Trp Ser
                565                 570                 575

Glu Glu Phe Gln Thr Glu Val Phe Ser Arg His Phe Lys Ala Phe Asp
            580                 585                 590

Glu Leu Arg Lys Lys Gly Trp Phe Ile Gly Glu Phe Val Trp Asn Phe
        595                 600                 605

Ala Asp Phe Lys Thr Ala Gln Ser Tyr Thr Arg Val Gly Gly Asn Lys
    610                 615                 620

Lys Gly Val Phe Thr Arg Ala Arg Gln Pro Lys Ala Ala His Leu
625                 630                 635                 640

Leu Arg Lys Arg Tyr Phe Ala Leu Gly Arg Asp Leu Asp Gln Cys Ser
                645                 650                 655

Phe Pro Glu Asp Leu Phe Thr Tyr Ile Ala Asp Leu Ile Ser
                660                 665                 670

<210> SEQ ID NO 13
<211> LENGTH: 648
<212> TYPE: PRT
<213> ORGANISM: Mus musculus

<400> SEQUENCE: 13

Met Ser Leu Lys Trp Ser Ala Cys Trp Val Ala Leu Gly Gln Leu Leu
1               5                   10                  15

Cys Ser Cys Ala Leu Ala Leu Lys Gly Gly Met Leu Phe Pro Lys Glu
            20                  25                  30

Ser Pro Ser Arg Glu Leu Lys Ala Leu Asp Gly Leu Trp His Phe Arg
        35                  40                  45

Ala Asp Leu Ser Asn Asn Arg Leu Gln Gly Phe Glu Gln Gln Trp Tyr
    50                  55                  60

Arg Gln Pro Leu Arg Glu Ser Gly Pro Val Leu Asp Met Pro Val Pro
65                  70                  75                  80

Ser Ser Phe Asn Asp Ile Thr Gln Glu Ala Ala Leu Arg Asp Phe Ile
                85                  90                  95

Gly Trp Val Trp Tyr Glu Arg Glu Ala Ile Leu Pro Arg Arg Trp Thr
                100                 105                 110

Gln Asp Thr Asp Met Arg Val Val Leu Arg Ile Asn Ser Ala His Tyr
        115                 120                 125
```

-continued

Tyr Ala Val Val Trp Val Asn Gly Ile His Val Val Glu His Glu Gly
130                 135                 140

Gly His Leu Pro Phe Glu Ala Asp Ile Ser Lys Leu Val Gln Ser Gly
145                 150                 155                 160

Pro Leu Thr Thr Cys Arg Ile Thr Ile Ala Ile Asn Asn Thr Leu Thr
                165                 170                 175

Pro His Thr Leu Pro Pro Gly Thr Ile Val Tyr Lys Thr Asp Thr Ser
            180                 185                 190

Met Tyr Pro Lys Gly Tyr Phe Val Gln Asp Thr Ser Phe Asp Phe Phe
        195                 200                 205

Asn Tyr Ala Gly Leu His Arg Ser Val Val Leu Tyr Thr Thr Pro Thr
210                 215                 220

Thr Tyr Ile Asp Asp Ile Thr Val Ile Thr Asn Val Glu Gln Asp Ile
225                 230                 235                 240

Gly Leu Val Thr Tyr Trp Ile Ser Val Gln Gly Ser Glu His Phe Gln
                245                 250                 255

Leu Glu Val Gln Leu Leu Asp Glu Asp Gly Lys Val Val Ala His Gly
            260                 265                 270

Thr Gly Asn Gln Gly Gln Leu Gln Val Pro Ser Ala Asn Leu Trp Trp
        275                 280                 285

Pro Tyr Leu Met His Glu His Pro Ala Tyr Met Tyr Ser Leu Glu Val
290                 295                 300

Lys Val Thr Thr Thr Glu Ser Val Thr Asp Tyr Tyr Thr Leu Pro Val
305                 310                 315                 320

Gly Ile Arg Thr Val Ala Val Thr Lys Ser Lys Phe Leu Ile Asn Gly
                325                 330                 335

Lys Pro Phe Tyr Phe Gln Gly Val Asn Lys His Glu Asp Ser Asp Ile
            340                 345                 350

Arg Gly Lys Gly Phe Asp Trp Pro Leu Leu Val Lys Asp Phe Asn Leu
        355                 360                 365

Leu Arg Trp Leu Gly Ala Asn Ser Phe Arg Thr Ser His Tyr Pro Tyr
370                 375                 380

Ser Glu Glu Val Leu Gln Leu Cys Asp Arg Tyr Gly Ile Val Val Ile
385                 390                 395                 400

Asp Glu Cys Pro Gly Val Gly Ile Val Leu Pro Gln Ser Phe Gly Asn
                405                 410                 415

Glu Ser Leu Arg His His Leu Glu Val Met Glu Glu Leu Val Arg Arg
            420                 425                 430

Asp Lys Asn His Pro Ala Val Val Met Trp Ser Val Ala Asn Glu Pro
        435                 440                 445

Ser Ser Ala Leu Lys Pro Ala Ala Tyr Tyr Phe Lys Thr Leu Ile Thr
450                 455                 460

His Thr Lys Ala Leu Asp Leu Thr Arg Pro Val Thr Phe Val Ser Asn
465                 470                 475                 480

Ala Lys Tyr Asp Ala Asp Leu Gly Ala Pro Tyr Val Asp Val Ile Cys
                485                 490                 495

Val Asn Ser Tyr Phe Ser Trp Tyr His Asp Tyr Gly His Leu Glu Val
            500                 505                 510

Ile Gln Pro Gln Leu Asn Ser Gln Phe Glu Asn Trp Tyr Lys Thr His
        515                 520                 525

Gln Lys Pro Ile Ile Gln Ser Glu Tyr Gly Ala Asp Ala Ile Pro Gly
530                 535                 540

-continued

```
Ile His Glu Asp Pro Pro Arg Met Phe Ser Glu Glu Tyr Gln Lys Ala
545                 550                 555                 560

Val Leu Glu Asn Tyr His Ser Val Leu Asp Gln Lys Arg Lys Glu Tyr
                565                 570                 575

Val Val Gly Glu Leu Ile Trp Asn Phe Ala Asp Phe Met Thr Asn Gln
            580                 585                 590

Ser Pro Leu Arg Val Ile Gly Asn Lys Lys Gly Ile Phe Thr Arg Gln
        595                 600                 605

Arg Gln Pro Lys Thr Ser Ala Phe Ile Leu Arg Glu Arg Tyr Trp Arg
    610                 615                 620

Ile Ala Asn Glu Thr Gly Gly His Gly Ser Gly Pro Arg Thr Gln Cys
625                 630                 635                 640

Phe Gly Ser Arg Pro Phe Thr Phe
                645
```

<210> SEQ ID NO 14
<211> LENGTH: 648
<212> TYPE: PRT
<213> ORGANISM: Rattus norvegicus

<400> SEQUENCE: 14

```
Met Ser Pro Arg Arg Ser Val Cys Trp Phe Val Leu Gly Gln Leu Leu
1               5                   10                  15

Cys Ser Cys Ala Val Ala Leu Gln Gly Gly Met Leu Phe Pro Lys Glu
            20                  25                  30

Thr Pro Ser Arg Glu Leu Lys Val Leu Asp Gly Leu Trp Ser Phe Arg
        35                  40                  45

Ala Asp Tyr Ser Asn Asn Arg Leu Gln Gly Phe Glu Lys Gln Trp Tyr
    50                  55                  60

Arg Gln Pro Leu Arg Glu Ser Gly Pro Thr Leu Asp Met Pro Val Pro
65                  70                  75                  80

Ser Ser Phe Asn Asp Ile Thr Gln Glu Ala Glu Leu Arg Asn Phe Ile
                85                  90                  95

Gly Trp Val Trp Tyr Glu Arg Glu Ala Val Leu Pro Gln Arg Trp Thr
            100                 105                 110

Gln Asp Thr Asp Arg Arg Val Val Leu Arg Ile Asn Ser Ala His Tyr
        115                 120                 125

Tyr Ala Val Val Trp Val Asn Gly Ile His Val Val Glu His Glu Gly
    130                 135                 140

Gly His Leu Pro Phe Glu Ala Asp Ile Thr Lys Leu Val Gln Ser Gly
145                 150                 155                 160

Pro Leu Thr Thr Phe Arg Val Thr Ile Ala Ile Asn Asn Thr Leu Thr
                165                 170                 175

Pro Tyr Thr Leu Pro Pro Gly Thr Ile Val Tyr Lys Thr Asp Pro Ser
            180                 185                 190

Met Tyr Pro Lys Gly Tyr Phe Val Gln Asp Ile Ser Phe Asp Phe Phe
        195                 200                 205

Asn Tyr Ala Gly Leu His Arg Ser Val Val Leu Tyr Thr Thr Pro Thr
    210                 215                 220

Thr Tyr Ile Asp Asp Ile Thr Val Thr Thr Asp Val Asp Arg Asp Val
225                 230                 235                 240

Gly Leu Val Asn Tyr Trp Ile Ser Val Gln Gly Ser Asp His Phe Gln
                245                 250                 255

Leu Glu Val Arg Leu Leu Asp Glu Asp Gly Lys Ile Val Ala Arg Gly
            260                 265                 270
```

```
Thr Gly Asn Glu Gly Gln Leu Lys Val Pro Arg Ala His Leu Trp Trp
            275                 280                 285

Pro Tyr Leu Met His Glu His Pro Ala Tyr Leu Tyr Ser Leu Glu Val
        290                 295                 300

Thr Met Thr Thr Pro Glu Ser Val Ser Asp Phe Tyr Thr Leu Pro Val
305                 310                 315                 320

Gly Ile Arg Thr Val Ala Val Thr Lys Ser Lys Phe Leu Ile Asn Gly
                325                 330                 335

Lys Pro Phe Tyr Phe Gln Gly Val Asn Lys His Glu Asp Ser Asp Ile
            340                 345                 350

Arg Gly Arg Gly Phe Asp Trp Pro Leu Leu Ile Lys Asp Phe Asn Leu
        355                 360                 365

Leu Arg Trp Leu Gly Ala Asn Ser Phe Arg Thr Ser His Tyr Pro Tyr
    370                 375                 380

Ser Glu Glu Val Leu Gln Leu Cys Asp Arg Tyr Gly Ile Val Val Ile
385                 390                 395                 400

Asp Glu Cys Pro Gly Val Gly Ile Val Leu Pro Gln Ser Phe Gly Asn
                405                 410                 415

Val Ser Leu Arg His His Leu Glu Val Met Asp Glu Leu Val Arg Arg
            420                 425                 430

Asp Lys Asn His Pro Ala Val Val Met Trp Ser Val Ala Asn Glu Pro
        435                 440                 445

Val Ser Ser Leu Lys Pro Ala Gly Tyr Tyr Phe Lys Thr Leu Ile Ala
    450                 455                 460

His Thr Lys Ala Leu Asp Pro Thr Arg Pro Val Thr Phe Val Ser Asn
465                 470                 475                 480

Thr Arg Tyr Asp Ala Asp Met Gly Ala Pro Tyr Val Asp Val Ile Cys
                485                 490                 495

Val Asn Ser Tyr Leu Ser Trp Tyr His Asp Tyr Gly His Leu Glu Val
            500                 505                 510

Ile Gln Leu Gln Leu Thr Ser Gln Phe Glu Asn Trp Tyr Lys Met Tyr
        515                 520                 525

Gln Lys Pro Ile Ile Gln Ser Glu Tyr Gly Ala Asp Ala Val Ser Gly
    530                 535                 540

Leu His Glu Asp Pro Pro Arg Met Phe Ser Glu Glu Tyr Gln Thr Ala
545                 550                 555                 560

Leu Leu Glu Asn Tyr His Leu Ile Leu Asp Glu Lys Arg Lys Glu Tyr
                565                 570                 575

Val Ile Gly Glu Leu Ile Trp Asn Phe Ala Asp Phe Met Thr Asn Gln
            580                 585                 590

Ser Pro Leu Arg Val Thr Gly Asn Lys Lys Gly Ile Phe Thr Arg Gln
        595                 600                 605

Arg Asn Pro Lys Met Ala Ala Phe Ile Leu Arg Glu Arg Tyr Trp Arg
    610                 615                 620

Ile Ala Asn Glu Thr Arg Gly Tyr Gly Ser Val Pro Arg Thr Gln Cys
625                 630                 635                 640

Met Gly Ser Arg Pro Phe Thr Phe
                645

<210> SEQ ID NO 15
<211> LENGTH: 651
<212> TYPE: PRT
<213> ORGANISM: Felis catus
```

<400> SEQUENCE: 15

```
Met Leu Arg Gly Pro Ala Ala Val Trp Ala Ala Leu Gly Pro Leu Leu
1               5                   10                  15

Trp Ala Cys Gly Leu Ala Leu Arg Gly Gly Met Leu Tyr Pro Arg Glu
            20                  25                  30

Ser Pro Ser Arg Glu Arg Lys Glu Leu Asn Gly Leu Trp Ser Phe Arg
        35                  40                  45

Ala Asp Phe Ser Glu Asn Arg Arg Gln Gly Phe Glu Gln Gln Trp Tyr
    50                  55                  60

Arg Thr Pro Leu Arg Glu Ser Gly Pro Thr Leu Asp Met Pro Val Pro
65                  70                  75                  80

Ser Ser Phe Asn Asp Val Gly Gln Asp Arg Gln Leu Arg Ser Phe Val
                85                  90                  95

Gly Trp Val Trp Tyr Glu Arg Glu Ala Thr Leu Pro Gln Arg Trp Thr
            100                 105                 110

Gln Asp Leu Gly Thr Arg Val Val Leu Arg Ile Gly Ser Ala His Tyr
        115                 120                 125

Tyr Ala Ile Val Trp Val Asn Gly Val His Val Ala Glu His Glu Gly
    130                 135                 140

Gly His Leu Pro Phe Glu Ala Asp Ile Ser Lys Leu Val Gln Ser Gly
145                 150                 155                 160

Pro Leu Ala Ser Cys Arg Ile Thr Ile Ala Ile Asn Asn Thr Leu Thr
                165                 170                 175

Pro His Thr Leu Pro Pro Gly Thr Ile Leu Tyr Gln Thr Asp Thr Ser
            180                 185                 190

Lys Tyr Pro Lys Gly Tyr Phe Val Gln Asn Ile Asn Phe Asp Phe Phe
        195                 200                 205

Asn Tyr Ala Gly Leu His Arg Pro Val Leu Leu Tyr Thr Thr Pro Thr
    210                 215                 220

Thr Tyr Ile Asp Asp Ile Thr Ile Ser Thr Ser Val Asn Gln Asp Thr
225                 230                 235                 240

Gly Leu Val Asp Tyr Gln Ile Phe Val Glu Gly Gly Glu His Phe Gln
                245                 250                 255

Leu Glu Val Arg Leu Leu Asp Glu Glu Gly Lys Val Val Ala Gln Gly
            260                 265                 270

Thr Gly Gly Arg Gly Gln Leu Gln Val Pro Asn Ala His Leu Trp Trp
        275                 280                 285

Pro Tyr Leu Met His Glu His Pro Ala Tyr Leu Tyr Ser Leu Glu Val
    290                 295                 300

Arg Leu Thr Ala Gln Thr Ala Ala Gly Ser Val Ser Asp Phe Tyr Thr
305                 310                 315                 320

Leu Pro Val Gly Ile Arg Thr Val Ala Val Thr Glu His Gln Phe Leu
                325                 330                 335

Ile Asn Gly Lys Pro Phe Tyr Phe His Gly Val Asn Lys His Glu Asp
            340                 345                 350

Ala Asp Ile Arg Gly Lys Gly Phe Asp Trp Pro Leu Leu Val Lys Asp
        355                 360                 365

Phe Asn Leu Leu Arg Trp Leu Gly Ala Asn Ala Phe Arg Thr Ser His
    370                 375                 380

Tyr Pro Tyr Ala Glu Glu Val Met Gln Leu Cys Asp Arg Tyr Gly Ile
385                 390                 395                 400

Val Val Ile Asp Glu Ser Pro Gly Val Gly Ile Val Leu Val Glu Ser
                405                 410                 415
```

```
Tyr Ser Asn Val Ser Leu Gln His His Leu Glu Val Met Glu Glu Leu
            420                 425                 430

Val Arg Arg Asp Lys Asn His Pro Ala Val Val Met Trp Ser Val Ala
        435                 440                 445

Asn Glu Pro Ala Ser Phe Leu Lys Pro Ala Gly Tyr Tyr Phe Lys Thr
    450                 455                 460

Leu Ile Ala His Thr Lys Ala Leu Asp Pro Ser Arg Pro Val Thr Phe
465                 470                 475                 480

Val Thr Asn Ser Asn Tyr Glu Ala Asp Leu Gly Ala Pro Tyr Val Asp
            485                 490                 495

Val Ile Cys Val Asn Ser Tyr Tyr Ser Trp Tyr His Asp Tyr Gly His
                500                 505                 510

Met Glu Val Ile Gln Leu Gln Leu Ala Thr Gln Phe Glu Asn Trp Tyr
            515                 520                 525

Arg Thr Tyr Gln Lys Pro Ile Ile Gln Ser Glu Tyr Gly Ala Asp Thr
    530                 535                 540

Ile Ala Gly Phe His Gln Asp Pro Pro Leu Met Phe Ser Glu Glu Tyr
545                 550                 555                 560

Gln Lys Gly Leu Leu Glu Gln Tyr His Leu Val Leu Asp Gln Lys Arg
            565                 570                 575

Lys Glu Tyr Val Val Gly Glu Leu Ile Trp Asn Phe Ala Asp Phe Met
                580                 585                 590

Thr Asn Gln Ser Pro Gln Arg Val Met Gly Asn Lys Lys Gly Ile Phe
            595                 600                 605

Thr Arg Gln Arg Gln Pro Lys Gly Ala Ala Phe Leu Leu Arg Glu Arg
    610                 615                 620

Tyr Trp Lys Leu Ala Asn Glu Thr Arg Tyr Pro Trp Ser Ala Val Lys
625                 630                 635                 640

Ser Gln Cys Leu Glu Asn Ser Pro Phe Thr Leu
            645                 650

<210> SEQ ID NO 16
<211> LENGTH: 651
<212> TYPE: PRT
<213> ORGANISM: Canis familiaris

<400> SEQUENCE: 16

Met Ser Arg Gly Pro Ala Gly Ala Trp Val Ala Leu Gly Pro Leu Leu
1               5                   10                  15

Trp Thr Cys Gly Leu Ala Leu Glu Gly Gly Met Leu Tyr Pro Arg Glu
            20                  25                  30

Ser Pro Ser Arg Glu Arg Lys Asp Leu Asp Gly Leu Trp Ser Phe Arg
        35                  40                  45

Ala Asp Phe Ser Asp Gly Arg Arg Gln Gly Phe Glu Gln Gln Trp Tyr
    50                  55                  60

Arg Ala Pro Leu Arg Glu Ser Gly Pro Thr Leu Asp Met Pro Val Pro
65                  70                  75                  80

Ser Ser Phe Asn Asp Val Gly Gln Asp Arg Gln Leu Arg Ser Phe Val
            85                  90                  95

Gly Trp Val Trp Tyr Glu Arg Glu Ala Thr Leu Pro Arg Arg Trp Ser
            100                 105                 110

Gln Asp Pro Gly Thr Arg Val Val Leu Arg Ile Gly Ser Ala His Tyr
        115                 120                 125

Tyr Ala Ile Val Trp Val Asn Gly Val His Val Ala Glu His Glu Gly
    130                 135                 140
```

```
Gly His Leu Pro Phe Glu Ala Asp Ile Ser Lys Leu Val Gln Ser Gly
145                 150                 155                 160

Pro Leu Ser Ser Cys Arg Ile Thr Leu Ala Ile Asn Asn Thr Leu Thr
                165                 170                 175

Pro His Thr Leu Pro Pro Gly Thr Ile Val Tyr Lys Thr Asp Ala Ser
            180                 185                 190

Lys Tyr Pro Lys Gly Tyr Phe Val Gln Asn Thr Tyr Phe Asp Phe Phe
        195                 200                 205

Asn Tyr Ala Gly Leu His Arg Pro Val Leu Leu Tyr Thr Thr Pro Thr
    210                 215                 220

Thr Tyr Ile Asp Asp Ile Thr Val Thr Thr Gly Val Asp Gln Asp Thr
225                 230                 235                 240

Gly Leu Val Asp Tyr Gln Ile Phe Val Gln Gly Ser Glu His Phe Gln
                245                 250                 255

Leu Glu Val Tyr Leu Leu Asp Glu Glu Gly Lys Val Val Ala Gln Gly
            260                 265                 270

Thr Gly Ser Gln Gly Arg Leu Gln Val Pro Asn Val His Leu Trp Trp
        275                 280                 285

Pro Tyr Leu Met His Glu His Pro Ala Tyr Leu Tyr Ser Leu Glu Val
    290                 295                 300

Arg Leu Thr Ala Gln Met Ala Ala Gly Pro Val Ser Asp Phe Tyr Thr
305                 310                 315                 320

Leu Pro Val Gly Ile Arg Thr Val Ala Val Thr Glu Arg Gln Phe Leu
                325                 330                 335

Ile Asn Gly Lys Pro Phe Tyr Phe His Gly Val Asn Lys His Glu Asp
            340                 345                 350

Ala Asp Ile Arg Gly Lys Gly Phe Asp Trp Pro Leu Leu Val Lys Asp
        355                 360                 365

Phe Asn Leu Leu Arg Trp Leu Gly Ala Asn Ala Phe Arg Thr Ser His
    370                 375                 380

Tyr Pro Tyr Ala Glu Glu Val Met Gln Leu Cys Asp Arg Tyr Gly Ile
385                 390                 395                 400

Val Val Ile Asp Glu Ser Pro Gly Val Gly Ile Met Leu Val Gln Ser
                405                 410                 415

Tyr Ser Asn Val Ser Leu Gln His His Leu Glu Val Met Gly Glu Leu
            420                 425                 430

Val Arg Arg Asp Lys Asn His Pro Ser Val Val Met Trp Ser Val Ala
        435                 440                 445

Asn Glu Pro Thr Ser Phe Leu Lys Pro Ala Ala Tyr Tyr Phe Lys Thr
    450                 455                 460

Leu Ile Ala His Thr Lys Ala Leu Asp Pro Ser Arg Pro Val Thr Phe
465                 470                 475                 480

Val Thr Asn Ser Asn Tyr Glu Ala Asp Leu Gly Ala Pro Tyr Val Asp
                485                 490                 495

Val Ile Cys Val Asn Ser Tyr Tyr Ser Trp Tyr His Asp Tyr Gly His
            500                 505                 510

Met Glu Val Ile Gln Leu Gln Leu Ala Thr Glu Phe Glu Asn Trp Tyr
        515                 520                 525

Arg Thr Tyr Gln Lys Pro Ile Ile Gln Ser Glu Tyr Gly Ala Glu Thr
    530                 535                 540

Ile Ala Gly Phe His Gln Asp Pro Pro Leu Met Phe Ser Glu Glu Tyr
545                 550                 555                 560
```

-continued

```
Gln Lys Gly Leu Leu Glu Gln Tyr His Leu Val Leu Asp Gln Lys Arg
                565                 570                 575
Lys Glu Tyr Val Val Gly Leu Ile Trp Asn Phe Ala Asp Phe Met
            580                 585                 590
Thr Asp Gln Ser Pro Gln Arg Ala Val Gly Asn Arg Lys Gly Ile Phe
            595                 600                 605
Thr Arg Gln Arg Gln Pro Lys Ala Ala Ala Phe Leu Leu Arg Glu Arg
        610                 615                 620
Tyr Trp Lys Leu Ala Asn Glu Thr Gly His His Arg Ser Ala Ala Lys
625                 630                 635                 640
Ser Gln Cys Leu Glu Asn Ser Pro Phe Ala Leu
                645                 650

<210> SEQ ID NO 17
<211> LENGTH: 648
<212> TYPE: PRT
<213> ORGANISM: Cercopithecus aethiops

<400> SEQUENCE: 17

Gly Leu Ala Met Ala Trp Ala Val Leu Gly Pro Leu Trp Gly Cys
1               5                   10                  15
Ala Leu Ala Leu Gln Gly Gly Met Leu Tyr Pro Arg Glu Ser Gln Ser
                20                  25                  30
Arg Glu Arg Lys Glu Leu Asp Gly Leu Trp Ser Phe Arg Ala Asp Phe
            35                  40                  45
Ser Asp Asn Arg Arg Gly Phe Glu Glu Gln Trp Tyr Arg Arg Pro
    50                  55                  60
Leu Arg Glu Ser Gly Pro Thr Leu Asp Met Pro Val Pro Ser Ser Phe
65                  70                  75                  80
Asn Asp Ile Ser Gln Asp Trp Arg Leu Arg His Phe Val Gly Trp Val
                85                  90                  95
Trp Tyr Glu Arg Glu Val Ile Leu Pro Glu Arg Trp Thr Gln Asp Leu
            100                 105                 110
Ser Thr Arg Val Val Leu Arg Ile Gly Ser Ala His Ala Tyr Ala Ile
        115                 120                 125
Val Trp Val Asn Gly Val His Thr Leu Glu His Glu Gly Gly Tyr Leu
    130                 135                 140
Pro Phe Glu Ala Asp Ile Ser Asn Leu Val Gln Val Gly Pro Leu Ser
145                 150                 155                 160
Ser His Val Arg Ile Thr Ile Ala Ile Asn Asn Thr Leu Thr Ser Thr
                165                 170                 175
Thr Leu Pro Pro Gly Thr Ile Gln Tyr Leu Thr Asp Ile Ser Lys Tyr
            180                 185                 190
Pro Lys Gly Tyr Phe Ile Gln Asn Thr Tyr Phe Asp Phe Phe Asn Tyr
        195                 200                 205
Ala Gly Leu Gln Arg Ser Val Leu Leu Tyr Thr Thr Pro Thr Ala Tyr
    210                 215                 220
Ile Asp Asp Ile Thr Val Thr Thr Gly Val Glu His Asp Thr Gly Leu
225                 230                 235                 240
Val Asn Tyr Gln Ile Ser Val Lys Gly Ser Asn Leu Phe Glu Leu Glu
                245                 250                 255
Val Arg Leu Leu Asp Ala Glu Asn Lys Leu Val Ala Asn Gly Thr Gly
            260                 265                 270
```

```
Ile Gln Gly Gln Leu Lys Val Pro Gly Ala Arg Leu Trp Trp Pro Tyr
            275                 280                 285
Leu Met His Glu Arg Pro Ala Tyr Leu Tyr Ser Leu Glu Val Arg Leu
    290                 295                 300
Thr Ala Gln Thr Ser Leu Gly Pro Val Ser Asp Phe Tyr Thr Leu Pro
305                 310                 315                 320
Val Gly Ile Arg Thr Val Ala Val Thr Glu Ser Gln Phe Leu Ile Asn
                325                 330                 335
Gly Lys Pro Phe Tyr Phe His Gly Val Asn Lys His Glu Asp Ala Asp
                340                 345                 350
Ile Arg Gly Lys Gly Phe Asp Trp Pro Leu Leu Val Lys Asp Phe Asn
            355                 360                 365
Leu Leu Arg Trp Leu Gly Ala Asn Ala Phe Arg Thr Ser His Tyr Pro
    370                 375                 380
Tyr Ala Glu Glu Val Leu Gln Met Cys Asp Arg Tyr Gly Ile Val Val
385                 390                 395                 400
Ile Asp Glu Cys Pro Gly Val Gly Leu Ala Leu Pro Gln Phe Phe Asn
                405                 410                 415
Asn Val Ser Leu Gln Asn His Met Arg Val Met Glu Glu Val Val Arg
                420                 425                 430
Arg Asp Lys Asn His Pro Ala Val Val Met Trp Ser Val Ala Asn Glu
            435                 440                 445
Pro Ala Ser His Leu Glu Ser Ala Gly Tyr Tyr Leu Lys Met Val Ile
    450                 455                 460
Thr His Thr Lys Ala Leu Asp Pro Ser Arg Pro Val Thr Phe Val Thr
465                 470                 475                 480
Asn Ser Asn Tyr Ala Ala Asp Lys Gly Ala Pro Tyr Val Asp Val Ile
                485                 490                 495
Cys Leu Asn Ser Tyr Tyr Ser Trp Tyr His Asp Tyr Gly His Leu Glu
                500                 505                 510
Leu Ile Gln Arg Gln Leu Thr Thr Gln Phe Glu Asn Trp Tyr Lys Thr
            515                 520                 525
Tyr Gln Lys Pro Ile Ile Gln Ser Glu Tyr Gly Ala Glu Thr Ile Val
    530                 535                 540
Gly Phe His Gln Asp Pro Pro Leu Met Phe Thr Glu Glu Tyr Gln Lys
545                 550                 555                 560
Ser Leu Leu Glu Gln Tyr His Val Val Leu Asp Gln Lys Arg Arg Lys
                565                 570                 575
Tyr Val Val Gly Glu Leu Ile Trp Asn Phe Ala Asp Phe Met Thr Glu
                580                 585                 590
Gln Ser Pro Thr Arg Val Leu Gly Asn Lys Lys Gly Val Phe Thr Arg
            595                 600                 605
Gln Arg Gln Pro Lys Ser Ala Ala Phe Leu Leu Arg Glu Arg Tyr Trp
    610                 615                 620
Lys Ile Ala Asn Glu Thr Arg Tyr Pro His Ser Ile Ala Lys Ser Gln
625                 630                 635                 640
Cys Leu Glu Asn Ser Pro Phe Thr
                645

<210> SEQ ID NO 18
<211> LENGTH: 651
<212> TYPE: PRT
<213> ORGANISM: Homo sapiens
```

<400> SEQUENCE: 18

```
Met Ala Arg Gly Ser Ala Val Ala Trp Ala Leu Gly Pro Leu Leu
1               5                   10                  15
Trp Gly Cys Ala Leu Gly Leu Gln Gly Gly Met Leu Tyr Pro Gln Glu
                20                  25                  30
Ser Pro Ser Arg Glu Cys Lys Glu Leu Asp Gly Leu Trp Ser Phe Arg
                35                  40                  45
Ala Asp Phe Ser Asp Asn Arg Arg Gly Phe Glu Glu Gln Trp Tyr
        50                  55                  60
Arg Arg Pro Leu Trp Glu Ser Gly Pro Thr Val Asp Met Pro Val Pro
65                  70                  75                  80
Ser Ser Phe Asn Asp Ile Ser Gln Asp Trp Arg Leu Arg His Phe Val
                    85                  90                  95
Gly Trp Val Trp Tyr Glu Arg Glu Val Ile Leu Pro Glu Arg Trp Thr
                100                 105                 110
Gln Asp Leu Arg Thr Arg Val Val Leu Arg Ile Gly Ser Ala His Ser
                115                 120                 125
Tyr Ala Ile Val Trp Val Asn Gly Val Asp Thr Leu Glu His Glu Gly
            130                 135                 140
Gly Tyr Leu Pro Phe Glu Ala Asp Ile Ser Asn Leu Val Gln Val Gly
145                 150                 155                 160
Pro Leu Pro Ser Arg Leu Arg Ile Thr Ile Ala Ile Asn Asn Thr Leu
                165                 170                 175
Thr Pro Thr Thr Leu Pro Pro Gly Thr Ile Gln Tyr Leu Thr Asp Thr
                180                 185                 190
Ser Lys Tyr Pro Lys Gly Tyr Phe Val Gln Asn Thr Tyr Phe Asp Phe
            195                 200                 205
Phe Asn Tyr Ala Gly Leu Gln Arg Ser Val Leu Leu Tyr Thr Thr Pro
        210                 215                 220
Thr Thr Tyr Ile Asp Asp Ile Thr Val Thr Thr Ser Val Glu Gln Asp
225                 230                 235                 240
Ser Gly Leu Val Asn Tyr Gln Ile Ser Val Lys Gly Ser Asn Leu Phe
                245                 250                 255
Lys Leu Glu Val Arg Leu Leu Asp Ala Glu Asn Lys Val Val Ala Asn
                260                 265                 270
Gly Thr Gly Thr Gln Gly Gln Leu Lys Val Pro Gly Val Ser Leu Trp
            275                 280                 285
Trp Pro Tyr Leu Met His Glu Arg Pro Ala Tyr Leu Tyr Ser Leu Glu
        290                 295                 300
Val Gln Leu Thr Ala Gln Thr Ser Leu Gly Pro Val Ser Asp Phe Tyr
305                 310                 315                 320
Thr Leu Pro Val Gly Ile Arg Thr Val Ala Val Thr Lys Ser Gln Phe
                325                 330                 335
Leu Ile Asn Gly Lys Pro Phe Tyr Phe His Gly Val Asn Lys His Glu
                340                 345                 350
Asp Ala Asp Ile Arg Gly Lys Gly Phe Asp Trp Pro Leu Leu Val Lys
            355                 360                 365
Asp Phe Asn Leu Leu Arg Trp Leu Gly Ala Asn Ala Phe Arg Thr Ser
        370                 375                 380
His Tyr Pro Tyr Ala Glu Glu Val Met Gln Met Cys Asp Arg Tyr Gly
385                 390                 395                 400
Ile Val Val Ile Asp Glu Cys Pro Gly Val Gly Leu Ala Leu Pro Gln
                405                 410                 415
```

Phe Phe Asn Asn Val Ser Leu His His His Met Gln Val Met Glu Glu
                420                 425                 430

Val Val Arg Arg Asp Lys Asn His Pro Ala Val Val Met Trp Ser Val
            435                 440                 445

Ala Asn Glu Pro Ala Ser His Leu Glu Ser Ala Gly Tyr Tyr Leu Lys
450                 455                 460

Met Val Ile Ala His Thr Lys Ser Leu Asp Pro Ser Arg Pro Val Thr
465                 470                 475                 480

Phe Val Ser Asn Ser Asn Tyr Ala Ala Asp Lys Gly Ala Pro Tyr Val
                485                 490                 495

Asp Val Ile Cys Leu Asn Ser Tyr Tyr Ser Trp Tyr His Asp Tyr Gly
                500                 505                 510

His Leu Glu Leu Ile Gln Leu Gln Leu Ala Thr Gln Phe Glu Asn Trp
            515                 520                 525

Tyr Lys Lys Tyr Gln Lys Pro Ile Ile Gln Ser Glu Tyr Gly Ala Glu
530                 535                 540

Thr Ile Ala Gly Phe His Gln Asp Pro Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
            580                 585                 590

Met Thr Glu Gln Ser Pro Thr Arg Val Leu Gly Asn Lys Lys Gly Ile
            595                 600                 605

Phe Thr Arg Gln Arg Gln Pro Lys Ser Ala Ala Phe Leu Leu Arg Glu
610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Pro Phe Thr
                645                 650

<210> SEQ ID NO 19
<211> LENGTH: 570
<212> TYPE: PRT
<213> ORGANISM: Sulfolobus solfataricus

<400> SEQUENCE: 19

Met Arg Ser Phe Tyr Arg Pro Lys Ile Asp Leu Gln Gly Phe Trp Lys
1               5                   10                  15

Phe Lys Ile Asp Asn Glu Asn Thr Gly Glu Glu Asn Gly Trp Tyr Lys
                20                  25                  30

Gly Leu Glu Ser Glu Asp Ile Ile Tyr Val Pro Ala Ser Trp Asn Glu
            35                  40                  45

Gln Asn Pro Lys Trp Asp Gln Phe Ser Gly Ile Ala Trp Tyr Gln Lys
        50                  55                  60

Asp Leu Phe Val Ser Asn Asp Asn Gly Asn Arg Lys Ala Trp Met Val
65                  70                  75                  80

Phe Glu Gly Ala Gly Tyr Ile Thr Lys Leu Trp Ile Asn Gly Glu Tyr
                85                  90                  95

Gly Gly Thr His Glu Gly Ser Phe Thr Gln Phe Lys Phe Pro Ile Lys
            100                 105                 110

Leu Lys Val Asn Glu Phe Asn Lys Ile Val Val Lys Ile Asp Asn Thr
        115                 120                 125

Pro Ser Pro Tyr Asn Leu Pro Pro Ala Arg Asp Leu Asn Asn Ala Ala
    130                 135                 140

-continued

```
Phe Asp Phe Phe Asn Tyr Gly Gly Ile His Arg Pro Val Tyr Ile Glu
145                 150                 155                 160

Phe Val Asp Glu Cys His Val Glu Asp Ile Thr Val Tyr Thr Lys Ser
            165                 170                 175

Tyr Gly His Leu Lys Val Glu Ile Leu Ser Glu Cys Asn Gln Arg Phe
            180                 185                 190

Ser Leu Arg Phe Lys Leu Val Asp Lys Glu Gly Arg Val Ile Leu Asn
        195                 200                 205

Glu Glu Ser Ser Asn Glu Val Phe Glu Lys Asp Val Asn Asn Val Ile
    210                 215                 220

Pro Trp Ser Pro Asp Asn Pro Tyr Leu Tyr Thr Leu Ile Val Glu Met
225                 230                 235                 240

Tyr Val Gly Gly Asn Leu Lys Asp Ser Val Tyr Glu Arg Ile Gly Phe
            245                 250                 255

Arg Asp Val Glu Val Lys Asp Gly Lys Ile Tyr Leu Asn Gly Lys Pro
            260                 265                 270

Ile Phe Leu Lys Gly Phe Gly Arg His Glu Asp Phe Pro Ile Leu Gly
        275                 280                 285

Lys Phe Thr Tyr Gly Ala Val Leu Val Arg Asp Phe Tyr Leu Met Arg
    290                 295                 300

Lys Ile Gly Ala Asn Ser Phe Arg Thr Ser His Tyr Pro Tyr Ser Asn
305                 310                 315                 320

Glu His Leu Asp Leu Ala Asp Glu Met Gly Phe Leu Val Ile Leu Glu
            325                 330                 335

Pro Pro Leu Cys Tyr Ser Asn Ile Ser Arg Val Met Ser Gln Glu Glu
            340                 345                 350

Ile Ala Lys Met Phe Gly Asp Val Lys Tyr Phe Glu Lys Val Arg Asp
        355                 360                 365

Thr Ile Lys Glu Met Ile Arg Gln His Lys Asn Arg Pro Ser Val Ile
    370                 375                 380

Met Tyr Ser Val Met Asn Glu Pro Pro Ser Asp Ile Arg Glu Val Ala
385                 390                 395                 400

Glu Phe Ile Arg Arg Glu Val Glu Leu Phe Lys Ser Leu Asp Ser Ser
            405                 410                 415

Arg Pro Val Thr Phe Ala Ser His Arg Ser Val Arg Asp Leu Ala Leu
            420                 425                 430

Glu Tyr Val Asp Val Ile Ser Leu Asn Tyr Tyr His Gly Trp Tyr Thr
        435                 440                 445

Glu Trp Gly Asp Ile Asp Ser Gly Val Lys Val Val Ala Ile Glu Leu
    450                 455                 460

Glu Glu Ile His Lys Lys Phe Pro Glu Lys Pro Ile Ile Ile Thr Glu
465                 470                 475                 480

Phe Gly Ala Asp Ala Ile Tyr Gly Leu His Ser Asp Pro Pro Gln Met
            485                 490                 495

Trp Ser Glu Glu Tyr Gln Ser Glu Met Ile Arg Lys Tyr Ile Glu Ala
            500                 505                 510

Leu Arg Glu Lys Asp Tyr Ile Val Gly Phe His Ile Trp Asn Phe Ala
        515                 520                 525

Asp Phe Arg Thr Pro Gln Asn Pro Ser Arg Thr Ile Leu Asn Arg Lys
    530                 535                 540
```

```
Gly Ile Phe Thr Arg Asp Arg Gln Pro Lys Leu Ala Ala Lys Val Val
545                 550                 555                 560

Glu Glu Leu Phe Lys Asn Lys Leu Arg Ser
                565                 570

<210> SEQ ID NO 20
<211> LENGTH: 563
<212> TYPE: PRT
<213> ORGANISM: Thermotoga maritima

<400> SEQUENCE: 20

Met Val Arg Pro Gln Arg Asn Lys Lys Arg Phe Ile Leu Ile Leu Asn
1               5                   10                  15

Gly Val Trp Asn Leu Glu Val Thr Ser Lys Asp Arg Pro Ile Ala Val
                20                  25                  30

Pro Gly Ser Trp Asn Glu Gln Tyr Gln Asp Leu Cys Tyr Glu Glu Gly
            35                  40                  45

Pro Phe Thr Tyr Lys Thr Thr Phe Tyr Val Pro Lys Glu Leu Ser Gln
    50                  55                  60

Lys His Ile Arg Leu Tyr Phe Ala Ala Val Asn Thr Asp Cys Glu Val
65                  70                  75                  80

Phe Leu Asn Gly Glu Lys Val Gly Glu Asn His Ile Glu Tyr Leu Pro
                85                  90                  95

Phe Glu Val Asp Val Thr Gly Lys Val Lys Ser Gly Glu Asn Glu Leu
            100                 105                 110

Arg Val Val Val Glu Asn Arg Leu Lys Val Gly Gly Phe Pro Ser Lys
        115                 120                 125

Val Pro Asp Ser Gly Thr His Thr Val Gly Phe Phe Gly Ser Phe Pro
130                 135                 140

Pro Ala Asn Phe Asp Phe Phe Pro Tyr Gly Gly Ile Ile Arg Pro Val
145                 150                 155                 160

Leu Ile Glu Phe Thr Asp His Ala Arg Ile Leu Asp Ile Trp Val Asp
                165                 170                 175

Thr Ser Glu Ser Glu Pro Glu Lys Lys Leu Gly Lys Val Lys Val Lys
            180                 185                 190

Ile Glu Val Ser Glu Glu Ala Val Gly Gln Glu Met Thr Ile Lys Leu
        195                 200                 205

Gly Glu Glu Glu Lys Lys Ile Arg Thr Ser Asn Arg Phe Val Glu Gly
210                 215                 220

Glu Phe Ile Leu Glu Asn Ala Arg Phe Trp Ser Leu Glu Asp Pro Tyr
225                 230                 235                 240

Leu Tyr Pro Leu Lys Val Glu Leu Glu Lys Asp Glu Tyr Thr Leu Asp
                245                 250                 255

Ile Gly Ile Arg Thr Ile Ser Trp Asp Glu Lys Arg Leu Tyr Leu Asn
            260                 265                 270

Gly Lys Pro Val Phe Leu Lys Gly Phe Gly Lys His Glu Glu Phe Pro
        275                 280                 285

Val Leu Gly Gln Gly Thr Phe Tyr Pro Leu Met Ile Lys Asp Phe Asn
290                 295                 300

Leu Leu Lys Trp Ile Asn Ala Asn Ser Phe Arg Thr Ser His Tyr Pro
305                 310                 315                 320

Tyr Ser Glu Glu Trp Leu Asp Leu Ala Asp Arg Leu Gly Ile Leu Val
                325                 330                 335

Ile Asp Glu Ala Pro His Val Gly Ile Thr Arg Tyr His Tyr Asn Pro
            340                 345                 350
```

```
Glu Thr Gln Lys Ile Ala Glu Asp Asn Ile Arg Arg Met Ile Asp Arg
            355                 360                 365

His Lys Asn His Pro Ser Val Ile Met Trp Ser Val Ala Asn Glu Pro
        370                 375                 380

Glu Ser Asn His Pro Asp Ala Glu Gly Phe Phe Lys Ala Leu Tyr Glu
385                 390                 395                 400

Thr Ala Asn Glu Met Asp Arg Thr Arg Pro Val Val Met Val Ser Met
                405                 410                 415

Met Asp Ala Pro Asp Glu Arg Thr Arg Asp Val Ala Leu Lys Tyr Phe
            420                 425                 430

Asp Ile Val Cys Val Asn Arg Tyr Gly Trp Tyr Ile Tyr Gln Gly
        435                 440                 445

Arg Ile Glu Glu Gly Leu Gln Ala Leu Glu Lys Asp Ile Glu Glu Leu
        450                 455                 460

Tyr Ala Arg His Arg Lys Pro Ile Phe Val Thr Glu Phe Gly Ala Asp
465                 470                 475                 480

Ala Ile Ala Gly Ile His Tyr Asp Pro Pro Gln Met Phe Ser Glu Glu
                485                 490                 495

Tyr Gln Ala Glu Leu Val Glu Lys Thr Ile Arg Leu Leu Lys Lys
            500                 505                 510

Asp Tyr Ile Ile Gly Thr His Val Trp Ala Phe Ala Asp Phe Lys Thr
        515                 520                 525

Pro Gln Asn Val Arg Arg Pro Ile Leu Asn His Lys Gly Val Phe Thr
        530                 535                 540

Arg Asp Arg Gln Pro Lys Leu Val Ala His Val Leu Arg Arg Leu Trp
545                 550                 555                 560

Ser Glu Val

<210> SEQ ID NO 21
<211> LENGTH: 598
<212> TYPE: PRT
<213> ORGANISM: Lactobacillus gasseri

<400> SEQUENCE: 21

Met Glu Ser Ala Leu Tyr Pro Ile Gln Asn Lys Tyr Arg Phe Asn Thr
1               5                   10                  15

Leu Met Asn Gly Thr Trp Gln Phe Glu Thr Asp Pro Asn Ser Val Gly
            20                  25                  30

Leu Asp Glu Gly Trp Asn Lys Glu Leu Pro Asp Pro Glu Glu Met Pro
        35                  40                  45

Val Pro Gly Thr Phe Ala Glu Leu Thr Thr Lys Arg Asp Arg Lys Tyr
50                  55                  60

Tyr Thr Gly Asp Phe Trp Tyr Gln Lys Asp Phe Ile Pro Ser Phe
65                  70                  75                  80

Leu Lys Lys Lys Glu Leu Tyr Ile Arg Phe Gly Ser Val Thr His Arg
            85                  90                  95

Ala Lys Val Phe Ile Asn Gly His Glu Val Gly Gln His Glu Gly Gly
                100                 105                 110

Phe Leu Pro Phe Gln Val Lys Ile Ser Asn Tyr Ile Asn Tyr Asp Gln
            115                 120                 125

Thr Asn Arg Val Thr Val Leu Val Asn Asn Glu Leu Ser Glu Lys Ala
        130                 135                 140

Ile Pro Cys Gly Thr Glu Glu Ile Leu Asp Asn Gly Gln Lys Leu Ala
145                 150                 155                 160
```

-continued

```
Gln Pro Tyr Phe Asp Phe Phe Asn Tyr Ser Gly Ile Met Arg Asn Val
                165                 170                 175

Trp Leu Leu Ala Leu Pro Gln Ser Gln Ile Thr Asn Phe Lys Leu Asn
            180                 185                 190

Tyr Gln Leu Ala Asn Asn Lys Ala Thr Ile Thr Tyr Asn Ile Glu Ala
        195                 200                 205

Asn Asn Asn Ala Glu Phe Lys Val Thr Leu Phe Asp Asn Gln Lys Glu
    210                 215                 220

Val Ala Cys Ala Thr Ser Lys Asn Thr Ser Ser Leu Thr Ile Lys Asn
225                 230                 235                 240

Pro His Leu Trp Ser Pro Asn Asp Pro Tyr Ser Tyr Lys Ile Lys Ile
                245                 250                 255

Glu Met Leu Glu Asp Gly Lys Thr Val Asp Glu Tyr Thr Asp Lys Ile
            260                 265                 270

Gly Ile Arg Thr Val Lys Ile Val Asn Asp Lys Ile Leu Leu Asn Asn
        275                 280                 285

His Pro Ile Tyr Leu Lys Gly Phe Gly Lys His Glu Asp Phe Asn Val
    290                 295                 300

Leu Gly Lys Ala Val Asn Glu Ser Ile Ile Lys Arg Asp Tyr Glu Cys
305                 310                 315                 320

Met Lys Trp Ile Gly Ala Asn Cys Phe Arg Ser Ser His Tyr Pro Tyr
                325                 330                 335

Ala Glu Glu Trp Tyr Gln Tyr Ala Asp Lys Tyr Gly Phe Leu Ile Ile
            340                 345                 350

Asp Glu Val Pro Ala Val Gly Leu Asn Arg Ser Ile Thr Asn Phe Leu
        355                 360                 365

Asn Val Thr Asn Ser Asn Gln Ser His Phe Phe Ala Ser Lys Thr Val
    370                 375                 380

Pro Glu Leu Lys Lys Val His Glu Gln Glu Ile Lys Glu Met Ile Asp
385                 390                 395                 400

Arg Asp Gln Arg His Pro Ser Val Ile Ala Trp Ser Leu Phe Asn Glu
                405                 410                 415

Pro Glu Ser Thr Thr Gln Glu Ser Tyr Asp Tyr Phe Lys Asp Ile Phe
            420                 425                 430

Ala Phe Ala Arg Lys Leu Asp Pro Gln Asn Arg Pro Tyr Thr Gly Thr
        435                 440                 445

Leu Val Met Gly Ser Gly Pro Lys Val Asp Lys Leu His Pro Leu Cys
    450                 455                 460

Asp Phe Val Cys Leu Asn Arg Tyr Tyr Gly Trp Tyr Val Ala Gly Gly
465                 470                 475                 480

Pro Glu Ile Val Asn Ala Lys Lys Met Leu Glu Asp Glu Leu Asp Gly
                485                 490                 495

Trp Gln Asn Leu Lys Leu Asn Lys Pro Phe Val Phe Thr Glu Phe Gly
            500                 505                 510

Ala Asp Thr Leu Ser Ser Ser His Arg Leu Pro Asp Glu Met Trp Ser
        515                 520                 525

Gln Glu Tyr Gln Asn Glu Tyr Tyr Gln Met Tyr Phe Asp Ile Phe Lys
    530                 535                 540

Lys Tyr Pro Phe Ile Cys Gly Glu Leu Val Trp Asn Phe Ala Asp Phe
545                 550                 555                 560

Lys Thr Ser Glu Gly Ile Met Arg Val Gly Gly Asn Asp Lys Gly Ile
                565                 570                 575
```

Phe Thr Arg Asp Arg Glu Pro Lys Asp Ile Ala Phe Thr Leu Lys Lys
            580                 585                 590

Arg Trp Gln Gln Leu Asn
        595

<210> SEQ ID NO 22
<211> LENGTH: 603
<212> TYPE: PRT
<213> ORGANISM: Escherichia coli

<400> SEQUENCE: 22

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

```
Ala Ala Val Gly Phe Asn Leu Ser Leu Gly Ile Gly Phe Glu Ala Gly
            355                 360                 365

Asn Lys Pro Lys Glu Leu Tyr Ser Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
    530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
        595                 600

<210> SEQ ID NO 23
<211> LENGTH: 602
<212> TYPE: PRT
<213> ORGANISM: Staphylococcus sp.

<400> SEQUENCE: 23

Met Leu Tyr Pro Ile Asn Thr Glu Thr Arg Gly Val Phe Asp Leu Asn
1               5                   10                  15

Gly Val Trp Asn Phe Lys Leu Asp Tyr Gly Lys Gly Leu Glu Glu Lys
                20                  25                  30

Trp Tyr Glu Ser Lys Leu Thr Asp Thr Ile Ser Met Ala Val Pro Ser
            35                  40                  45

Ser Tyr Asn Asp Ile Gly Val Thr Lys Glu Ile Arg Asn His Ile Gly
        50                  55                  60

Tyr Val Trp Tyr Glu Arg Glu Phe Thr Val Pro Ala Tyr Leu Lys Asp
65                  70                  75                  80

Gln Arg Ile Val Leu Arg Phe Gly Ser Ala Thr His Lys Ala Ile Val
                85                  90                  95

Tyr Val Asn Gly Glu Leu Val Val Glu His Lys Gly Gly Phe Leu Pro
            100                 105                 110

Phe Glu Ala Glu Ile Asn Asn Ser Leu Arg Asp Gly Met Asn Arg Val
        115                 120                 125
```

```
Thr Val Ala Val Asp Asn Ile Leu Asp Asp Ser Thr Leu Pro Val Gly
    130                 135                 140

Leu Tyr Ser Glu Arg His Glu Glu Gly Leu Gly Lys Val Ile Arg Asn
145                 150                 155                 160

Lys Pro Asn Phe Asp Phe Phe Asn Tyr Ala Gly Leu His Arg Pro Val
                165                 170                 175

Lys Ile Tyr Thr Thr Pro Phe Thr Tyr Val Glu Asp Ile Ser Val Val
                180                 185                 190

Thr Asp Phe Asn Gly Pro Thr Gly Thr Val Thr Tyr Thr Val Asp Phe
                195                 200                 205

Gln Gly Lys Ala Glu Thr Val Lys Val Ser Val Val Asp Glu Glu Gly
    210                 215                 220

Lys Val Ala Ser Thr Glu Gly Leu Ser Gly Asn Val Glu Ile Pro
225                 230                 235                 240

Asn Val Ile Leu Trp Glu Pro Leu Asn Thr Tyr Leu Tyr Gln Ile Lys
                245                 250                 255

Val Glu Leu Val Asn Asp Gly Leu Thr Ile Asp Val Tyr Glu Glu Pro
                260                 265                 270

Phe Gly Val Arg Thr Val Glu Val Asn Asp Gly Lys Phe Leu Ile Asn
            275                 280                 285

Asn Lys Pro Phe Tyr Phe Lys Gly Phe Gly Lys His Glu Asp Thr Pro
290                 295                 300

Ile Asn Gly Arg Gly Phe Asn Glu Ala Ser Asn Val Met Asp Phe Asn
305                 310                 315                 320

Ile Leu Lys Trp Ile Gly Ala Asn Ser Phe Arg Thr Ala His Tyr Pro
                325                 330                 335

Tyr Ser Glu Glu Leu Met Arg Leu Ala Asp Arg Glu Gly Leu Val Val
                340                 345                 350

Ile Asp Glu Thr Pro Ala Val Gly Val His Leu Asn Phe Met Ala Thr
                355                 360                 365

Thr Gly Leu Gly Glu Gly Ser Glu Arg Val Ser Thr Trp Glu Lys Ile
    370                 375                 380

Arg Thr Phe Glu His His Gln Asp Val Leu Arg Glu Leu Val Ser Arg
385                 390                 395                 400

Asp Lys Asn His Pro Ser Val Val Met Trp Ser Ile Ala Asn Glu Ala
                405                 410                 415

Ala Thr Glu Glu Glu Gly Ala Tyr Glu Tyr Phe Lys Pro Leu Val Glu
                420                 425                 430

Leu Thr Lys Glu Leu Asp Pro Gln Lys Arg Pro Val Thr Ile Val Leu
    435                 440                 445

Phe Val Met Ala Thr Pro Glu Thr Asp Lys Val Ala Glu Leu Ile Asp
    450                 455                 460

Val Ile Ala Leu Asn Arg Tyr Asn Gly Trp Tyr Phe Asp Gly Gly Asp
465                 470                 475                 480

Leu Glu Ala Ala Lys Val His Leu Arg Gln Glu Phe His Ala Trp Asn
                485                 490                 495

Lys Arg Cys Pro Gly Lys Pro Ile Met Ile Thr Glu Tyr Gly Ala Asp
                500                 505                 510

Thr Val Ala Gly Phe His Asp Ile Asp Pro Val Met Phe Thr Glu Glu
                515                 520                 525

Tyr Gln Val Glu Tyr Tyr Gln Ala Asn His Val Val Phe Asp Glu Phe
    530                 535                 540
```

```
Glu Asn Phe Val Gly Glu Gln Ala Trp Asn Phe Ala Asp Phe Ala Thr
545                 550                 555                 560

Ser Gln Gly Val Met Arg Val Gln Gly Asn Lys Lys Gly Val Phe Thr
                565                 570                 575

Arg Asp Arg Lys Pro Lys Leu Ala Ala His Val Phe Arg Glu Arg Trp
            580                 585                 590

Thr Asn Ile Pro Asp Phe Gly Tyr Lys Asn
        595                 600

<210> SEQ ID NO 24
<211> LENGTH: 19
<212> TYPE: DNA
<213> ORGANISM: artificial
<220> FEATURE:
<223> OTHER INFORMATION: primer ITS-fwd1

<400> SEQUENCE: 24
tccgtaggtg aacctgcgg                                                   19

<210> SEQ ID NO 25
<211> LENGTH: 20
<212> TYPE: DNA
<213> ORGANISM: artificial
<220> FEATURE:
<223> OTHER INFORMATION: Primer ITS-rev4

<400> SEQUENCE: 25
tcctccgctt attgatatgc                                                  20

<210> SEQ ID NO 26
<211> LENGTH: 21
<212> TYPE: DNA
<213> ORGANISM: artificial
<220> FEATURE:
<223> OTHER INFORMATION: Primer NS3

<400> SEQUENCE: 26
gcaagtctgg tgccagcagc c                                                21

<210> SEQ ID NO 27
<211> LENGTH: 24
<212> TYPE: DNA
<213> ORGANISM: artificial
<220> FEATURE:
<223> OTHER INFORMATION: Primer NS6

<400> SEQUENCE: 27
gcatcacaga cctgttattg cctc                                             24

<210> SEQ ID NO 28
<211> LENGTH: 577
<212> TYPE: DNA
<213> ORGANISM: Scopulariopsis sp. isolate 38.3
<220> FEATURE:
<221> NAME/KEY: ITS1
<222> LOCATION: (1)..(167)
<220> FEATURE:
<221> NAME/KEY: 5.8S rRNA
<222> LOCATION: (168)..(324)
<220> FEATURE:
<221> NAME/KEY: ITS2
<222> LOCATION: (325)..(490)
<220> FEATURE:
<221> NAME/KEY: partial 28S rRNA
<222> LOCATION: (491)..(538)
```

```
<400> SEQUENCE: 28
gggatcatta ccgaagttac tcttcaaaac ccattgtgaa ccttacctct tgccgcgcgt      60
tgcctcggcg gggaggcggg gtctgggtcg gcgcgcccct caccgggccg ccgtcccgtc     120
ccgtccccgc cggccgcgcc aaactctaaa tttgaaaaag cgtactgcac gttctgattc     180
aaaacaaaaa acaagtcaaa acttttaaca acggatctct tggttctggc atcgatgaag     240
aacgcagcga aatgcgataa gtaatgtgaa ttgcagaatt cagtgaatca tcgaatcttt     300
gaacgcacat tgcgcccggc agcaatctgc cgggcatgcc tgtccgagcg tcatttcttc     360
cctcgagcgc ggctagccct acggggcctg ccgtcgcccg tgttgggggc tctacgggtg     420
gggctcgtcc cccccgcagt ccccgaaatg tagtggcggt ccagccgcgg cgccccctgc     480
gtagtagatc ctacatctcg catcgggtcc ggcgaaggc cagccgtcga acctttttatt    540 tcatggtttg acctcggatc aggtagggtt acccgct                              577

<210> SEQ ID NO 29
<211> LENGTH: 528
<212> TYPE: DNA
<213> ORGANISM: Penicillium canescens isolate RPK
<220> FEATURE:
<221> NAME/KEY: ITS1
<222> LOCATION: (1)..(167)
<220> FEATURE:
<221> NAME/KEY: 5.8S rRNA
<222> LOCATION: (168)..(324)
<220> FEATURE:
<221> NAME/KEY: ITS2
<222> LOCATION: (325)..(490)
<220> FEATURE:
<221> NAME/KEY: partial 28S rRNA
<222> LOCATION: (491)..(528)

<400> SEQUENCE: 29
cgagaattct ctgaattcaa cctcccaccc gtgtttattg taccttgttg cttcggcggg      60
cccgcctcac ggccgccggg gggcatctgc ccccgggccc gcgcccgccg aagacacctt     120
gaactctgta tgaaaattgc agtctgagtc taaatataaa ttatttaaaa cttttcaacaa    180 cggatctctt ggttccggca tcgatgaaga acgcagcgaa atgcgatacg taatgtgaat     240
tgcagaattc agtgaatcat cgagtctttg aacgcacatt gcgcccctg gtattccggg     300 gggcatgcct gtccgagcgt cattgctgcc ctcaagcccg gcttgtgtgt tgggtctcgt    360
cccccttccc gggggacgg gcccgaaagg cagcggcggc accgcgtccg gtcctcgagc    420 gtatgggct ttgtcacccg ctctgtaggc ccggccggcg cttgccgatc aaccaaaact    480
tttttccagg ttgacctcgg atcaggtagg gataccccgct gaacttaa                 528

<210> SEQ ID NO 30
<211> LENGTH: 832
<212> TYPE: DNA
<213> ORGANISM: Scopulariopsis sp. isolate RP38.3

<400> SEQUENCE: 30
aattccagct ccaatagcgt atattaaagt tgttgtggtt aaaaagctcg tagtcgaacc     60
ttgggcctgg ctggccggtc cccctcaccg ggtgcactga tccagccggg cctttccctc   120
tgtggaaccc catggccttc actggctgtg cgggggaaac aggactttta ctgtgaaaaa    180
attagagtgc tccaggcagg cctatgctcg aatacattag catggaataa tagaataga    240 cgtgtggttc tatttgttg gtttctagga ccgccgtaat gattaatagg gacagtcggg     300
ggcatcagta ttcagttgtc agaggtgaaa ttcttggatc tactgaagac taactactgc    360
```

```
gaaagcattt gccaaggatg ttttcattga taaggaacga aagttagggg atcgaagacg    420
atcagatacc gtcgtagtct taactataaa ctatgccgac tagggatcgg acgatgttat    480
tatttgacgc gttcggcacc tttcgagaaa tcaaagtgct tgggctccag ggggagtatg    540
gtcgcaaggc tgaaacttaa agaaattgac ggaagggcac caccagggt ggaacctgcg     600 gcttaatttg actcaacacg gggaaactca ccaggtccag acacagtgag gattgacaga    660
ttgagagctc tttcttgatt ctgtgggtgg tggtgcatgg ccgttcttag ttggtggagt    720
gatttgtctg cttaattgcg ataacgaacg agaccttaac ctgctaaata gcccgtactg    780
ctctggcagt tcgccggctt cttagaggga ctatcggctc aagccgagga at            832
```

<210> SEQ ID NO 31
<211> LENGTH: 836
<212> TYPE: DNA
<213> ORGANISM: Penicillium canescens isolate RPK

<400> SEQUENCE: 31

```
ttccagctcc aatagcgtat attaaagttg ttgcagttaa aaagctcgta gttgaacctt     60
gggtctggct ggccggtccg cctcaccgcg agtactggtc cggctggacc tttccttctg    120 ggaacctca tggccttcac tggctgtggg gggaaccagg acttttactg tgaaaaaatt     180
agagtgttca aagcaggcct tgctcgaat acattagcat ggataatag aataggacgt      240 gcggttctat tttgttggtt tctaggaccg ccgtaatgat taatagggat agtcgggggc    300
gtcagtattc agctgtcaga ggtgaaattc ttggatttgc tgaagactaa ctactgcgaa    360
agcattcgcc aaggatgttt tcattaatca gggaacgaaa gttagggat cgaagacgat     420 cagataccgt cgtagtctta accataaact atgccgacta gggatcggac gggattctat    480
aatgacccgt tcggcacctt acgagaaatc aaagtttttg ggttctgggg ggagtatggt    540
cgcaaggctg aaacttaaag aaattgacgg aagggcacca caaggcgtgg agcctgcggc    600
ttaatttgac tcaacacggg gaaactcacc aggtccagac aaaataagga ttgacagatt    660
gagagctctt tcttgatctt ttggatggtg gtgcatggcc gttcttagtt ggtggagtga    720
tttgtctgct taattgcgat aacgaacgag acctcggccc ttaaatagcc cggtccgcat    780
ttgcgggccg ctggcttctt aggggacta tcggctcaag ccgatggaag tgcagg        836
```

<210> SEQ ID NO 32
<211> LENGTH: 39
<212> TYPE: DNA
<213> ORGANISM: artificial
<220> FEATURE:
<223> OTHER INFORMATION: Primer gus-fwd+T3
<220> FEATURE:
<221> NAME/KEY: modified_base
<222> LOCATION: (37)..(37)
<223> OTHER INFORMATION: n is inosine
<220> FEATURE:
<221> NAME/KEY: misc_feature
<222> LOCATION: (37)..(37)
<223> OTHER INFORMATION: n is a, c, g, or t

<400> SEQUENCE: 32

```
aattaaccct cactaaaggg ayttytwyaa ytaygcngg                            39
```

<210> SEQ ID NO 33
<211> LENGTH: 39
<212> TYPE: DNA
<213> ORGANISM: artificial
<220> FEATURE:
<223> OTHER INFORMATION: Primer gus-rev+T7

```
<220> FEATURE:
<221> NAME/KEY: modified_base
<222> LOCATION: (28)..(28)
<223> OTHER INFORMATION: n is inosine
<220> FEATURE:
<221> NAME/KEY: misc_feature
<222> LOCATION: (28)..(28)
<223> OTHER INFORMATION: n is a, c, g, or t

<400> SEQUENCE: 33
gtaatacgac tcactatagg graartcngc raaraacca                              39

<210> SEQ ID NO 34
<211> LENGTH: 36
<212> TYPE: DNA
<213> ORGANISM: artificial
<220> FEATURE:
<223> OTHER INFORMATION: Primer gus(Scop)-fwd+SpeI

<400> SEQUENCE: 34
catagcacta gtgccgacac tgaccaatgg aagacg                                 36

<210> SEQ ID NO 35
<211> LENGTH: 35
<212> TYPE: DNA
<213> ORGANISM: artificial
<220> FEATURE:
<223> OTHER INFORMATION: Primer gus(Scop)-rev+PmlI

<400> SEQUENCE: 35
cggttacacg tgagcaccgg aagtaccgtt cccca                                  35

<210> SEQ ID NO 36
<211> LENGTH: 35
<212> TYPE: DNA
<213> ORGANISM: artificial
<220> FEATURE:
<223> OTHER INFORMATION: Primer gus(Pcan)-fwd+SpeI

<400> SEQUENCE: 36
catagcacta gtacacctgc agctcggcac tttcc                                  35

<210> SEQ ID NO 37
<211> LENGTH: 35
<212> TYPE: DNA
<213> ORGANISM: artificial
<220> FEATURE:
<223> OTHER INFORMATION: Primer gus(Pcan)-rev+PmlI

<400> SEQUENCE: 37
cggttacacg tgagcaccgg aagtaccgtt cccca                                  35
```

FUNGAL BETA-GLUCURONIDASE GENES AND GENE PRODUCTS

REFERENCE TO SEQUENCE LISTING

The present invention includes a Sequence Listing submitted on compact disc, the contents of which are incorporated by reference in their entirety.

TECHNICAL FIELD

The present invention relates generally to β-glucuronidases, more specifically to β-glucuronidase derived from fungal species, and uses of these β-glucuronidases.

BACKGROUND OF THE INVENTION

The enzyme β-glucuronidase (GUS; E.C.3.2.1.31) hydrolyzes a wide variety of glucuronides. Virtually any aglycone conjugated to D-glucuronic acid through a β-O-glycosidic linkage is a substrate for GUS. In vertebrates, glucuronides containing endogenous as well as xenobiotic compounds are generated through a major detoxification pathway and excreted in urine and bile.

*Escherichia coli*, the major organism resident in the large intestine of vertebrates, utilizes the glucuronides generated in the liver and other organs as an efficient carbon source. In *E. coli*, β-glucuronidase is encoded by the gusA gene (Novel and Novel, *Mol. Gen. Genet.* 120: 319–335, 1973), which is one member of an operon comprising two other protein-encoding genes: gusB encoding a permease (PER) specific for β-glucuronides, and gusC encoding an outer membrane protein (OMP) that facilitates access of glucuronides to the permease located in the inner membrane.

While β-glucuronidase activity is expressed in almost all tissues of vertebrates and their resident intestinal flora, GUS activity is absent in most other organisms. Notably, plants, many bacteria, and fungi have been reported to largely, if not completely, lack GUS activity. Thus, GUS is ideal as a reporter molecule in these organisms and has become the most widely used reporter system for plants.

In addition to use as a reporter molecule, GUS in combination with an innocuous glucuronide would be a preferred system to use for positive selection of transformed plants, especially for plants that will be consumed by humans. Because of the inefficiency of methods for transforming plant cells, only a small proportion of cells actually become transformed. Thus, it is desirable to select only those cells actually transformed. Typically, the selection methods involve transforming a cell with an antibiotic resistance gene along with the gene of interest and applying antibiotics to the cells, which kills the non-transformed cells.

Consumer resistance to antibiotic resistance genes has spurned research into alternative selection systems. Positive selection systems, wherein the transformed cells contain a gene whose gene product can utilize a compound that confers a growth advantage over the non-transformed cells. Ideally both the gene and the compound are biosafe to the environment and animals and humans.

GUS is the ideal system for positive selection for many reasons. First, biosafety assessment of GUS, including ecological and toxicological concerns, has shown GUS to be safe for both the environment and consumers (Gilissen et al. *Transgenic Res* 7: 157–163, 1998). Second, the gus gene is already present in several de-regulated food crops, such as papaya, beet and soybean, in the United States as well as in other countries. Third, the ease of making and isolating glucuronidated compounds allows a large choice of compounds to use for conferring growth advantage.

In positive selection systems under development, sugar compounds that plants do not normally metabolize, are being exploited in combination with xylose isomerase and mannose phosphate isomerase (U.S. Pat. Nos. 5,994,629 and 5,767,378). Unfortunately, both of these systems have disadvantages: mannose is toxic to plant cells, some plants have endogenous xylose isomerase activity, and neither of the genes have undergone biosafety testing. Moreover, a reporter gene must still be used for visualization of transformed cells, a procedure that is necessary for confirmation of transformation. In addition, the intellectual property for these two systems is held by Syngenta who so far has not granted commercial licenses on terms favorable for small companies.

The gus gene in combination with a sugar glucuronide would provide the best positive selection system. GUS can serve as both a selectable and a reporter molecule; it is biosafe; and glucuronide sugars, such as cellobiuronic acid (a disaccharide comprising glucose and glucuronic acid) are readily isolated inexpensively. The *E. coli* gus gene, however, does not metabolize cellobiuronic acid. Therefore, there is a need for a GUS enzyme that can cleave cellobiuronic acid.

The present invention provides gene and protein sequences of fungal β-glucuronidases and variants thereof that are secreted and cleave cellobiuronic acid, while providing other related advantages.

SUMMARY OF THE INVENTION

In one aspect, an isolated nucleic acid molecule is provided comprising a nucleic acid sequence encoding a fungal β-glucuronidase. The fungus is a member of the Eurotiomycetes or Sordariomycetes class. On the basis of rRNA sequences, various isolates of fungus expressing β-glucuronidase are identified as members of *Penicillium, Eupenicillium, Scopulariopsis, Aspergillus*, or *Gibberella* (anamorph *Fusarium*) genera. In one embodiment nucleic acid sequences are provided for β-glucuronidases from *Penicillium canescens, Aspergillus nidulans, Scopulariopsis* sp., and *Gibberella zeae* (anamorph *Fusarium graminearum*). Further, the nucleic acid sequences encoding β-glucuronidases of *Penicillium canescens* and *Scopulariopsis* are provided both with and without sequence encoding a signal sequence, which directs proteins to rough endoplasmic reticulum. Certain embodiments provide for variants of the nucleic acid sequence, which vary in nucleotide sequence as a result of natural polymorphisms, site-directed mutagenesis, codon optimization and the like.

In other aspects, expression vectors comprising a gene encoding a fungal α-glucuronidase or a portion thereof that has enzymatic activity in operative linkage with a heterologous promoter are provided. In the expression vectors, the heterologous promoter may be selected from the group consisting of a developmental type-specific promoter, a tissue type-specific promoter, a cell type-specific promoter and an inducible promoter. The promoter should be functional in the host cell for the expression vector. Examples of cell types include a plant cell, a bacterial cell, an animal cell and a fungal cell. In certain embodiments, the expression vector also comprises a nucleic acid sequence encoding a product of a gene of interest or portion thereof. The gene of interest may be under control of the same or a different promoter.

In other aspects, isolated fungal β-glucuronidase proteins are provided. Specific sequences are provided from *Penicillium, Eupenicillium, Scopulariopsis, Aspergillus,* or *Gibberella* (anamorph *Fusarium*) genera. In addition, β-glucuronidases from *Penicillium canescens* and *Scopulariopsis* are provided both with and without a signal sequence. Variants of the proteins are also provided. Methods to produce and purify the proteins of the present invention are described.

In another aspect, fusion proteins of a fungal β-glucuronidase or an enzymatically active portion thereof are provided. In certain embodiments, the fusion partner is a polypeptide chain of an antibody or fragment thereof that binds an antigen. Other fusion partners may be chosen to confer additional function or to facilitate purification of the β-glucuronidase protein.

The present invention also provides methods for monitoring expression of a gene of interest or a portion thereof in a host cell, comprising: (a) introducing into the host cell a vector construct, the vector construct comprising a nucleic acid molecule encoding a fungal β-glucuronidase of the present invention and a nucleic acid molecule encoding a product of the gene of interest or a portion thereof; (b) detecting the presence of the β-glucuronidase, thereby monitoring expression of the gene of interest. The fungal β-glucuronidases also have use in the present invention for confirming transformation of a host cell and for selecting transformed cells. In some preferred embodiments, the selecting compound is cellobiuronic acid, a disaccharide of glucose and glucuronic acid. In all these methods, a fungal glucuronide transport gene is optionally also introduced. These methods are especially useful in host cells that do not express an endogenous β-glucuronidase.

In another aspect, a method for providing an effector compound to a cell in a transgenic plant is provided. The method comprises (a) growing a transgenic plant that comprises an expression vector having a nucleic acid sequence encoding a fungal β-glucuronidase in operative linkage with a heterologous promoter and a nucleic acid sequence comprising a gene encoding a cell surface receptor for an effector compound and (b) exposing the transgenic plant to a glucuronide, wherein the glucuronide is cleaved by the β-glucuronidase, such that the effector compound is released. This method is especially useful for directing glucuronides to particular and specific cells by further introducing into the transgenic plant a vector construct comprising a nucleic acid sequence that binds the effector compound. The effector compound can then be used to control expression of a gene of interest by linking a gene of interest with the nucleic acid sequence that binds the effector compound.

Transgenic plants and animals, such as aquatic animals and insects, that express a fungal β-glucuronidase are also provided. The present invention also provides seeds of transgenic plants.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIGS. 2A–C present the DNA sequence (SEQ ID NO:1) and the deduced amino acid sequence (SEQ ID NO:2) of the gus gene of *Scopulariopsis* sp. isolate RP38.3.

FIGS. 3A–C present the DNA sequence (SEQ ID NO:3) and the deduced amino acid sequence (SEQ ID NO:4) of the gus gene of *Penicillium canescens* isolate RPK.

FIGS. 4A–C present the DNA sequence (SEQ ID NO:5) and the deduced amino acid sequence (SEQ ID NO:6) of the gus gene of *Penicillium canescens* strain DSM 1215.

FIG. 5 present the DNA sequence (SEQ ID NO:7) and the deduced amino acid sequence (SEQ ID NO:8) of the gus gene of *Gibberella zeae*.

FIG. 6 present the DNA sequence (SEQ ID NO:9) and the deduced amino acid sequence (SEQ ID NO:10) of the gus gene of *Aspergillus nidulans*.

FIGS. 7A–E present alignments of amino acid sequences of GUS proteins from *C. elegans* (SEQ ID NO:11), *D. melanogaster* (SEQ ID NO:12), *M. musculus* (SEQ ID NO:13), *R. norvegicus* (SEQ ID NO:14), *F. catus* (SEQ ID NO:15), *C. familiaris* (SEQ ID NO:16), *C. aethiops* (SEQ ID NO:17), *H. sapiens* (SEQ ID NO:18), *S. solfataricus* (SEQ ID NO: 19), *T. maritima* (SEQ ID NO:20), *L. gasseri* (SEQ ID NO:21), *E. coli* (SEQ ID NO:22), *Staphylococcus* sp. (SEQ ID NO:23), *A. nidulans* (SEQ ID NO:10), *P. canescens* (SEQ ID NO:4), *Scopulariopsis* sp. (SEQ ID NO:2), and *G. zeae* (SEQ ID NO:8).

DETAILED DESCRIPTION OF THE INVENTION

Figure 1:
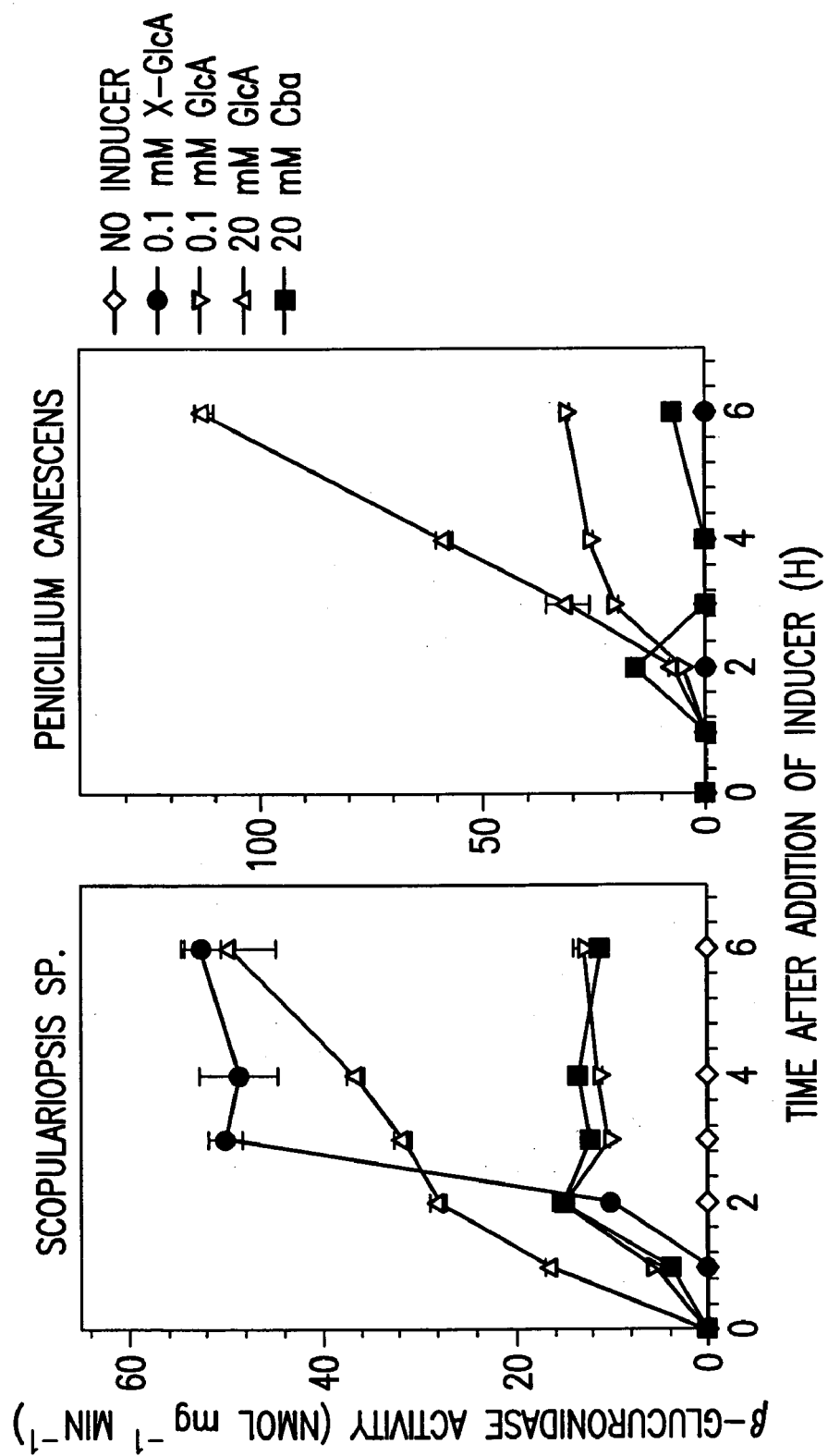
FIG. 1 shows the amount of GUS enzyme activity in two fungal species at various times after addition of different inducers.

Prior to setting forth the invention, it may be helpful to an understanding thereof to set forth definitions of certain terms that will be used hereinafter.

As used herein, "β-glucuronidase" refers to an enzyme that catalyzes the hydrolysis of β-glucuronides. Assays and some exemplary substrates for determining β-glucuronidase activity, also referred to herein as GUS activity, are provided in U.S. Pat. No. 5,268,463. Other assays and substrates are taught in *GUS Protocols: Using the GUS gene as a reporter of gene expression* (ed. Gallagher S R, Academic Press, 1992, 221 pp.) In assays to detect β-glucuronidase activity, fluorogenic or chromogenic substrates are preferred. Such substrates include, but are not limited to, p-nitrophenyl β-D-glucuronide and 4-methylumbelliferyl β-D-glucuronide.

As used herein, the enzyme may be alternatively referred to as GUS or β-glucuronidase. The nucleic acid sequence that encodes GUS is referred to as gus. gus genes from particular species are written either as, for example, *E. coli* gus or preferably gus$^{Eco}$. If the gus gene is from an organism in which the genus is identified but the species is not, the superscript will use the first letters of the genus name.

As used herein, a "glucuronide" or "β-glucuronide" refers to an aglycone conjugated in a hemiacetal linkage, typically through the hydroxyl group, to the C1 of a free D-glucuronic acid in the β configuration. Glucuronides include, but are not limited to, O-glucuronides linked through an oxygen atom, S-glucuronides, linked through a sulfur atom, N-glucuronides, linked through a nitrogen atom and C-glucuronides, linked through a carbon atom (see, Dutton, *Glucuronidation of Drugs and Other Compounds*, CRC Press, Inc. Boca Raton, Fla. pp 13–15). β-glucuronides consist of virtually any compound linked to the C1-position of glucuronic acid as a beta anomer, and are typically, though by no means exclusively, found as an O-glycoside. β-glucuronides are produced naturally in most vertebrates through the action of UDP-glucuronyl transferase as a part of the process of solubilizing, detoxifying, and mobilizing both natural and xenobiotic compounds, thus directing them to sites of excretion or activity through the circulatory system.

β-glucuronides in polysaccharide form are also common in nature, most abundantly in vertebrates, where they are major constituents of connective and lubricating tissues in polymeric form with other sugars such as N-acetylglucosamine (e.g., chondroitin sulfate of cartilage, and hyaluronic acid, which is the principle constituent of synovial fluid and mucus). Other polysaccharide sources of β-glucuronides occur in bacterial cell walls, e.g., cellobiuronic acid. β-glucuronides are relatively uncommon or absent in plants. Glucuronides and galacturonides found in plant cell wall components (such as pectin) are generally in the alpha configuration, and are frequently substituted as the 4-O-methyl ether; hence, such glucuronides are not substrates for β-glucuronidase.

As used herein, a "variant" of gus or GUS is a nucleotide or amino acid sequence that contains one or more differences compared to the native sequence. Variants may arise naturally, e.g., polymorphisms, or be generated by in vivo or in vitro methods, a variety of these methods are described herein. Variants will have one or more amino acid or nucleotide alterations, one or more insertions, and/or one or more deletions.

As used herein, "percent sequence identity" is a percentage determined by the number of exact matches of amino acids or nucleotides to a reference sequence divided by the number of residues in the region of overlap. Within the context of this invention, preferred amino acid or nucleotide sequence identity for a variant of GUS is at least 75% and preferably greater than 80%, 85%, 90%, 95%, or 97%. Sequence identity may be determined by standard methodologies, including use of the National Center for Biotechnology Information BLAST search methodology available at www.ncbi.nlm.nih.gov. The identity methodologies preferred are non-gapped BLAST. However, those described in U.S. Pat. No. 5,691,179 and Altschul et al., *Nucleic Acids Res.* 25: 3389–3402, 1997, all of which are incorporated herein by reference, are also useful. Accordingly, if gapped BLAST 2.0 is utilized, then it is utilized with default settings.

As will be appreciated by those skilled in the art, a nucleotide sequence encoding fungal GUS may differ from wild-type sequences presented in the Figures, due to codon degeneracy, nucleotide polymorphisms, or amino acid differences. In certain embodiments, variants will hybridize to the wild-type nucleotide sequence at conditions of normal stringency, which is approximately 25–30° C. below Tm of the native duplex (e.g., 1 M Na+ at 65° C.; e.g. 5×SSPE, 0.5% SDS, 5× Denhardt's solution, at 65° C. or equivalent conditions; see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987). Alternatively, the Tm can be calculated by the formula Tm=81.5+0.41%(G+C)−log[Na+]. Low stringency hybridizations are performed at conditions approximately 40° C. below Tm, and high stringency hybridizations are performed at conditions approximately 10° C. below Tm. Conditions suitable for hybridization of short nucleic acid molecules (less than about 500 bp) can be found in the references above. Note that some nucleic acid variants may not hybridize to the reference sequence because of codon degeneracy, such as degeneracy introduced for codon optimization in a particular host, in which case amino acid identity may be used to assess similarity of the variant to the native protein.

An "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, have protein backbones (e.g., PNA) or some combination of these. Similarly, an "isolated protein" refers to a protein that has been separated from its source cell.

Fungal β-Glucuronidase Genes

As noted above, this invention provides gene sequences and gene products of fungal β-glucuronidases. As exemplified herein, genes from fungi, including the Eurotiomycetes and Sordariomycetes classes, that encode a β-glucuronidase are identified and characterized biochemically, genetically, and by DNA sequence analysis. Exemplary β-glucuronidase genes and their gene products from several genera, including *Penicillium*, *Scopulariopsis*, *Aspergillus*, and *Gibberella*, are provided herein. β-glucuronidase genes from additional fungi species may be identified as described herein or by hybridization of one of the fungal gus gene sequences to genomic or cDNA libraries, by genetic complementation, by function, by amplification, by antibody screening of an expression library and the like (see Sambrook et al., supra Ausubel et al., supra for methods and conditions appropriate for isolation of a β-glucuronidase from other species).

The presence of a fungal β-glucuronidase gene may be observed by a variety of methods and procedures. Particularly useful screens for identifying β-glucuronidase are biochemical screening for the gene product, genetic complementation, and sequence analysis comparisons.

Test samples containing fungi may be obtained from sources such as soil, plant surfaces, animal or human skin, decomposing matter, and the like. Fungal isolates are generally obtained by plating the sample (e.g., soil extract) on a suitable substrate in appropriate conditions. Conditions and substrates will vary according to the growth requirements of the fungus and the selecting compound. For example, when it is desirable to isolate fungi expressing a β-glucuronidase that cleaves cellobiuronic acid, samples are plated on minimal medium supplemented with vitamin and microelement solutions and with cellobiuronic acid as the sole carbon source.

Cellobiuronic acid (Cba) is the name by which the disaccharide having the following structure (I) is commonly known:

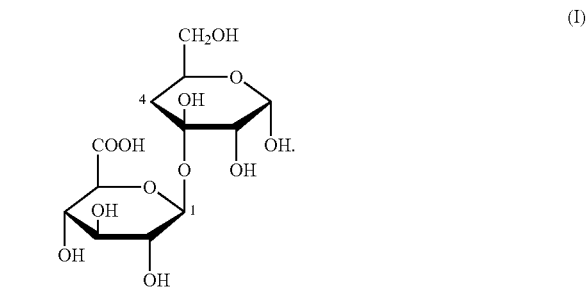

(I)

In the literature, the disaccharide of structure (I) is sometimes referred to by other names, including cellobiuronic acid, 4-O-(β-D-glucopyranuronosyl)-D-glucose, and β-glucuronosyl[1–4]glucose). See, e.g., Carbohydrates, P. M. Collins, ed. Chapman and Hall, page 117, 1987. Regardless of the name, as shown in structure (I), cellobiuronic acid is a disaccharide formed between D-glucopyranuronic acid in β-linkage to a D-glucose, where the β-linkage is through carbon number 1 of D-glucopyranuronic acid and carbon number 4 of glucose (as identified in the structure (I)). A β linkage from a glucuronic acid to another sugar moiety (as seen in cellobiuronic acid) is referred to herein as a β-glucuronide linkage.

Other selective compounds can be used. Other saccharides or compounds required for growth of fingi that are in β linkage with a glucuronic acid may be used. Alternatively, the selecting molecule can be an S-glucuronide, linked through a sulfur atom, an N-glucuronide, linked through a nitrogen atom or a C-glucuronide, linked through a carbon atom to a saccharide or other compound required for cellular growth. Whatever the selecting glucuronide, fungi that express a β-glucuronidase may be identified by a glucuronide substrate that is readily detectable when cleaved by β-glucuronidase. If GUS enzymatic activity is present, the fungi will stain; a diffuse staining (halo) pattern surrounding a colony suggests that GUS is secreted.

The samples may contain bacteria or other microbes in addition to fungi. Some of these other microbes may have β-glucuronidase activity. Adhering bacteria or other microbes can be removed by consecutive sub-cultivation on medium containing antibiotics, such as ampicillin, streptomycin and nalidixic acid. Substrates such as deoxycholate, citrate, etc. may be used to inhibit other extraneous and undesired organisms such as gram-positive cocci and spore forming bacilli.

Following purification of the candidate fungi, it is prudent to verify GUS activity and cleavage of the selecting glucuronide by any of a number of different assays. In the Examples, the fungi were purified on YPD medium containing ampicillin, streptomycin and nalidixic acid and subsequently transferred back to the minimal medium containing Cba to reconfirm GUS activity by growth of the fungi. Alternatively, or in addition, a chromogenic assay for GUS activity can readily be performed by adding X-GlcA (5-bromo-4-chloro-3-indolyl-β-D-glucuronide) to the medium and observing whether a blue precipitate forms.

Other assays include in vitro biochemical assays, such as hydrolysis of a GUS substrate. Suitable GUS substrates are commercially available and widely known (see, U.S. Pat. No. 5,268,463 and GUS Protocols (supra) for details of substrates and assays.] For example, hydrolysis of 4-methylumberlliferyl-β-D-glucuronide (MU-GlcA), a widely used GUS substrate, can be measured in vitro. For this assay, fungal isolates are grown and hyphal aggregates collected by e.g. vacuum filtration, washed and resuspended in minimal medium lacking glucuronides. Following a period of starvation, various inducers of GUS activity (e.g. glucuronides) are added for an incubation time period. Aliquots of hyphal aggregates are collected at time intervals and proteins are extracted from these. The amount of cleavage of MU-GlcA by the test and control protein extracts are quantified, thereby confirming GUS activity.

A genetic complementation assay may be additionally performed to verify that the staining pattern is due to expression of a gus gene or to assist in isolating and cloning the gus gene. Briefly, in this assay, the candidate gus gene is transfected into an *E. coli* strain that is deleted for the gus operon (e.g., KW1 described herein), and the staining pattern of the transfectant is compared to a mock-transfected host. Fungal genomic DNA, fungal cDNA, or an isolated gus gene is digested by e.g., restriction enzyme reaction and ligated to a vector, which ideally is an expression vector. The recombinants are then transfected into a host strain, which preferably lacks or is deleted for any endogenous gus genes (e.g., KW1 or a recA⁻ deletion of KW1, called JEMA99.9). In some cases, the host strain may express the gus gene but preferably not in the compartment to be assayed. The transfected cells are selected on medium supplemented with an inducer of the gus gene. In the Examples, the fungal gus genes are cloned into a bacterial expression vector under control of the LAC promoter, expression of the gus gene is induced by IPTG (isopropyl-β-D-thiogalactoside), and β-glucuronidase activity is detected with X-GlcA. If GUS activity is present, the bacteria will turn blue; bacteria transfected with the vector alone will remain white. Moreover, if GUS is secreted, the transfectant should exhibit a diffuse staining pattern (halo) surrounding the colony.

The genera and species of the GUS-expressing fungi can be identified in myriad ways, including morphology, sequence similarity, metabolism signatures, and the like. A preferred method is comparison of rRNA sequence to sequences determined from known fungal genera or species. The rRNA sequences are generally obtained by sequencing of amplified fragments of genomic DNA. In fungal species, the 5.8S rRNA gene flanked by intergenic transcribed spacers 1 and 2 (ITS1, ITS2) have highly variable sequences and thus are well suited for identification of fungi. Preferably the match is at least 90%, at least 95%, or at least 99%. If no perfect match, or near perfect match, with a known species is found or if additional confirmation is desirable, sequence obtained of the 18S rRNA gene is compared to a database of fungal 18S rRNA sequences to establish the phylogenetic placement at the genus level. Nucleotide identity is preferably at least 90%, at least 95%, or at least 99%. For either of these rRNA sequences, a suitable method to obtain sequence is to amplify the genes using primers that derive from conserved regions and subject the amplified fragments to DNA sequence analysis. Other methods to isolated and determine sequence rRNA gene regions are well known. Occasionally fungal species represented in the databases may be renamed or reclassified in a different genus. In such cases, other of these fungi, which are isolated and characterized, such as those herein, will also change accordingly.

In exemplary screens, three isolates of fungi that can utilize Cba as a carbon source and have GUS activity are obtained from soil samples. Confirmation of GUS activity is established by biochemical assay and growth of purified fungi on medium containing Cba. rRNA sequence analyses and comparison to other eukaryotic rRNA genes identified the fungi as *Penicillium canescens* and *Scopulariopsis* sp.

The fungal gus gene can be isolated by any number of methods. For example, it can be cloned by inserting genomic DNA or cDNA fragments into an expression vector and looking for complementation in a gus deletion strain. The vector with the insert is then recovered by isolation or the insert is amplified and recovered. Another method is to amplify the gus gene from genomic DNA or cDNA using primers derived from conserved areas of known gus genes from bacteria and animals. In the Examples, a 1.2 kb signature fragment of the gus gene is amplified from fungal DNA from the three isolates. The complete nucleotide sequences of the gus genes, including upstream and downstream non-coding sequences are obtained by amplification, but could be isolated in other ways such as using the 1.2 kb fragment as a probe against a genomic library or a cDNA library. Other well-known methods can alternatively be used.

Figure 3B:
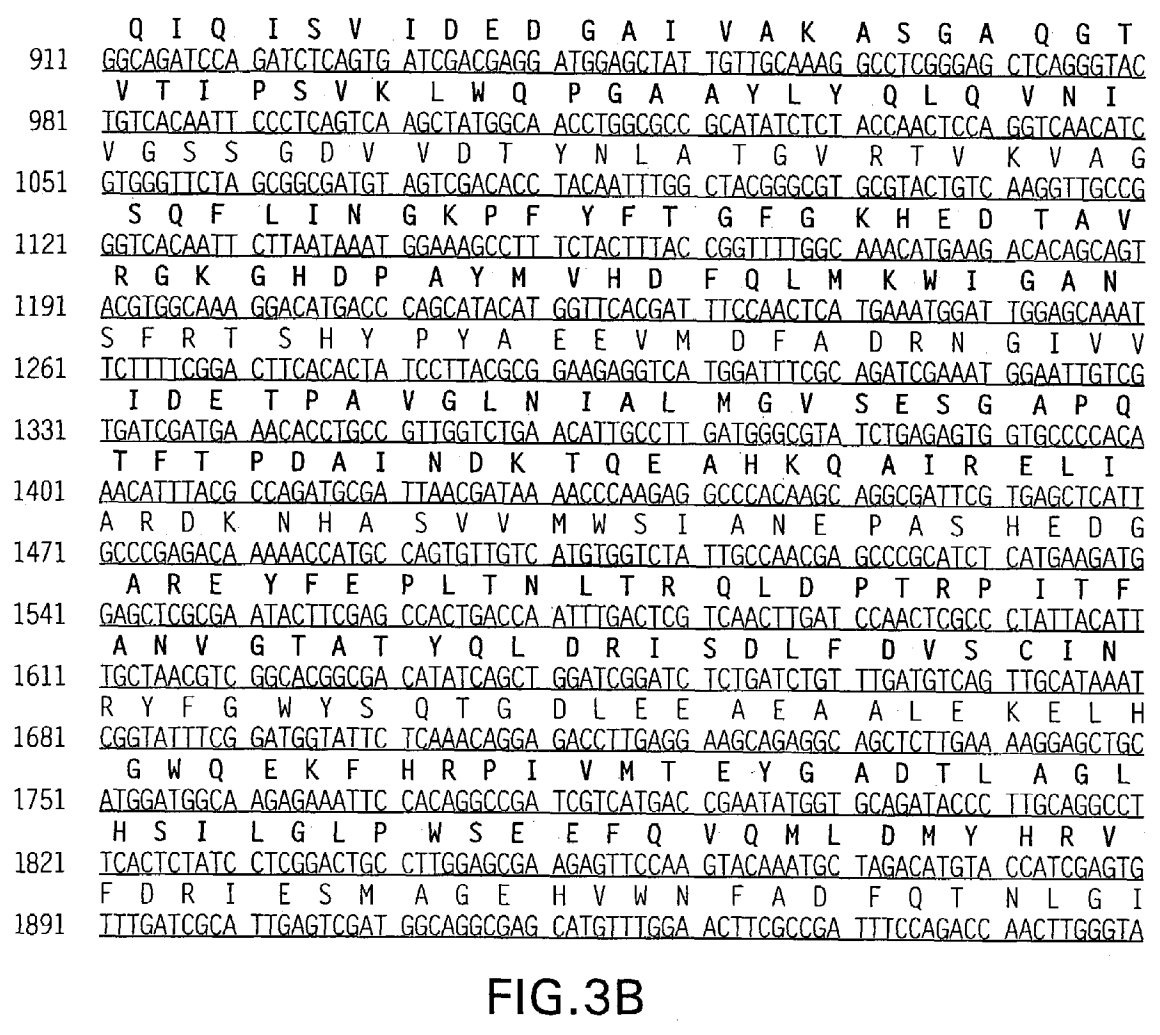

DNA sequences of the gus gene contained in these three isolates are presented in FIGS. 2–4 and as SEQ ID NOs:1, 3, and 5. Translation of a continuous open reading frame reveals a 641 amino acid (*Scopulariopsis*) protein and a 634 amino acid protein (*P. canescens*). Furthermore, there appears to be signal peptides with predicted cleavage positions at amino acids 26–27 (*Scopulariopsis*) and 18–19 (*P. canescens*), which would then yield mature proteins of 615 and 616 amino acids, respectively.

Confirmation that the ORFs encode β-glucuronidases is made by sequence similarity between the predicted fungal protein sequences and bacterial and animal GUS protein sequences. As demonstrated herein, there is significant similarity to microbial and mammalian β-glucuronidases. Furthermore, it is confirmed that conserved domains and signature sequences common to family 2 glycosyl hydrolases (e.g., β-glucuronidase) are present in fungal β-glucuronidases (FIGS. 7A–D). The amino acid sequences are shown in alignment in FIGS. 7A–D. The signature peptide sequences for family 2 glycosyl hydrolases (Henrissat, *Biochem Soc Trans* 26: 153, 1998; Henrissat B et al., *FEBS Lett* 27: 425, 1998) are located from amino acids 423 to 448 and from amino acids 498 to 512 (consensus numbering in FIGS. 7A–D). The acid/base catalyst is Glu 512 (consensus numbering) and the catalytic nucleophile (proton donor) is Glu 608 (Wong et al., *J. Biol. Chem.* 18: 34057, 1998). Overall identity (similarity) between *Scopulariopsis* and *E. coli* GUS proteins is 49.6% (60.5%), between *Penicillium* and *E. coli* is 50.3% (61.6%). Identity at the DNA level is 55.3% (between *Scopulariopsis* and *E. coli*) and 50.8% (between *Penicillium* and *E. coli*).

There are four Asn-Xaa-Ser/Thr sequences in *Penicillium* and five Asn-Xaa-Ser/Thr sequences in *Scopulariopsis* that may serve as site for N-glycosylation in the ER. Furthermore, unlike the *E. coli* and human β-glucuronidases, which have 9 and 4 cysteines respectively, these GUS proteins have two Cys residues.

Additional fungi that have a gus gene can be identified by any of the methods described herein or by interrogation of sequences in a database. In the Examples, two additional gus genes are identified in a publicly available dataset. The gus genes are found in *Aspergillus nidulans* and *Gibberella zeae*. The gus gene sequences from these species and from other fungal species can be isolated as described herein, e.g., amplification using primers derived from conserved regions or from sequences of the genes as published in a database, by hybridization of genomic or cDNA libraries with a known gus sequence, and the like.

In certain aspects, the present invention provides fragments of fungal gus genes. A fragment is any length sequence. Fragments of fungal gus may be isolated or constructed for use in the present invention. For example, restriction fragments can be isolated by well-known techniques from template DNA, e.g., plasmid DNA, and DNA fragments, including, but not limited to, digestion with restriction enzymes or amplification. These fragments may be used in hybridization methods (see, exemplary conditions described infra) or inserted into an appropriate vector for expression or production. In other embodiments, oligonucleotides (two or more nucleotides) of fungal GUSes are provided especially for use as amplification primers. In such case, the oligonucleotides are at least 12 bases and preferably at least 15 bases (e.g., at least 18, 21, 25, 30 bases) and generally not longer than 50 bases. It will be appreciated that any of these fragments described herein can be double-stranded, single-stranded, derived from coding strand or complementary strand and be exact or mismatched sequence.

Other fragments (oligonucleotides) for use in this invention may be at least 12 nucleotides long (e.g., at least 15 nt, 17 nt, 20 nt, 25 nt, 30 nt, 40 nt, 50 nt, 100 nt, 150 nt, 200 nt and so on). One skilled in the art will appreciate that other methods are available to obtain DNA or RNA molecules having at least a portion of a fungal gus sequence. Other uses for fragments include hybridization and isolation of new fungal gus genes, amplification, site-directed mutagenesis and the like. Moreover, for particular applications, these nucleic acids may be labeled by techniques known in the art, such as with a radiolabel (e.g., $^{32}P$, $^{33}P$, $^{35}S$, $^{125}I$, $^{131}I$, $^{3}H$, $^{14}C$), fluorescent label (e.g., FITC, Cy5, RITC, Texas Red), chemiluminescent label, enzyme, biotin and the like.

In certain aspects, the fragments have sequences of one or both of the signatures or have sequence from at least some of the more highly conserved regions of GUS (e.g., from approximately amino acids 423 to 448 and from amino acids 498 to 512 based on the consensus numbering in FIG. 7A–E). In the various embodiments, useful fragments comprise those nucleic acid sequences which encode at least the glutamate residue that acts as the acid/base catalyst (amino acid position 512) and the glutamate residue that acts as the catalytic nucleophile at position 608 (consensus numbering in FIG. 7A–E).

Fungal β-Glucuronidase Gene Products

The present invention also provides β-glucuronidase gene products in various forms. Forms of GUS protein include, but are not limited to, secreted forms, membrane-bound forms, cytoplasmic forms, fusion proteins, chemical conjugates of GUS and another molecule, portions of GUS protein, and other variants. GUS protein may be produced by expression from a recombinant vector, biochemical isolation from natural sources such as hyphae, from transformed host cells, and the like.

In certain aspects, variants of secreted fungal GUS are useful within the context of this invention. Variants include nucleotide or amino acid substitutions, deletions, insertions, and chimeras (e.g., fusion proteins). Typically, when the result of synthesis, amino acid substitutions are conservative, i.e., substitution of amino acids within groups of polar, non-polar, aromatic, charged, etc. amino acids.

Variants may be constructed by any of the well known methods in the art (see, generally, Ausubel et al., supra; Sambrook et al., supra). Such methods include site-directed oligonucleotide mutagenesis, restriction enzyme digestion and removal or insertion of bases, amplification using primers containing mismatches or additional nucleotides, splicing of another gene sequence to the native fungal gus gene, synthesis and the like. Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. Similarly, deletions and/or insertions may be constructed by any of a variety of known methods. For example, the gene can be digested with restriction enzymes and religated such that some sequence is deleted or ligated with an isolated fragment having cohesive ends so that an insertion or large substitution is made. In other embodiments, variants are generated by shuffling of regions (see U.S. Pat. No. 5,605,793) or by "molecular evolution" techniques (see U.S. Pat.

No. 5,723,323). Other means to generate variant sequences may be found, for example, in Sambrook et al. (supra) and Ausubel et al. (supra).

In addition to directed mutagenesis in which one or a few amino acids are altered, variants that have multiple substitutions may be generated. The substitutions may be scattered throughout the protein or functional domain or concentrated in a small region. For example, a region may be mutagenized by oligonucleotide-directed mutagenesis in which the oligonucleotide contains a string of dN bases or the region is excised and replaced by a string of dN bases. Thus, a population of variants with a randomized amino acid sequence in a region is generated. The variant with the desired properties (e.g., more efficient secretion) is then selected from the population.

Verification of variant sequences is typically accomplished by restriction enzyme mapping, sequence analysis, and/or probe hybridization, although other methods may be used. The double-stranded nucleic acid is transformed into host cells, typically E. coli, but alternatively, other prokaryotes, yeast, or larger eukaryotes may be used. Standard screening protocols, such as nucleic acid hybridization, amplification, and DNA sequence analysis, can be used to identify mutant sequences.

In preferred embodiments, the protein and variants are capable of being secreted and cleaving Cba. A GUS protein is secreted if the amount of secretion expressed as a secretion index is statistically significantly higher for the candidate protein compared to a standard, typically E. coli GUS. The secretion index may be calculated as the percentage of total GUS activity in periplasm or other extracellular environment less the percentage of total β-glucuronidase activity found in the same extracellular environment for a non-secreted GUS. Cleavage of Cba can be determined in vitro, e.g., by thin layer chromatography, or in vivo, e.g., survival of transformed cells on Cba as sole carbon source.

In other embodiments, variants may be directed to other cellular compartments, such as membrane or cytoplasm. Membrane-spanning amino acid sequences are generally hydrophobic and many examples of such sequences are well-known. These sequences may be spliced onto fungal secreted GUS by a variety of methods including conventional recombinant DNA techniques. Similarly, sequences that direct proteins to cytoplasm (e.g., Lys-Asp-Glu-Leu) may be added to the reference GUS, typically by recombinant DNA techniques.

In other embodiments, variants of fungal GUS are capable of binding to a hapten, such as biotin, dinitrophenol, and the like. Binding assays to such haptens are well known and may be found, for example, in *Antibodies: A Laboratory Manual* (infra).

In other embodiments, a fusion protein comprising GUS may be constructed from the nucleic acid molecule encoding fungal gus and one or more other nucleic acid molecules. As will be appreciated, the fusion partner gene may contribute, within certain embodiments, an open reading frame. In preferred embodiments, fungal GUS is fused to avidin, streptavidin or one of the polypeptides of an antibody. Thus, it may be desirable to use only the catalytic region of GUS (e.g., the region containing the two well-defined catalytically active amino acid residues plus optionally the conserved family 2 signatures). The choice of the fusion partner depends in part upon the desired application. The fusion partner may be used to alter specificity of GUS, provide a reporter function, provide a tag sequence for identification or purification protocols, and the like. The reporter or tag can be any protein or peptide that allows convenient and sensitive measurement or facilitates isolation of the gene product and does not interfere with the function of GUS. For example, green fluorescent protein and β-galactosidase are readily available as DNA sequences and may be used to provide additional function to GUS. A peptide tag is a short sequence, usually derived from a native protein, which is recognized by an antibody, hapten, or other molecule. Peptide tags include, but are not limited to, FLAG®, Glu-Glu tag (Chiron Corp., Emeryville, Calif.), KT3 tag (Chiron Corp.), T7 gene 10 tag (Invitrogen, La Jolla, Calif.), T7 major capsid protein tag (Novagen, Madison, Wis.), $His_6$ (hexa-His), and HSV tag (Novagen). Besides these tags, other proteins or peptides, such as glutathione-S-transferase may be used as a tag.

In other aspects of the present invention, isolated fungal glucuronidase proteins are provided. In one embodiment, GUS protein is expressed as a hexa-His fusion protein and isolated by metal-affinity chromatography, for example using nickel-coupled beads. Briefly, a sequence encoding $His_6$ is linked to a DNA sequence encoding a GUS. Although the $His_6$ sequence can be positioned anywhere in the molecule, it is typically linked at the 3' end immediately preceding the termination codon. The hexa-His-GUS fusion may be constructed by any of a variety of methods. A convenient method is amplification of the gus gene using a downstream primer that contains the codons for $His_6$. Alternatively, the gus gene may be cloned into a vector that already contains the $His_6$ coding sequence.

Alternatively, β-glucuronidase protein, with or without a tag, may be isolated by standard methods, such as affinity chromatography using matrices containing saccharo-lactone, phenyl-thio-β-glucuronide, antibodies to GUS protein and the like, size exclusion chromatography, ionic exchange chromatography, HPLC, and other known protein isolation methods (see generally Ausubel et al. supra; Sambrook et al. supra). The protein can be expressed as a hexa-His fusion protein and isolated by metal-affinity chromatography, for example with nickel-coupled beads. An isolated purified protein gives a single band on SDS-PAGE when stained with Coomassie brilliant blue.

In one aspect of the present invention, peptides having fungal GUS sequence are provided. Peptides may be used as immunogens to raise antibodies, as well as other uses, such as competitive inhibitors in assays. Peptides are generally five to 100 amino acids long, and more usually 10 to 50 amino acids. Peptides are readily chemically synthesized in an automated fashion (e.g., PerkinElmer, ABI Peptide Synthesizer) or may be obtained commercially. Peptides may be further purified by a variety of methods, including high-performance liquid chromatography (HPLC). Furthermore, peptides and proteins may contain amino acids other than the 20 naturally occurring amino acids or may contain derivatives and modification of the amino acids.

Antibodies to Fungal GUS

Antibodies to fungal GUS proteins, fragments, or peptides discussed herein may readily be prepared. Such antibodies may specifically recognize reference fungal GUS protein and not a variant protein, or variant protein and not wild type protein, or equally recognize both the mutant (or variant) and wild-type forms. Antibodies may be used for isolation of the protein, inhibiting activity of the protein (antagonist), or enhancing activity of the protein (agonist).

Within the context of the present invention, antibodies are understood to include monoclonal antibodies, polyclonal antibodies, anti-idiotypic antibodies, antibody fragments (e.g., Fab, and $F(ab')_2$, $F_v$ variable regions, or complementarity determining regions). Antibodies are generally accepted as specific against GUS protein if they bind with a $K_d$ of greater than or equal to $10^{-7}$ M, preferably greater than of equal to $10^{-8}$ M. The affinity of a monoclonal antibody or binding partner can be readily determined by one of ordinary skill in the art (see Scatchard, *Ann. N.Y. Acad. Sci.* 51: 660–672, 1949).

Briefly, a polyclonal antibody preparation may be readily generated in a variety of warm-blooded animals such as rabbits, mice, or rats by well-known procedures. Monoclonal antibodies may be readily generated from hybridoma cell lines using conventional techniques (see U.S. Pat. Nos. RE 32,011, 4,902,614, 4,543,439, and 4,411,993; see also *Antibodies: A Laboratory Manual*, Harlow and Lane (eds.), Cold Spring Harbor Laboratory Press, 1988). Other techniques may also be utilized to construct monoclonal antibodies (see Huse et al., *Science* 246: 1275–1281, 1989; Sastry et al., *Proc. Natl. Acad. Sci. USA* 86: 5728–5732, 1989; Alting-Mees et al., *Strategies in Molecular Biology* 3: 1–9, 1990; describing recombinant techniques).

One of ordinary skill in the art will appreciate that a variety of alternative techniques for generating antibodies exist. In this regard, the following U.S. patents teach a variety of these methodologies and are thus incorporated herein by reference: U.S. Pat. Nos. 5,840,479; 5,770,380; 5,204,244; 5,482,856; 5,849,288; 5,780,225; 5,395,750; 5,225,539; 5,110,833; 5,693,762; 5,693,761; 5,693,762; 5,698,435; and 5,328,834.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC (e.g., reversed phase, size exclusion, ion-exchange), purification on protein A or protein G columns, or any combination of these techniques.

Assays for Function of β-Glucuronidase

In preferred embodiments, fungal β-glucuronidases will at least have enzymatic activity and in other preferred embodiments, will also have the capability of being secreted. As noted above, variants of these reference GUS proteins may exhibit altered functional activity and cellular localization. Enzymatic activity may be assessed by assays such as the ones disclosed herein or in U.S. Pat. No. 5,268,463 (Jefferson). Generally, a chromogenic or fluorogenic substrate is incubated with cell extracts, tissue or tissue sections, or purified protein. Cleavage of the substrate is monitored by a method appropriate for the aglycone or the glucuronic acid that is released.

A variety of methods may be used to demonstrate that a β-glucuronidase is secreted. For example, a rapid screening method in which colonies of organisms or cells, such as bacteria, yeast or insect cells, are plated and incubated with a readily visualized glucuronide substrate, such as X-GlcA. A colony with a diffuse staining pattern likely secretes GUS, although such a pattern could indicate that the cell has the ability to pump out the aglycone or its dimer, that the cell has become leaky, or that the enzyme is membrane bound. These unlikely alternatives can be ruled out by using a host cell for transfection that does not pump out the aglycone chosen and lacks an endogenous gus gene.

Secretion of the enzyme may be verified by assaying for GUS activity in the extracellular environment. If the cells secreting GUS are gram-positive bacteria, yeasts, molds, plants, or other organisms with cell walls, activity may be assayed in the culture medium and in a cell extract, however, the protein may not be transported through the cell wall. Thus, if no or low activity of a secreted form of GUS is found in the culture medium, protoplasts are prepared by osmotic shock or enzymatic digestion of the cell wall or any other suitable procedure, and the supernatant is assayed for GUS activity. If the cells secreting GUS are gram-negative bacteria, the culture supernatant is tested, but β-glucuronidase may be retained in the periplasmic space between the inner and outer membrane. In this case, spheroplasts are prepared by osmotic shock, enzymatic digestion, or any other suitable procedure, and the supernatant is assayed for GUS activity. Cells without cell walls are assayed for GUS in cell supernatant and cell extract. The fraction of activity in each compartment is compared to the activity of a non-secreted GUS in the same or similar host cells. A β-glucuronidase is secreted if significantly more enzyme activity than *E. coli* GUS activity is found in extracellular spaces. The amount of secretion is generally normalized to the amount of a non-secreted protein (e.g., β-galactosidase) found in intracellular spaces. By this assay, usually less than 10% of *E. coli* GUS is secreted. Within the context of this invention, higher amounts of secreted enzyme are preferred (e.g., greater than 20%, 25%, 30%, 40%, 50%).

β-glucuronidases that exhibit particular substrate specificity are also useful within the context of the present invention. As noted above, glucuronides can be linked through an oxygen, carbon, nitrogen or sulfur atom. Glucuronide substrates having each of the linkages may be used in one of the assays described herein to identify GUSes that discriminate among the linkages. In addition, various glucuronides containing a variety of aglycones may be used to identify GUSes that discriminate among the aglycones.

Vectors, Host Cells and Means of Expressing and Producing Protein

Fungal β-glucuronidase may be expressed in a variety of host organisms. For protein production and purification, GUS is preferably secreted and produced in bacteria, such as *E. coli*, for which many expression vectors have been developed and are available. Other suitable host organisms include other bacterial species (e.g., *Bacillus*), and eukaryotes, such as yeast (e.g., *Saccharomyces cerevisiae*), mammalian cells (e.g., CHO and COS-7), plant cells and insect cells (e.g., Sf9). Vectors for these hosts are well known.

A DNA sequence encoding a fungal β-glucuronidase is introduced into an expression vector appropriate for the host. The sequence is derived from an existing clone or synthesized. As described herein, a fragment of the coding region may be used, but if enzyme activity is desired, the catalytic region should be included. A preferred means of synthesis is amplification of the gene from cDNA, genomic DNA, or a recombinant clone using a set of primers that flank the coding region or the desired portion of the protein. Restriction sites are typically incorporated into the primer sequences and are chosen with regard to the cloning site of the vector. If necessary, translational initiation and termination codons can be engineered into the primer sequences. The sequence of GUS can be codon-optimized for expression in a particular host. For example, a secreted form of β-glucuronidase isolated from a bacterial species that is expressed in a fungal host, such as yeast, can be altered in nucleotide sequence to use codons preferred in yeast. Codon-optimization may be accomplished by methods such as splice overlap extension, site-directed mutagenesis, automated synthesis, and the like.

At minimum, an expression vector must contain a promoter sequence. Other regulatory sequences may be included. Such sequences include a transcription termination signal sequence, secretion signal sequence, intron, enhancer, origin of replication, selectable marker, and the like. The regulatory sequences are operationally associated with one another to allow transcription or translation.

Suitable host cells may be prokaryotic or eukaryotic. The most commonly used bacteria is *E. coli*, but any transformable bacteria may alternatively be used. Eukaryotic cells useful in this invention include, but are not limited to, yeast cells, plant cells, mouse cells, and human cells. A host cell may be cells that grow as isolated cells or may be an organized collection of cells, such as meristem tissue, callus tissue or other explanted tissue from plants. Human organisms are specifically excluded from host cells, although isolated human cells may be used.

Expression in Bacteria

The plasmids used herein for expression of secreted GUS include a promoter designed for expression of the proteins in a bacterial host. Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, RSV LTR, SV40, metallothionein promoter (see, e.g., U.S. Pat. No. 4,870,009) and other inducible promoters. For protein expression, a promoter is inserted in operative linkage with the coding region for β-glucuronidase.

The promoter controlling transcription of β-glucuronidase may be controlled by a repressor. In some systems, the promoter can be de-repressed by altering the physiological conditions of the cell, for example, by the addition of a molecule that competitively binds the repressor, or by altering the temperature of the growth media. Preferred repressor proteins include, but are not limited to the *E. coli* LACI repressor responsive to IPTG induction, the temperature sensitive λcI857 repressor, and the like. The *E. coli* LACI repressor is preferred.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

Preferably, the vector is capable of replication in host cells. Thus, for bacterial hosts, the vector preferably contains a bacterial origin of replication. Preferred bacterial origins of replication include the fl-ori and col E1 origins of replication, especially the origin derived from pUC plasmids.

The plasmids also preferably include at least one selectable gene that is functional in the host. A selectable gene includes any gene that confers a phenotype on the host that allows transformed cells to be identified and selectively grown. Suitable selectable marker genes for bacterial hosts include the ampicillin resistance gene ($Amp^r$), tetracycline resistance gene ($Tc^r$) and kanamycin resistance gene ($Kan^r$). Suitable markers for eukaryotes usually complement a deficiency in the host (e.g., thymidine kinase (tk) in tk-hosts). However, drug markers are also available (e.g., G418 resistance and hygromycin resistance).

The sequence of nucleotides encoding β-glucuronidase may also include a classical secretion signal, whereby the resulting peptide is a precursor protein processed and secreted. The resulting processed protein may be recovered from the periplasmic space or the fermentation medium. Secretion signals suitable for use are widely available and are well known in the art (von Heijne, *J. Mol. Biol.* 184: 99–105, 1985). Prokaryotic and eukaryotic secretion signals that are functional in *E. coli* (or other host) may be employed. The presently preferred secretion signals include, but are not limited to pelB, matα, extensin and glycine-rich protein.

One skilled in the art appreciates that there are a wide variety of suitable vectors for expression in bacterial cells and which are readily obtainable. Vectors such as the pET series (Novagen, Madison, Wis.) and the tac and trc series (Pharmacia, Uppsala, Sweden) are suitable for expression of a β-glucuronidase. A suitable plasmid is ampicillin resistant, has a colEI origin of replication, a $lacI^q$ gene, a lac/trp hybrid promoter in front of the lac Shine-Dalgarno sequence, a hexa-his coding sequence that joins to the 3' end of the inserted gene, and an rrnB terminator sequence.

The choice of a bacterial host for the expression of a β-glucuronidase is dictated in part by the vector. Commercially available vectors are paired with suitable hosts. The vector is introduced in bacterial cells by standard methodology. Typically, bacterial cells are treated to allow uptake of DNA (for protocols, see generally, Ausubel et al., supra; Sambrook et al., supra). Alternatively, the vector may be introduced by electroporation, phage infection, or another suitable method.

Expression in Plant Cells

As noted above, the present invention provides vectors capable of expressing fungal secreted β-glucuronidase and secreted fungal β-glucuronidases. For agricultural applications, the vectors should be functional in plant cells. Suitable plants include, but are not limited to, wheat, rice, corn, soybeans, lupins, vegetables, potatoes, canola, nut trees, coffee, cassava, yam, alfalfa and other forage plants, cereals, legumes and the like. In one embodiment, rice is a host for gus gene expression.

Vectors that are functional in plants are preferably binary plasmids derived from *Agrobacterium* plasmids. Such vectors are capable of transforming plant cells. These vectors contain left and right border sequences that are required for integration into the host (plant) chromosome. At minimum, between these border sequences is the gene to be expressed under control of a promoter. In preferred embodiments, a selectable gene is also included. The vector also preferably contains a bacterial origin of replication for propagation in bacteria.

A gene for fungal β-glucuronidase should be in operative linkage with a promoter that is functional in a plant cell. Typically, the promoter is derived from a host plant gene, but promoters from other plant species and other organisms, such as insects, fingi, viruses, mammals, and the like, may also be suitable, and at times preferred. The promoter may be constitutive or inducible, or may be active in a certain tissue or tissues (tissue type-specific promoter), in a certain cell or cells (cell-type specific promoter), or at a particular stage or stages of development (development-type specific promoter). The choice of a promoter depends at least in part upon the application. Many promoters have been identified and isolated (e.g., CaMV 35S promoter, maize ubiquitin promoter) (see, generally, GenBank and EMBL databases). Other promoters may be isolated by well-known methods.

For example, a genomic clone for a particular gene can be isolated by probe hybridization. The coding region is mapped by restriction mapping, DNA sequence analysis, RNase probe protection, or other suitable method. The genomic region immediately upstream of the coding region comprises a promoter region and is isolated. Generally, the promoter region is located in the first 200 bases upstream, but may extend to 500 or more bases. The candidate region is inserted in a suitable vector in operative linkage with a reporter gene, such as in pBI121 in place of the CaMV 35S promoter, and the promoter is tested by assaying for the reporter gene after transformation into a plant cell. (see, generally, Ausubel et al., supra; Sambrook et al., supra; *Methods in Plant Molecular Biology and Biotechnology*, Ed. Glick and Thompson, CRC Press, 1993.)

Preferably, the vector contains a selectable marker for identifying transformants. The selectable marker preferably confers a growth advantage under appropriate conditions. Generally, selectable markers are drug resistance genes, such as neomycin phosphotransferase. Other drug resistance genes are known to those in the art and may be readily substituted. Selectable markers include ampicillin resistance, tetracycline resistance, kanamycin resistance, chloramphenicol resistance, and the like. The selectable marker also preferably has a linked constitutive or inducible promoter and a termination sequence, including a polyadenylation signal sequence. Other selection systems, such as positive selection can alternatively be used. Because the fungal gus genes of the present invention cleave Cba, they are particularly suitable for use as a positive selection marker.

The sequence of nucleotides encoding a β-glucuronidase may also include a classical secretion signal, whereby the resulting peptide is a precursor protein processed and secreted. Suitable signal sequences of plant genes include, but are not limited to the signal sequences from glycine-rich protein and extensin. In addition, a glucuronide permease gene to facilitate uptake of glucuronides may be co-transfected either from the same vector containing fungal GUS or from a separate expression vector.

A general vector suitable for use in the present invention is based on pCAMBIA 1305.2. Other vectors have been described (U.S. Pat. Nos. 4,536,475; 5,733,744; 4,940,838; 5,464,763; 5,501,967; 5,731,179) or may be constructed based on the guidelines presented herein. The plasmid contains a left and right border sequence for integration into a plant host chromosome and also contains a bacterial origin of replication and selectable marker. These border sequences flank two genes. One is a kanamycin resistance gene (neomycin phosphotransferase) driven by a nopaline synthase promoter and using a nopaline synthase polyadenylation site. The second is the *E. coli* gus gene (reporter gene) under control of the CaMV 35S promoter and polyadenlyated using a nopaline synthase polyadenylation site. The *E. coli* gus gene is replaced with a gene encoding a fungal gus gene, especially one that cleaves Cba. If appropriate, the CaMV 35S promoter is replaced by a different promoter. Either one of the expression units described above is additionally inserted or is inserted in place of the CaMV promoter and gus gene.

Plants may be transformed by any of several methods. For example, plasmid DNA may be introduced by *Agrobacterium* co-cultivation (e.g., U.S. Pat. Nos. 5,591,616; 4,940, 838) or bombardment (e.g., U.S. Pat. Nos. 4,945,050; 5,036, 006; 5,100,792; 5,371,015). Other transformation methods include electroporation (U.S. Pat. No. 5,629,183), CaPO$_4$-mediated transfection, gene transfer to protoplasts (AU B 600221), microinjection, and the like (see, *Gene Transfer to Plants*, Ed. Potrykus and Spangenberg, Springer, 1995, for procedures). Preferably, vector DNA is first transfected into *Agrobacterium* and subsequently introduced into plant cells. Most preferably, the infection is achieved by *Agrobacterium* co-cultivation. In part, the choice of transformation methods depends upon the plant to be transformed. Tissues can alternatively be efficiently infected by *Agrobacterium* utilizing a projectile or bombardment method. Projectile methods are generally used for transforming sunflowers and soybean. Bombardment is often used when naked DNA, typically *Agrobacterium* binary plasmids or pUC-based plasmids, is used for transformation or transient expression.

Briefly, co-cultivation is performed by first transforming *Agrobacterium* by freeze-thaw method (Holsters et al., *Mol. Gen. Genet.* 163: 181–187, 1978) or by other suitable methods (see, Ausubel, et al. supra; Sambrook et al., supra). Briefly, a culture of *Agrobacterium* containing the plasmid is incubated with leaf disks, protoplasts, meristematic tissue, or calli to generate transformed plants (Bevan, *Nucl. Acids. Res.* 12: 8711, 1984) (U.S. Pat. No. 5,591,616). After co-cultivation for about 2 days, bacteria are removed by washing and plant cells are transferred to plates containing antibiotic (e.g., cefotaxime) and a selective agent, such as Cba. Plant cells are further incubated for several days. The presence of the transgene may be tested for at this time. After further incubation for several weeks in selecting medium, calli or plant cells are transferred to regeneration medium and placed in the light. Shoots are transferred to rooting medium and then into glass house.

Briefly, for microprojectile bombardment, cotyledons are broken off to produce a clean fracture at the plane of the embryonic axis, which are placed broken surface up on medium with growth-regulating hormones, minerals and vitamin additives. Explants from other tissues or methods of preparation may alternatively be used. Explants are bombarded with gold or tungsten microprojectiles by a particle acceleration device and cultured for several days in a suspension of transformed *Agrobacterium*. Explants are transferred to medium lacking growth regulators but containing drug for selection and grown for 2–5 weeks. After 1–2 weeks more without drug selection, leaf samples from green, drug-resistant shoots are grafted to in vitro grown rootstock and transferred to soil. Classical tests for a transgene such as Southern blotting and hybridization or genetic segregation can also be performed.

A positive selection system, for example based on cellobiuronic acid in a culture medium lacking a carbon source is preferably used (see, U.S. Pat. No. 6,268,493.

Activity of secreted GUS is conveniently assayed in whole plants or in selected tissues using a glucuronide substrate that is readily detected upon cleavage. Glucuronide substrates that are colorimetric are preferred. Field testing of plants may be performed by spraying a plant with the glucuronide substrate and observing color formation of the cleaved product.

Expression in Other Organisms

A variety of other organisms are suitable for use in the present invention. For example, various fingi, including yeasts, molds, and mushrooms, insects, especially vectors for diseases and pathogens, and other animals, such as cows, mice, goats, birds, aquatic animals (e.g., shrimp, turtles, fish, lobster and other crustaceans), amphibians and reptiles and the like, may be transformed with a gus transgene.

The principles that guide vector construction for bacteria and plants, as discussed above, are applicable to vectors for these organisms. In general, vectors are well known and readily available. Briefly, the vector should have at least a promoter functional in the host in operative linkage with gus. Usually, the vector will also have one or more selectable markers, an origin of replication, a polyadenylation signal and a transcription terminator.

The sequence of nucleotides encoding a β-glucuronidase may also include a classical secretion signal, whereby the resulting peptide is a precursor protein processed and secreted. Suitable secretion signals may be obtained from a variety of genes, such as mat-alpha or invertase genes. In addition, a permease gene may be co-transfected.

One of ordinary skill in the art will appreciate that a variety of techniques for producing transgenic animals exist. In this regard, the following U.S. patents teach such methodologies and are thus incorporated herein by reference: U.S. Pat. Nos. 5,162,215; 5,545,808; 5,741,957; 4,873,191; 5,780,009; 4,736,866; 5,567,607; and 5,633,076.

Uses of Fungal β-glucuronidase

As noted above, fungal β-glucuronidase may be used in a variety of applications. In certain aspects, fungal β-glucuronidase can be used as a reporter/effector molecule and as a diagnostic tool. As taught herein, fungal P-glucuronidase that cleaves Cba is preferred as an in vivo reporter/effector molecule, whereas, in in vitro diagnostic applications, the biochemical characteristics of the p-glucuronidase disclosed herein (e.g., thermal stability, high turnover number) may provide preferred advantages.

Fungal GUS, either secreted or non-secreted, can be used as a marker/effector for transgenic constructions. In a certain embodiments, the transgenic host is a plant, such as rice, corn, wheat, or an aquatic animal. The transgenic GUS may be used in at least three ways: one in a method of positive selection, obviating the need for drug resistance selection, a second as a system to target molecules to specific cells, and a third as a means of detecting and tracking linked genes.

For positive selection, a host cell, (e.g., plant cells) is transformed with a gus transgene (preferably coding for a secretable GUS). Selection is achieved by providing the cells with a glucuronidated form of a required nutrient (U.S. Pat. Nos. 5,994,629; 5,767,378; PCT US99/17804). For example, all cells require a carbon source, such as glucose. In one embodiment, glucose is provided as glucuronyl glucose (cellobiuronic acid), which is cleaved by GUS into glucose plus glucuronic acid. The glucose would then bind to transporters and be taken up by cells. The aglycone part of the glucuronide can be any required compound, including without limitation, a cytokinin, auxin, vitamin, carbohydrate, nitrogen-containing compound, and the like. It will be appreciated that this positive selection method can be used for cells and tissues derived from diverse organisms, such as animal cells, insect cells, fungi, and the like. The choice of glucuronide will depend in part upon the requirements of the host cell.

As a marker/effector molecule, secreted GUS (s-GUS) is preferred because it is non-destructive, that is, the host does not need to be destroyed in order to assay enzyme activity. A non-destructive marker has special utility as a tool in plant breeding. The GUS enzyme can be used to detect and track linked endogenous or exogenously introduced genes. GUS may also be used to generate sentinel plants that serve as bioindicators of environmental status. Plant pathogen invasion can be monitored if GUS is under control of a pathogen promoter. In addition, such transgenic plants may serve as a model system for screening inhibitors of pathogen invasion. In this system, GUS is expressed if a pathogen invades. In the presence of an effective inhibitor, GUS activity will not be detectable. In certain embodiments, GUS is co-transfected with a gene encoding a glucuronide permease.

Transgenes for introduction into plants encode proteins that affect fertility, including male sterility, female fecundity, and apomixis; plant protection genes, including proteins that confer resistance to diseases, bacteria, fungus, nematodes, herbicides, viruses and insects; genes and proteins that affect developmental processes or confer new phenotypes, such as genes that control meristem development, timing of flowering, cell division or senescence (e.g., telomerase), toxicity (e.g., diphtheria toxin, saporin), affect membrane permeability (e.g., glucuronide permease (U.S. Pat. No. 5,432,081)), transcriptional activators or repressors, alter nutritional quality, produce vaccines, and the like.

Insect and disease resistance genes are well known. Some of these genes are present in the genome of plants and have been genetically identified. Others of these genes have been found in bacteria and are used to confer resistance. Particularly well known insect resistance genes are the crystal genes of *Staphylococcus thuringiensis*. The crystal genes are active against various insects, such as lepidopterans, *Diptera, Hemiptera* and *Coleoptera*. Many of these genes have been cloned. For examples, see, GenBank; U.S. Pat. Nos. 5,317,096; 5,254,799; 5,460,963; 5,308,760, 5,466, 597, 5,2187,091, 5,382,429, 5,164,180, 5,206,166, 5,407, 825, 4,918,066.

Other resistance genes to *Sclerotinia*, cyst nematodes, tobacco mosaic virus, flax and crown rust, rice blast, powdery mildew, verticillum wilt, potato beetle, aphids, as well as other infections, are useful within the context of this invention. Examples of such disease resistance genes may be isolated from teachings in the following references: isolation of rust disease resistance gene from flax plants (WO 95/29238); isolation of the gene encoding Rps2 protein from *Arabidopsis thaliana* that confers disease resistance to pathogens carrying the avrRpt2 avirulence gene (WO 95/28478); isolation of a gene encoding a lectin-like protein of kidney bean confers insect resistance (JP 71-32092); isolation of the Hm1 disease resistance gene to *C. carbonum* from maize (WO 95/07989); for examples of other resistance genes, see WO 95/05743; U.S. Pat. No. 5,496,732; U.S. Pat. No. 5,349,126; EP 616035; EP 392225; WO 94/18335; JP 43-20631; EP 502719; WO 90/11770; U.S. Pat. No. 5,270,200; U.S. Pat. Nos. 5,218,104 and 5,306, 863). Nucleotide sequences for other transgenes, such as controlling male fertility, are found in U.S. Pat. No. 5,478, 369, references therein, and Mariani et al., Nature 347: 737, 1990.

In similar fashion, fungal GUS, can be used to generate transgenic insects for tracking insect populations or facilitate the development of a bioassay for compounds that affect molecules critical for insect development (e.g., juvenile hormone). Secreted GUS may also serve as a marker for beneficial fungi destined for release into the environment. The non-destructive marker is useful for detecting persistence and competitive advantage of the released organisms.

In animal systems, secreted GUS may be used to achieve extracellular cleavage of glucuronides (e.g, pharmaceutical glucuronide) and examine conjugation patterns of glucuronides. Furthermore, as discussed above, secreted GUS may be used as a transgenic marker to track cells or as a positive selection system, or to assist in development of new bioactive GUS substrates that do not need to be transported across membrane. Aquatic animals are also suitable hosts for GUS transgene. GUS may be used in these animals as a marker or effector molecule.

Within the context of this invention, GUS may also be used in a system to target molecules to cells. This system is particularly useful when the molecules are hydrophobic and thus, not readily delivered. These molecules can be useful as effectors (e.g., inducers) of responsive promoters. For example, molecules such as ecdysone are hydrophobic and not readily transported through phloem in plants. When ecdysone is glucuronidated it becomes amphipathic and can be delivered to cells by way of phloem. Targeting of compounds such as ecdysone-glucuronic acid to cells is accomplished by causing cells to express receptor for ecdysone. As ecdysone receptor is naturally only expressed in insect cells, however a host cell that is transgenic for ecdysone receptor will express it. The glucuronide containing ecdysone then binds only to cells expressing the receptor. If these cells also express GUS, ecdysone will be released from the glucuronide and able to induce expression from an ecdysone-responsive promoter. Plasmids containing ecdysone receptor genes and ecdysone responsive promoter can be obtained from Invitrogen (Carlsbad, Calif.). Other ligand-receptors suitable for use in this system include glucocorticoids/glucocorticoid receptor, estrogen/estrogen receptor, antibody and antigen, and the like (see also U.S. Pat. Nos. 5,693,769 and 5,612,317).

In another aspect, purified fungal β-glucuronidase is used in medical applications. For these applications, secretion is not a necessary characteristic although it may be a desirable characteristic for production and purification. The biochemical attributes, such as the increased stability and enzymatic activity disclosed herein are preferred characteristics. The fungal glucuronidase preferably has one or more of the disclosed characteristics.

For the majority of drug or pharmaceutical analysis, the compounds in urine, blood, saliva, or other bodily fluids are de-glucuronidated prior to analysis. Such a procedure is undertaken because compounds are often, if not nearly always, detoxified by glucuronidation in vertebrates. Thus, drugs that are in circulation and have passed through a site of glucuronidation (e.g., liver) are found conjugated to glucuronic acid. Such glucuronides yield a complex pattern upon analysis by, for example, HPLC. However, after the aglycone (drug) is cleaved from the glucuronic acid, a spectrum can be compared to a reference spectrum. Currently, *E. coli* GUS is utilized in medical diagnostics, but as shown herein, fungal GUS may have superior qualities.

The fungal GUS enzymes disclosed herein may be used in traditional medical diagnostic assays, such as described above for drug testing, pharmacokinetic studies, bioavailability studies, diagnosis of diseases and syndromes, following progression of disease or its response to therapy and the like (see U.S. Pat. Nos. 5,854,009, 4,450,239, 4,274,832, 4,473,640, 5,726,031, 4,939,264, 4,115,064, 4,892,833). These β-glucuronidase enzymes may be used in place of other traditional enzymes (e.g., alkaline phosphatase, horseradish peroxidase, β-galactosidase, and the like) and compounds (e.g., green fluorescent protein, radionuclides) that serve as visualizing agents. Fungal GUS has qualities advantageous for use as a visualizing agent: it is highly specific for the substrate, water soluble and the substrates are stable. Thus, fungal GUS is suitable for use in Southern analysis of DNA, Northern analysis, ELISA, and the like.

In preferred embodiments, fungal GUS binds a hapten, either as a fusion protein with a partner protein that binds the hapten (e.g., avidin that binds biotin, antibody) or alone. If used alone, fungal GUS can be mutagenized and selected for hapten-binding abilities. Mutagenesis and binding assays are well known in the art. In addition, fungal GUS can be conjugated to avidin, streptavidin, antibody or another hapten-binding protein and used as a reporter in the myriad of assays that currently employ enzyme-linked binding proteins. Such assays include immunoassays, Western blots, in situ hybridizations, HPLC, high-throughput binding assays, and the like (see, for examples, U.S. Pat. Nos. 5,328,985 and 4,839,293, which teach avidin and streptavidin fusion proteins and U.S. Pat. No. 4,298,685, Diamandis and Christopoulos, *Clin. Chem.* 37: 625, 1991; Richards, *Methods Enzymol.* 184: 3, 1990; Wilchek and Bayer, *Methods Enzymol.* 184: 467, 1990; Wilchek and Bayer, *Methods Enzymol.* 184: 5, 1990; Wilchek and Bayer, *Methods Enzymol.* 184: 14, 1990; Dunn, *Methods Mol. Biol.* 32: 227, 1994; Bloch, *J. Hitochem. Cytochem.* 41: 1751, 1993; Bayer and Wilchek *J. Chromatogr.* 510: 3, 1990, which teach various applications of enzyme-linked technologies and methods).

Fungal GUSes can also be used in therapeutic methods. By turning compounds such as drugs into glucuronides, the compound is inactivated. When a glucuronidase is expressed or targeted to the site for delivery, the glucuronide is cleaved and the compound delivered. For these purposes, GUS may be expressed as a transgene or delivered, for example, coupled to an antibody specific for the target cell (see e.g., U.S. Pat. Nos. 5,075,340, 4,584,368, 4,481,195, 4,478,936, 5,760,008, 5,639,737, 4,588,686).

The present invention also provides kits comprising fungal GUS protein or expression vectors containing fungal gus gene. One exemplary type of kit is a dipstick test. Such tests are widely utilized for establishing pregnancy, as well as other conditions. Generally, these dipstick tests assay the glucuronide form, but it would be advantageous to use reagents that detect the aglycone form. Thus, GUS may be immobilized on the dipstick adjacent to or mixed in with the detector molecule (e.g., antibody). The dipstick is then dipped in the test fluid (e.g., urine) and as the compounds flow past GUS, they are cleaved into aglycone and glucuronic acid. The aglycone is then detected. Such a setup may be extremely useful for testing compounds that are not readily detectable as glucuronides.

In a variation of this method, the fungal GUS enzyme is engineered to bind a glucuronide, but lacks enzymatic activity. The enzyme will then bind the glucuronide and the enzyme is detected by standard methodology. Alternatively, GUS is fused to a second protein, either as a fusion protein or as a chemical conjugate that binds an aglycone. The fusion is incubated with the test substance and an indicator substrate is added. This procedure may be used for ELISA, Northern, Southern analysis and the like.

The following examples are offered by way of illustration, and not by way of limitation.

EXAMPLES

Example 1

Identification of Fungi Expressing β-Glucuronidase

In this example, fungi are screened for expression of β-glucuronidase by a colorimetric assay. Blue-staining fungi are selected, purified, and identified by comparison of rRNA sequences to known sequences.

Soil samples from around Canberra, Australia, are shaken for 15 sec in 500 µL of sterile water. After centrifugation at 17,000×g for 15 s, 100 µL of the supernatant are plated on modified M9 medium containing 4-O-(β-D-glucuronyl)-D-glucose (cellobiouronic acid; Cba) as the sole carbon source and 5-bromo-4-chloro-3-indolyl-β-D-glucuronide (X-GlcA) as an indicator substrate for β-glucuronidases (1.28% $Na_2HPO_4.7H_2O$, 0.3% $KH_2PO_4$, 0.05% NaCl, 0.1% $NH_4Cl$, 2 mM $MgSO_4$, 0.1 mM $CaCl_2$, 20 µg $L^{-1}$ folic acid, 20 µL-1 biotin, 50 µg $L^{-1}$ nicotinic acid, 50 µg $L^{-1}$ riboflavin, 50 µg $L^{-1}$ thiamin.Cl, 0.1 mg $L^{-1}$ pyridoxine.Cl, 2.8 mg $L^{-1}$ $H_3BO_3$, 1.8 mg $L^{-1}$ $MnCl_2.4H_2O$, 1.4 mg $L^{-1}$ $FeSO_4.7H_2O$, 30 µg $L^{-1}$ $CuCl_2.2H_2O$, 20 µg $L^{-1}$ $CoCl_2.6H_2O$, 3 mg $L^{-1}$ $Na_2$-EDTA, 10 mM Cba, 50 mg $L^{-1}$ X-GlcA, 1.5% agar). Cba is used to enrich for microorganisms with β-glucuronidase activity, because they should be able to hydrolyze Cba and thus grow on it as the sole carbon source. Such microorganisms are expected to stain blue as a result of hydrolyzing X-GlcA.

Blue-staining fungi are selected for further analysis. They are purified from any bacteria that may be adhering to fungi by consecutive sub-cultivations on YPD plates containing a combination of anti-bacterial antibiotics (1% yeast extract, 2% peptone, 2% glucose, 50 mg $L^{-1}$ ampicillin, 50 mg $L^{-1}$ streptomycin, 50 mg $L^{-1}$ nalidixic acid). After a minimum of six rounds of sub-cultivations, the isolates are transferred back on the original Cba medium to confirm their β-glucuronidase activity.

Purified isolates are grown in liquid YPD medium at 29° C. Genomic DNA is isolated from hyphae using the DNAzol kit (Invitrogen; Carlsbad, Calif., USA). A region between the 18S and 26S rRNA genes is amplified with primers ITS-fwd1 (SEQ ID NO:24) and ITS-rev4 (SEQ ID NO:25) (Table 1). This region contains the 5.8S rRNA gene flanked by intergenic transcribed spacers 1 and 2 (ITS1, ITS2), which are highly variable and well suited for identification of fungal isolates at the species level. In case no perfect match with a known species is found, a region of the 18S-rRNA gene is amplified using primers NS3 (SEQ ID NO:26) and NS6 (SEQ ID NO:27) for a tentative phylogenetic placement at the genus level (Table 1).

TABLE 1

Primers for amplification of fungal ITS regions and 18S rRNA gene fragments.

| Primer | No. bases | $T_m$ (° C.) | Sequence | SEQ ID NO: |
|---|---|---|---|---|
| ITS-fwd1 | 19 | 56 | 5'-TCCGTAGGTGAACCTGCGG-3' | 24 |
| ITS-rev4 | 20 | 50 | 5'-TCCTCCGCTTATTGATATGC-3' | 25 |
| NS3 | 21 | 62 | 5'-GCAAGTCTGGTGCCAGCAGCC-3' | 26 |
| NS6 | 24 | 57 | 5'-GCATCACAGACCTGTTATTGCCTC-3' | 27 |

The ITS region is amplified from 50 ng of genomic DNA with 0.5 U of REDTaq (Sigma; St. Louis, Mo., USA) in 20 μL of 10 mM Tris (pH 8.3), 50 mM KCl, 2.5 mM $MgCl_2$, 0.25 μM dNTPs, 1 μM ITS-fwd1, and 1 μM ITS-fwd4. After initial denaturation at 94° C. for 2 min, the reactions are cycled 35 times at 94° C. (20 sec), 50° C. (40 sec), and 72° C. (1.5 min), followed by a final extension at 72° C. for 5 min. The 18S rRNA gene fragment is amplified under identical conditions with NS3 and NS6 primers and an annealing temperature of 60° C. Amplified fragments are separated on a 1.2% TAE agarose gel, excised, and extracted using a gel nebulizer (Ultrafee-DA; Millipore; Bedford, Md., USA). Two microliters of each of the extracted amplified products are then sequenced using the BigDye Terminator sequencing mix (Perkin Elmer ABI, Poster City, Calif., USA). Cycling conditions for the sequence reactions are: 25 cycles of 96° C. (30 sec), 50° C. (15 sec), and 60° C. (4 min). After precipitation of the cycling products with 4 volumes of 75% isopropanol, they are separated on a polyacrylamide gel to obtain their nucleotide sequences.

TABLE 2

Sequences of rRNA genes

ITS1 - 5.8S rRNA gene - ITS2 - 28S rRNA gene       (SEQ ID NO: 28)
(partial) of *Penicillium canescens* isolate RPK
CGAGAATTCTCTGAATTCAACCTCCCACCCGTGTTTATTGTACCTTGTTGCTTCGGCGGGCCCGCCTCAC

GGCCGCCGGGGGGCATCTGCCCCCGGGCCCGCGCCCGCCGAAGACACCTTGAACTCTGTATGAAAATTGC

AGTCTGAGTCTAAATATAAATTATTTAAAACTTTCAACAACGGATCTCTTGGTTCCGGCATCGATGAAGA

ACGCAGCGAAATGCGATACGTAATGTGAATTGCAGAATTCAGTGAATCATCGAGTCTTTGAACGCACATT

GCGCCCCCTGGTATTCCGGGGGGCATGCCTGTCCGAGCGTCATTGCTGCCCTCAAGCCCGGCTTGTGTGT

TGGGTCTCGTCCCCCTTCCCGGGGGGACGGGCCCGAAAGGCAGCGGCGGCACCGCGTCCGGTCCTCGAGC

GTATGGGCTTTGTCACCCGCTCTGTAGGCCCGGCCGGCGCTTGCCGATCAACCAAAACTTTTTTCCAGG

TTGACCTCGGATCAGGTAGGGATACCCGCTGAACTTAA

TABLE 2-continued

Sequences of rRNA genes

ITS1 - 5.8S rRNA gene - ITS2 - 28S rRNA gene        (SEQ ID NO: 29)
(partial) of *Scopulariopsis* sp. isolate RP38.3
GGGATCATTACCGAAGTTACTCTTCAAAACCCATTGTGAACCTTACCTCTTGCCGCGCGTTGCCTCGGCG

GGGAGGCGGGGTCTGGGTCGGCGCGCCCCTCACCGGGCCGCCGTCCCGTCCCGTCCCCGCCGGCCGCGCC

AAACTCTAAATTTGAAAAAGCGTACTGCACGTTCTGATTCAAAACAAAAAACAAGTCAAAACTTTTAACA

ACGGATCTCTTGGTTCTGGCATCGATGAAGAACGCAGCGAAATGCGATAAGTAATGTGAATTGCAGAATT

CAGTGAATCATCGAATCTTTGAACGCACATTGCGCCCGGCAGCAATCTGCCGGGCATGCCTGTCCGAGCG

TCATTTCTTCCCTCGAGCGCGGCTAGCCCTACGGGGCCTGCCGTCGCCCGGTGTTGGGGCTCTACGGGTG

GGGCTCGTCCCCCCCGCAGTCCCCGAAATGTAGTGGCGGTCCAGCCGCGGCGCCCCCTGCGTAGTAGATC

CTACATCTCGCATCGGGTCCCGGCGAAGGCCAGCCGTCGAACCTTTTATTTCATGGTTTGACCTCGGATC

AGGTAGGGTTACCCGCT 18S rRNA gene (partial) of *Penicillium*            (SEQ ID NO: 30)
*canescens* isolate RPK
TTCCAGCTCCAATAGCGTATATTAAAGTTGTTGCAGTTAAAAAGCTCGTAGTTGAACCTTGGGTCTGGCT

GGCCGGTCCGCCTCACCGCGAGTACTGGTCCGGCTGGACCTTTCCTTCTGGGGAACCTCATGGCCTTCAC

TGGCTGTGGGGGAACCAGGACTTTTACTGTGAAAAAATTAGAGTGTTCAAAGCAGGCCTTTGCTCGAAT

ACATTAGCATGGAATAATAGAATAGGACGTGCGGTTCTATTTTGTTGGTTTCTAGGACCGCCGTAATGAT

TAATAGGGATAGTCGGGGGCGTCAGTATTCAGCTGTCAGAGGTGAAATTCTTGGATTTGCTGAAGACTAA

CTACTGCGAAAGCATTCGCCAAGGATGTTTTCATTAATCAGGGAACGAAAGTTAGGGGATCGAAGACGAT

CAGATACCGTCGTAGTCTTAACCATAAACTATGCCGACTAGGGATCGGACGGGATTCTATAATGACCCGT

TCGGCACCTTACGAGAAATCAAAGTTTTTGGGTTCTGGGGGAGTATGGTCGCAAGGCTGAAACTTAAAG

AAATTGACGGAAGGGCACCACAAGGCGTGGAGCCTGCGGCTTAATTTGACTCAACACGGGGAAACTCACC

AGGTCCAGACAAAATAAGGATTGACAGATTGAGAGCTCTTTCTTGATCTTTTGGATGGTGGTGCATGGCC

GTTCTTAGTTGGTGGAGTGATTTGTCTGCTTAATTGCGATAACGAACGAGACCTCGGCCCTTAAATAGCC

CGGTCCGCATTTGCGGGCCGCTGGCTTCTTAGGGGGACTATCGGCTCAAGCCGATGGAAGTGCAGG 18S rRNA gene (partial) of *Scopulariopsis*        (SEQ ID NO: 31)
sp. isolate RP38.3
AATTCCAGCTCCAATAGCGTATATTAAAGTTGTTGTGGTTAAAAAGCTCGTAGTCGAACCTTGGGCCTGG

CTGGCCGGTCCCCCTCACCGGGTGCACTGATCCAGCCGGGCCTTTCCCTCTGTGGAACCCCATGGCCTTC

ACTGGCTGTGCGGGGAAACAGGACTTTTACTGTGAAAAAATTAGAGTGCTCCAGGCAGGCCTATGCTCG

AATACATTAGCATGGAATAATAGAATAGGACGTGTGGTTCTATTTTGTTGGTTTCTAGGACCGCCGTAAT

GATTAATAGGGACAGTCGGGGGCATCAGTATTCAGTTGTCAGAGGTGAAATTCTTGGATCTACTGAAGAC

TAACTACTGCGAAAGCATTTGCCAAGGATGTTTTCATTGATAAGGAACGAAAGTTAGGGGATCGAAGACG

ATCAGATACCGTCGTAGTCTTAACTATAAACTATGCCGACTAGGGATCGGACGATGTTATTATTTGACGC

GTTCGGCACCTTTCGAGAAATCAAAGTGCTTGGGCTCCAGGGGAGTATGGTCGCAAGGCTGAAACTTAA

AGAAATTGACGGAAGGGCACCACCAGGGGTGGAACCTGCGGCTTAATTTGACTCAACACGGGGAAACTCA

CCAGGTCCAGACACAGTGAGGATTGACAGATTGAGAGCTCTTTCTTGATTCTGTGGGTGGTGGTGCATGG

CCGTTCTTAGTTGGTGGAGTGATTTGTCTGCTTAATTGCGATAACGAACGAGACCTTAACCTGCTAAATA

GCCCGTACTGCTCTGGCAGTTCGCCGGCTTCTTAGAGGGACTATCGGCTCAAGCCGAGGAAT

The ITS sequences (isolate RP38.3, (SEQ ID NO:28); isolate RPK (SEQ ID NO:2)) are then subjected to a similarity search, using the BLAST 2.0 server at NCBI (Altschul et al., *J Mol Biol* 215: 403–410, 1990). The sequences of the 18S rRNA genes (isolate RP 38.3, (SEQ ID NO:30); isolate RPK (SEQ ID NO:4)) are aligned against other eukaryotic 18S rRNA genes, using the facilities of the Ribosomal Database Project at Michigan State University (Maidak et al., *Nucleic Acids Res* 28: 173–174, 2000). The deduced phylogenetic placement of isolated fungi with β-glucuronidase activity is shown in Table 3.

TABLE 3

Phylogenetic placement of fungal and bacterial isolates with β-glucuronidase activity.

| Type of Isolate | ID | ITS1 - 5.8S rRNA gene - ITS2 - 28S rRNA gene (partial) | | SSU rRNA gene (partial) | |
|---|---|---|---|---|---|
| | | Closest match | Homology | Closest match | Homology |
| Fungus | RP38.3 | _[a] | — | *Scopulariopsis brevicaulis* (AY083220) | 99.8% (826/828) |
| Fungus | RPK | *Penicillium canescens* (AF033493) | 100% (528/528) | *Penicillium sacculum*[b] (AB027410) *Penicillium herquei* (AB086834) *Eladia saccula* (AB031391) *Eupenicillium* sp. (AY297772) | 99.9% (832/833) |

[a]No continuous match spanning both ITS and the 5.8S rRNA gene.
[b]The database does not contain the *Penicillium canescens* sequence.

Based on the results shown in Table 2, it is concluded that the two characterized GUS-expressing fungi belong to the Pezizomycotina (=Euascomycetes) subphylum of the *Ascomycota* phylum of the fungi kingdom. One of them (*Penicillium canescens*) is member of the Eurotiomycetes class, while the other (*Scopulariopsis breviaulis*) is member of the Sordariomycetes class. In addition, a second isolate of *Penicillium canescens*, DSM 1215, that expresses β-glucuronidase is identified by similar methods.

Example 2

Biochemical Confirmation of β-Glucuronidase Activity in Fungi

In this example, enzyme activity of β-glucuronidase in fungi is quantified following growth in media containing different inducers or no inducer of expression.

GUS-expressing fungi are isolated based on their ability to hydrolyze X-GlcA, a widely used GUS substrate. To confirm β-glucuronidase activity, the hydrolysis of 4-methylumbelliferyl-β-D-glucuronide (MU-GlcA), another widely used GUS substrate, is measured in vitro. Both purified fungal isolates are grown in liquid YPD medium on a shaker at 200 rpm/29° C. for 3 days. Hyphal aggregates are then vacuum-filtered, washed once with modified M9 medium lacking Cba (see Example 1), and suspended in the same medium. After 6 h of starvation in this medium, putative inducers of β-glucuronidase activity are added. These include X-GlcA (0.1 mM), Cba (20 mM) and glucuronic acid (GlcA; 0.1 and 20 mM). The fungi are then incubated in these media for an additional 6 h, in the course of which aliquots of hyphal aggregates are taken, vacuum-filtered and ground in liquid nitrogen.

Proteins are extracted in 40 mM PIPES pH 7.0, 2 mM di-thiothreitol, 1 mM ethylenediaminetetraacetic acid, 1 mM phenylmethylsulfonyl-fluoride, 0.1% [v/v] Triton X-100. Protein concentrations in the supernatants obtained by centrifugation at 23,000×g for 15 min/4° C. are determined with the Bradford assay, using bovine serum albumin dissolved in extraction buffer as a standard. The β-glucuronidase activity of these extracts is then measured in 160 µL of extraction buffer to which 0.1 mg mL$^{-1}$ BSA, 0.1% Triton X-100, 1 mM MU-GlcA and 3 µg mL$^{-1}$ of extracted proteins had been added. The reactions are incubated at 30° C. for increasing periods of time and stopped by addition of 40 µL of 2 M Na$_2$CO$_3$. The amount of 4-methylumelliferone (MU) released from MU-GlcA is quantified fluorimetrically with a SpectraFluor Plus microplate reader (excitation: 360 nm, emission: 465 nm; Tecan GmbH; Grodig, Austria), using MU dissolved in assay buffer as a standard.

FIG. 1 shows that GUS activity is only detectable if glucuronides such as X-GlcA and Cba, or free glucuronic acid, are added to the growth medium. After their addition, the GUS activity increases in a time-dependent manner. In the case where no inducer is added, the GUS activity remains below the detection limit. These data confirm that the isolated fungi express the enzyme GUS and hydrolyze glucuronides.

Example 3

Cloning of Fungal Gus Genes

Isolated genomic DNA from three fungal isolates is used as a template to amplify fragments of gus genes using degenerate primers. These primers are designed based on a multiple alignment of known gus genes from bacteria and animals. They are predicted to amplify a 1.2 kb-long fragment of an intron-less gene. The sequences of the primers are given in Table 4. PCR amplification is carried out in 20 µL of 10 mM Tris (pH 8.3), 50 mM KCl, 1.5 mM MgCl$_2$, 0.25 µM dNTPs, 11 M gus-fwd+T3, 1 µM gus-rev+T7, containing 0.5 U of REDTaq (Sigma; St. Louis, Mo., USA) and 50 ng of genomic DNA. Cycling conditions are 94° C. (2 min), followed by 35 cycles of 94° C. (20 sec), 48° C. (40 sec) and 72° C. (2 min 30 sec), and a final extension at 72° C. for 7 min.

TABLE 4

Degenerate primers used to amplify a 1.2 kb fragment of fungal gus genes.*

| Primer | No. of bases | Sequence |
| --- | --- | --- |
| gus - fwd + T3 | 39 | 5'-<u>AATTAACCCTCACTAAAGGG</u>AYTTYTWYAAYTAYGCIGG (SEQ ID NO: 32) |
| gus - rev + T7 | 39 | 5'-<u>GTAATACGACTCACTATAGGG</u>RAARTCIGCRAARAACCA (SEQ ID NO: 33) |

*T3 and T7 handles are underlined

A distinct 1.2 kb band is obtained from all three GUS-expressing fungal isolates, suggesting suggests that none of the gus fragments contains an intron. The bands are extracted from the gel and sequenced with T3 and T7 primers as described in Example 1. Hypothetical protein sequences, generated by translation of the obtained sequences in all three reading frames, are subjected to a similarity search as described in Example 1 to confirm that the amplified DNA fragments are derived from gus genes.

The complete nucleotide sequences of the three gus genes, part of their promoters, and the downstream regions are obtained by Semi-Random Two-Step PCR (Chun et al., Yeast 13: 233–240, 1997). The sequences are presented in FIGS. 2–4 (SEQ ID NOs:1, 3, and 5). In addition, limited upstream and downstream sequence was obtained. There is a small (20 bp) insertion in the downstream sequence of the DSM isolate compared to the RPK isolate. The remainder of those two sequences are about 90% identical.

Example 4

Sequence Analyses of Fungal Gus Genes and Their Products

FIGS. 2A–C (SEQ ID NO:1) and 3A–C (SEQ ID NO:3) display the nucleotide sequences of the genomic fragments isolated from two of the three fungal isolates with β-glucuronidase activity. Each fragment contains one continuous open reading frame (ORF). There are no ribosomal binding sites (GAGGA) situated 8 to 13 nucleotides upstream of the initiation codon of bacterial genes. Instead, several features of eukaryotic genes are present. In each case the predicted transcriptional start (see arrows in FIGS. 2 and 3), situated at an adenine nucleotide, is surrounded by pyrimidine nucleotides (one upstream and four to five downstream; FIGS. 2 and 3). This is a typical feature of eukaryotic genes (Knippers et al., Molekulare Genetik (5. Auflage). Georg Thieme Verlag, Stuttgart, Germany, 1990). TATA box-like motifs are located at −40 bp (*Scopulariopsis* sp.) or −32 bp and −19 bp (*Penicillium canescens*). In *Scopulariopsis* sp., the TATA box-like motif is surrounded by guanine nucleotides in positions characteristic for eukaryotic genes (Knippers et al., supra). A Kozak sequence-like motif (CCACC), known to enhance translation, is located immediately upstream of the initiation codon of the *Scopulariopsis* sp. gene (Kozak, Cell 44: 283–292, 1986). The 3' untranslated region of the gus genes contains putative polyadenylation signals and sites, which in the case of *Scopulariopsis* sp. exhibits a perfect match with the consensus sequences described in the literature (AATAAA with CA at +12 bp; Watson et al., Molecular Biology of the Gene (4th edition). The Benjamin/Cummings Publishing Company, Inc., Calif., USA 1987). In addition, the promoter region of gus in *Scopulariopsis* sp. contains three poly(dA) stretches characteristic for housekeeping genes in *Saccharomyces cerevisiae*, which is also a member of the *Ascomycota* phylum (Watson et al., supra).

The ORFs are translated into amino acid sequences (see FIG. 2, SEQ ID NO:2 and FIG. 3 SEQ ID NO:4). Analysis using a neural-network program (SignalP V1.1) trained to recognize eukaryotic N-terminal signal peptides, reveals that both fungal GUS proteins contain signal peptides; (Nielsen et al., Protein Engineering 12: 3–9, 1999). The predicted cleavage positions are between amino acids No. 26 and 27 (*Scopulariopsis* sp.) or 18 and 19 (*Penicillium canescens*). The presence of these N-terminal signal peptides suggests that both fungal isolates may produce secreted β-glucuronidases. This is consistent with the observation that both stain the surrounding agar blue.

The protein sequences are subjected to a similarity search, using the BLASTP program at the BLAST 2.0 server of NCBI (Altschul et al., J Mol Biol 215: 403–410, 1990). Results of these analyses demonstrate that the gene products are closely related to fungal and mammalian β-glucuronidases (e values range from $10^{-180}$ to $10^{-53}$). A conserved domain (CD) search at the same server identifies three CDs: pfam02837 (glycosyl hydrolases family 2; sugar-binding domain), pfam02836 (glycosyl hydrolases family 2; TIM barrel domain), and pfam00703 (glycosyl hydrolases family 2; immunoglobulin-like β-sandwich domain). In addition, both fungal GUS proteins contain the two signatures that, according to the Swiss Institute of Bioinformatics, characterize family 2 glycosyl hydrolases (see PDOC00531). This confirms that fungal GUS proteins, like GUS proteins from other organisms, are members of family 2 of glycosyl hydrolases.

Example 5

Identification of Additional Fungal Gus Genes Through Sequence Mining

To compare the amino acid sequences of the fungal GUS proteins with those of other β-glucuronidases, the sequences of other GUS proteins are retrieved from GenBank. In addition, using the TBLASTN program at the BLAST 2.0 server at NCBI, fungal genomes are mined for non-annotated gus genes and translated into proteins.

In addition, the amino acid sequence of GUS of isolate RPK (*Penicillium canescens*) is used as query sequence to search for additional fungal gus genes in the Whole-Genome-Shotgun Sequences (WGS) database at NCBI. A TBLASTN search, carried out on 12 Jul. 2003 (request ID 1057998419-03767-31842) identifies two more fungal genes in the genomes of *Aspergillus nidulans* and *Gibberella zeae* (anamorph: *Fusarium graminearum*). The gus gene of

*Aspergillus nidulans* is located between positions 285949 and 287784 (frame +1) in the sequence deposited under GenBank accession number AACD01000093.1. The gus gene of *Gibberella zeae* is located between positions 77805 and 76006 (frame −3) in the sequence deposited under GenBank accession number AACM01000315.1. The DNA sequences (*G. zeae* (SEQ ID NO:7); *A. nidulans* (SEQ ID NO:9)) and predicted amino acid sequences (*G. zeae* (SEQ ID NO:8); *A. nidulans* (SEQ ID NO:10)) are presented in FIGS. 5 and 6. Similar to the gus genes of *Penicillium canescens* and *Scopulariopsis*, there are no introns in these genes. Both of these fungi belong to the Pezizomycotina (=Euascomycetes) subphylum of the *Ascomycota phylum* of the fungi kingdom. One of them (*Aspergillus nidulans*) is member of the Eurotiomycetes class, while the other (*Gibberella zeae*) is member of the Sordariomycetes class.

The predicted amino acid sequences of these two additional gus genes are used as query sequences in a similarity search using the BLASTP program at the BLAST 2.0 server of NCBI (Altschul et al., *J Mol Biol* 215: 403–410, 1990). Results of these analyses demonstrate that their gene products are closely related to fungal and mammalian β-glucuronidases (e values range from $10^{-174}$ to $10^{-79}$). This search also identifies three CDs: pfam02837 (glycosyl hydrolases family 2; sugar-binding domain), pfam02836 (glycosyl hydrolases family 2; TIM barrel domain), and pfam00703 (glycosyl hydrolases family 2; immunoglobulin-like β-sandwich domain). Furthermore, both fungal GUS proteins contain the two signatures that, according to the Swiss Institute of Bioinformatics, characterize family 2 glycosyl hydrolases (see PDOC00531).

The sequences of all GUS proteins are aligned with AlignX sofware (InforMax, Bethesda, Md., USA), which is based on the ClustalW program (Thompson et al., *Nucleic Acids Res* 22: 4673–4680, 1994). BLOSUM 62 is chosen as the protein weight matrix (Henikoff and Henikoff, *Proc Natl Acad Sci USA* 89: 10915–10919, 1992). The gap-opening penalty is adjusted to 10, the gap-extension penalty to 0.05, and the gap-separation distance to 8. An end gap-separation penalty and residue-specific and hydrophilic gap penalties are included. The resulting multiple alignment is displayed in FIG. 7. This alignment shows considerable levels of sequence identity and similarity, particularly in the regions of the family 2 glycosyl hydrolase signatures. Two glutamate residues, at amino acids 562 and 607 as counted in the consensus sequence, which are previously shown to be required for catalytic activity of family 2 glycosyl hydrolases (Wong et al., *J Biol Chem* 273: 34057–34062, 1998; Islam et al., *J Biol Chem* 274: 23451–23455, 1999), are conserved in all GUS proteins, including the fungal forms (see asterisks in FIG. 7).

Figure 7G:
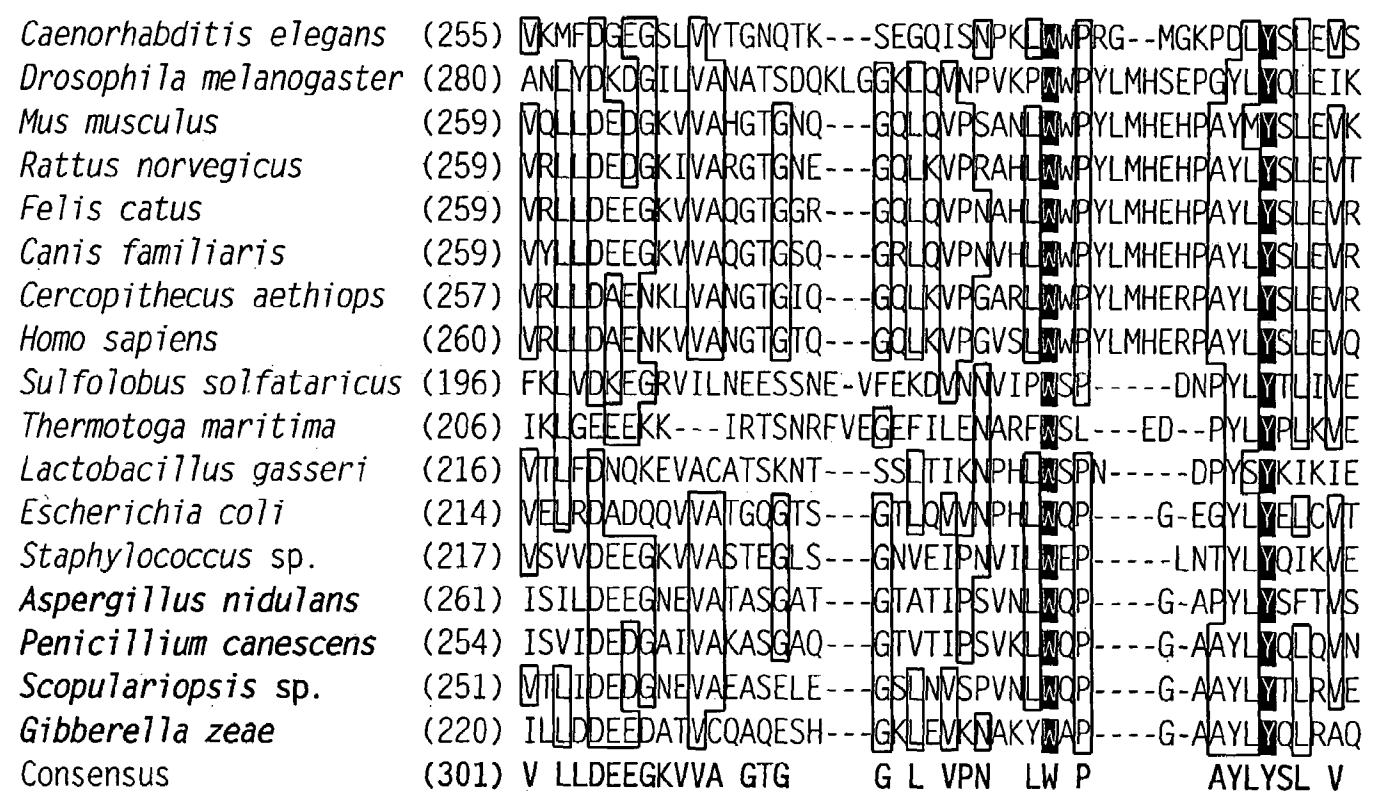
Figure 7K:
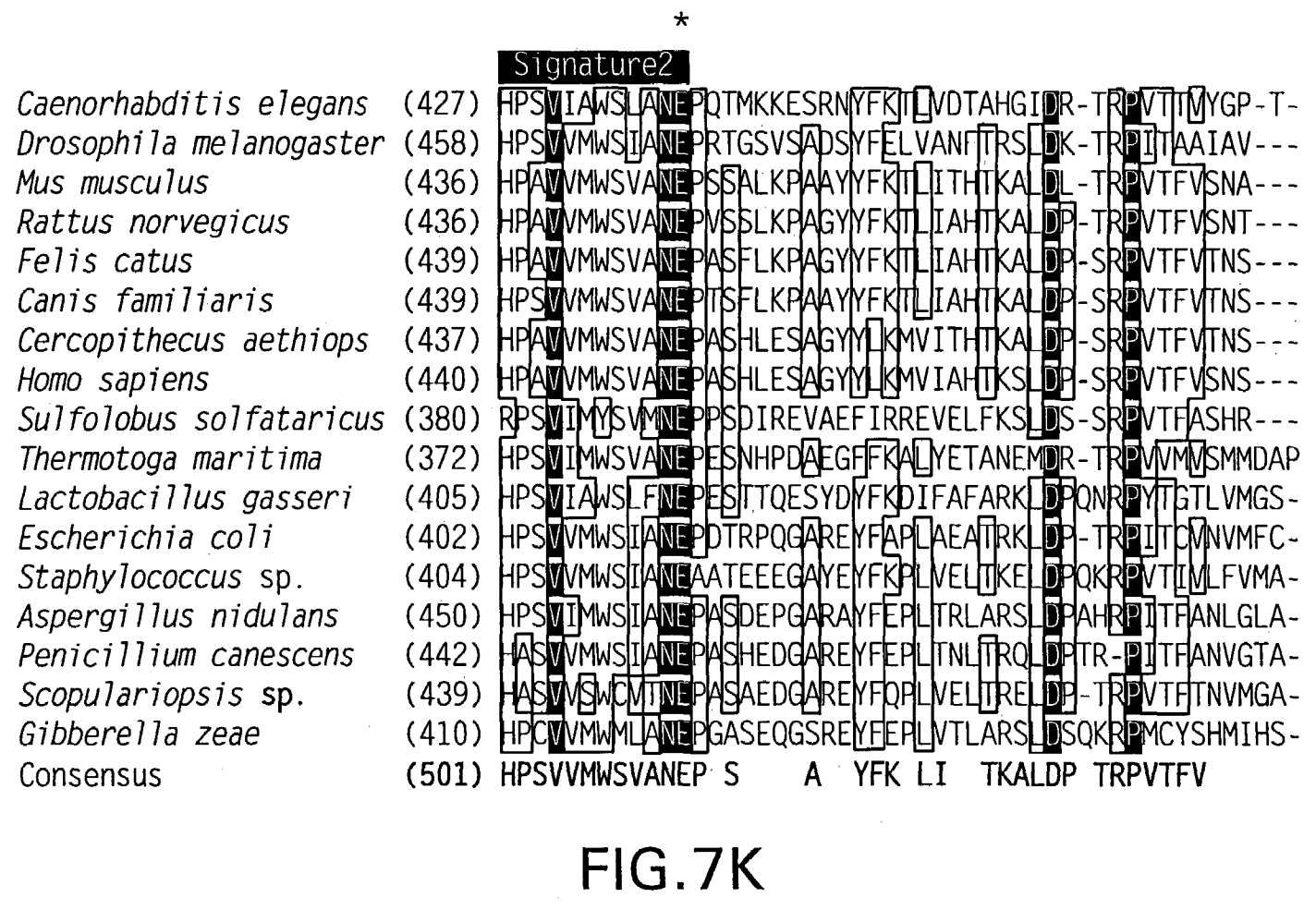
Figure 7N:
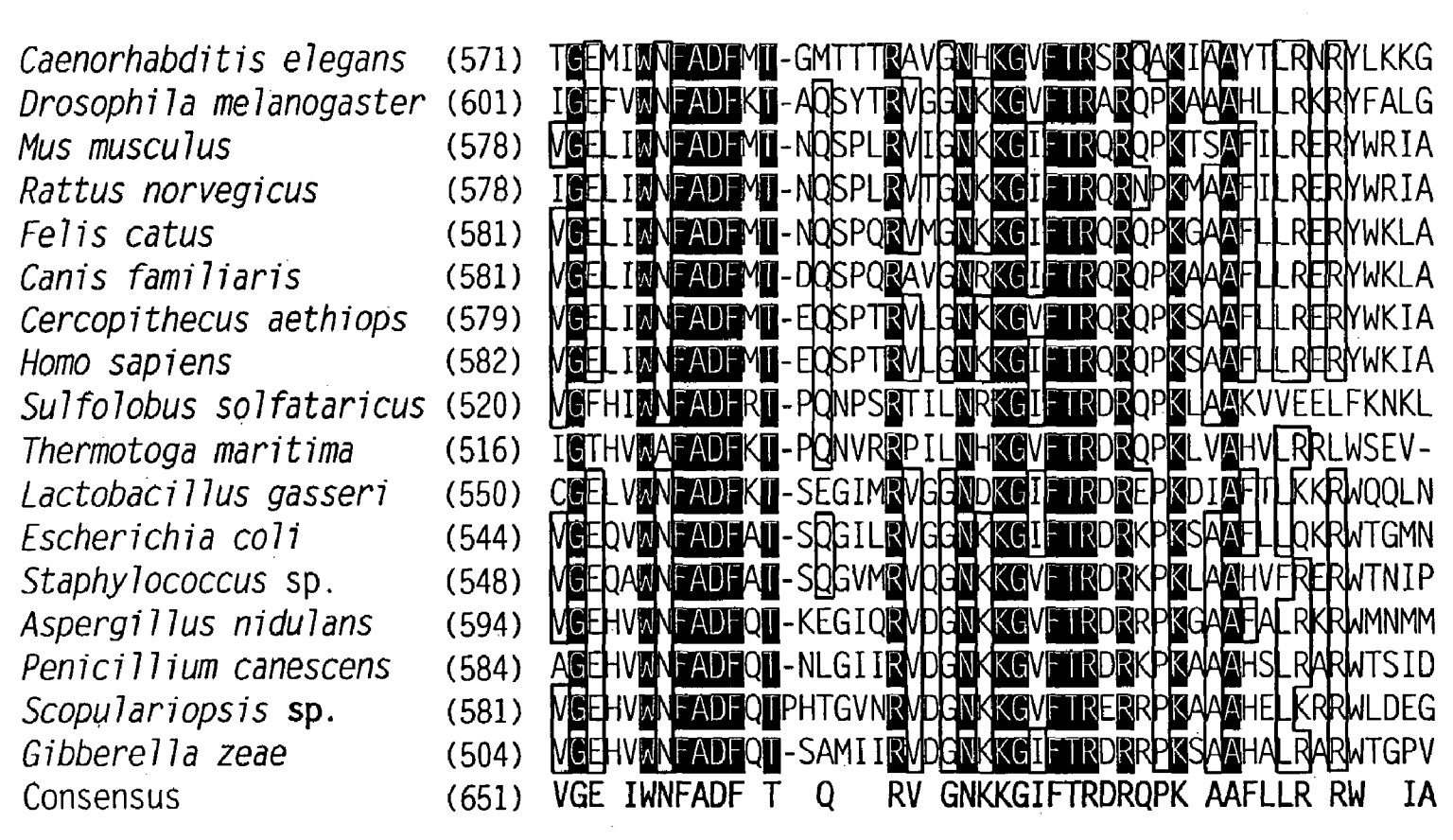

In pair-wise alignments, the overall identity (similarity) to $GUS^{Ecoli}$ is 49.6% (60.5%) for *Scopulariopsis* sp. and 50.3% (61.6%) for *Penicillium canescens*. The identities at the DNA level are 55.3% (*Scopulariopsis* sp.) and 50.8% (*Penicillium canescens*). The overall identity (similarity) to $GUS^{Ecoli}$ is 47.3% (59.1%) for *Aspergillus nidulans* and 50.4% (63.3%) for *Gibberella zeae*. Like the *Penicillium* and *Scopulariopsis* GUS proteins, the gene product from *Aspergillus nidulans* has an N-terminal signal peptide with a predicted cleavage position between amino acid No. 20 and 21 (Nielsen et al., *Protein Engineering* 12: 3–9, 1999). By contrast, the predicted gene product of *Gibberella zeae* does not appear to have an N-terminal signal peptide (FIG. 7).

Example 6

Expression of Fungal GUS Genes in *Escherichia coli* and Rice

To confirm that the isolated fungal gus genes indeed confer β-glucuronidase activity to organisms lacking it, the genes are cloned and transformed into a gus-deleted bacterium and a plant. The coding region of gus downstream of the predicted signal peptide cleavage site is amplified from genomic DNA of both *Penicillium canescens* and *Scopulariopsis* sp. Both pairs of forward and reverse primers contain restriction enzyme sites to facilitate subsequent cloning steps. Genomic DNA (5–50 ng) is used as a template in 20-μL amplification reactions containing 60 mM Tris $SO_4$ (pH 9.1), 18 mM $(NH_4)_2SO_4$, 1.8 mM $MgSO_4$, 0.2 mM dNTPs, 0.2 μM fwd and reverse primers (Table 4) and 1 U of ELONGase (Invitrogen; Carlsbad, Calif., USA). Cycling conditions are 94° C. (30 sec), followed by 30 cycles of 94° C. (20 sec) and 68° C. (4 min), and a final extension at 68° C. for 7 min. Amplified products are purified with the Qiagen PCR purification kit of (Qiagen GmbH; Hilden, Germany) and partially digested with SpeI and PmlI restriction enzymes. The digested fragments are separated on a TAE agarose gel (1.2%) and extracted from the gel using the Qiagen Gel Extraction Kit.

TABLE 5

| Primer | No. of bases | Sequence* |
|---|---|---|
| gus$^{Scop}$ − fwd + SpeI | 36 | 5'-CATAGC<u>ACTAGT</u>GCCGACACTGACCAATGGAAGACG-3' (SEQ ID NO: 34) |
| gus$^{Scop}$ − rev + PmlI | 35 | 5'-CGGTTA<u>CACGTG</u>AGCACCGGAAGTACCGTTCCCCA-3' (SEQ ID NO: 35) |
| gus$^{Pcan}$ − fwd + SpeI | 35 | 5'-CATAGC<u>ACTAGT</u>ACACCTGCAGCTCGGCACTTTCG-3' (SEQ ID NO: 36) |
| gus$^{Pcan}$ − rev + PmlI | 64 | 5'-CGGTTA<u>CACGTG</u>ATTCTTATCAATACTAGTCCACCTTGCCCTCAAA-3' (SEQ ID NO: 37) |

Figure 8:
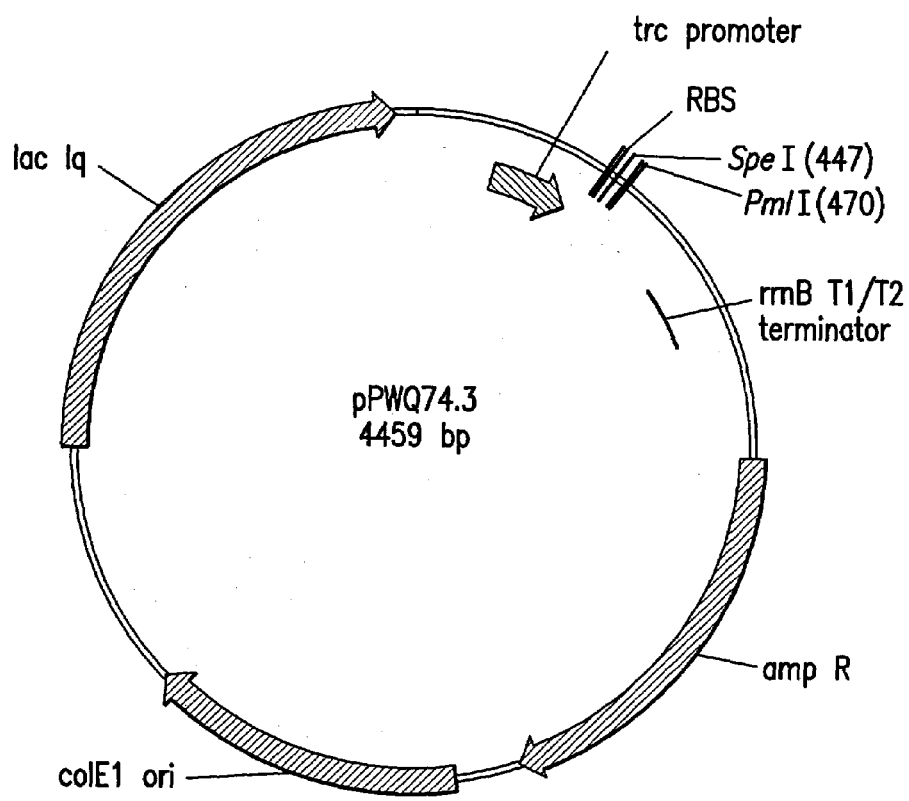
FIG. 8 is a schematic of pPWQ74.3, a vector backbone used to clone the gus genes of the present invention.

*Restriction enzyme sites are underlined.
gus$^{Scop}$ *Scopulariopsis* gus
gus$^{Pcan}$ *Penicillium* gus Aliquots are then ligated to a SpeI/PmlI-digested backbone (pPWQ74.3) using T4 DNA ligase. This vector is prepared from a bacterial expression vector, pTrcHis2-TOPO (Invitrogen, Carlsbad Calif.) by insertion of a fragment containing a ribosomal binding site followed by an initiation codon, a SpeI site, a PmlI site, and a stop codon (FIG. 8). Ligation products are transformed into the DH5α strain of Escherichia coli and selected on LB plates containing 100 mg $L^{-1}$ ampicillin. The nucleotide sequences of the obtained constructs are confirmed by sequencing. Constructs with the correct sequence (pPWR59.2 for Scopulariopsis sp.; pPWR59.4 for Penicillium canescens) are then transformed into an E. coli strain from which the entire gus operon has been deleted (JEMA99.9). Transformants are selected on LB plates supplemented with 100 mg $L^{-1}$ ampicillin, 40 mg $L^{-1}$ isopropyl-β-D-thiogalactoside and 50 mg $L^{-1}$ X-GlcA to induce expression of the cloned genes. A construct containing the gus gene of E. coli instead of a fungal gus gene (pPWR25.3) is used as positive control; the empty vector (pPWQ74.3) is used as negative control. As shown in Table 6, bacteria expressing either of the two fungal gus genes turn blue in the presence of the GUS substrate X-GlcA, while those containing the empty vector remain white.

TABLE 6

GUS activity of transgenic organisms without endogenous GUS activity that have been transformed with fungal gus genes

| | Host | |
|---|---|---|
| Source of gus gene | Escherichia coli | Leaves of rice plants |
| Scopulariopsis sp. | + | + |
| Penicillium canescens | + | + |
| Escherichia coli | + | n.d.* |
| Staphylococcus sp. | n.d.* | + |
| Empty vector | 0 | n.d.* |
| Untransformed organism | n.d.* | 0 |

GUS activity as visualized with X-GlcA added to the growth medium.
*Not determined.

Figure 9:
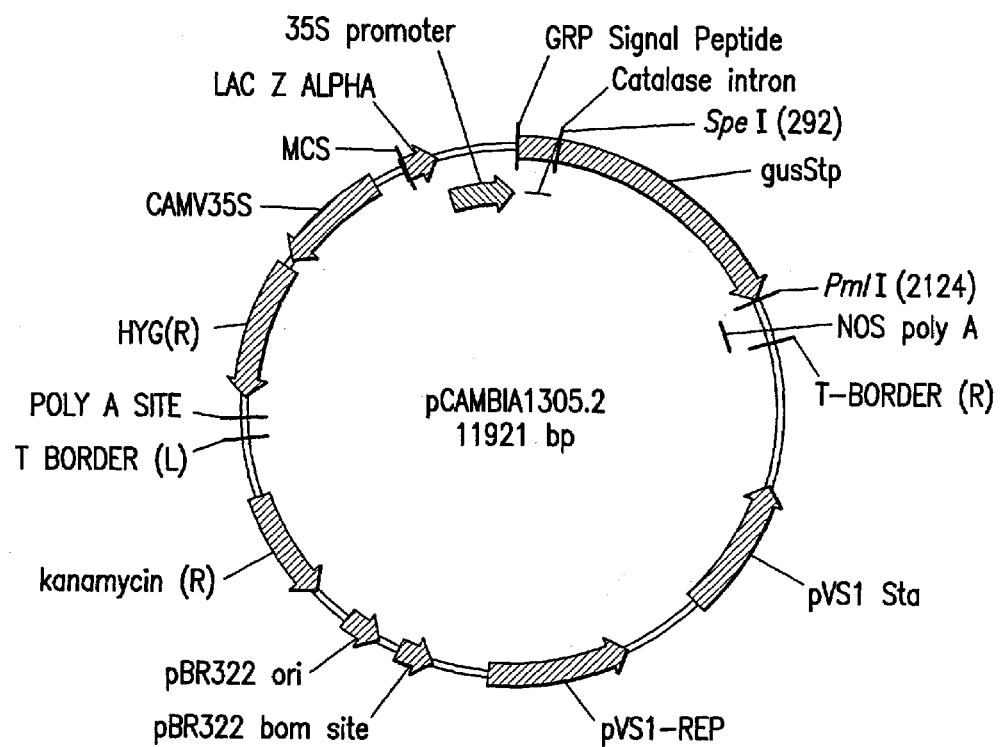
FIG. 9 is a schematic of the vector pCAMBIA1305.2, the backbone of which was used to clone the gus genes of the present.

For expression in plants, the two fungal gus genes are excised from the bacterial constructs by partial digestion with SpeI and PmlI restriction enzymes. Full-length gus fragments are purified on a 1.2% TAE agarose gel and extracted using the Qiagen Gel Extraction kit. Aliquots are then ligated to a plant expression vector from which the gus gene of a Staphylococcus species has been excised with SpeI and PmlI (pCAMBIA1305.2; FIG. 9). This fuses the fungal gus genes to an upstream sequence comprising the GRP (glycine-rich protein) signal peptide and the catalase intron. The former mediates secretion in plant cells and the latter boosts expression levels in plants. A stop codon is located immediately downstream of the cloning site. Plasmid DNA of bacterial colonies obtained after transformation into DH5α and selection on LB plates containing 100 $mg^{-1}$ ampicillin is sequenced to confirm the cloning step.

Constructs with the correct sequence (pKKWA68.4 for Scopulariopsis; pPWT9.17 for Penicillium canescens), as well as the original pCAMBIA1305.2 construct (positive control), are transformed into a strain of Agrobacterium tumefaciens (EHA105) by electroporation (Hood et al., Transgenic Res 2: 208–218, 1993; Sambrook supra). Transformants are selected on AB medium containing 50 µg $mL^{-1}$ kanamycin (Chilton et al., Proc. Natl. Acad. Sci. USA 71: 3672–3676, 1974). Scutellum-derived callus of rice (Oryza sativa L. cv. Nipponbare or Millin) is then transformed with both constructs using the protocol of Hiei et al. (Plant J 6: 271–282, 1994) and selecting for hygromycin-resistant plants.

Figure 10A:
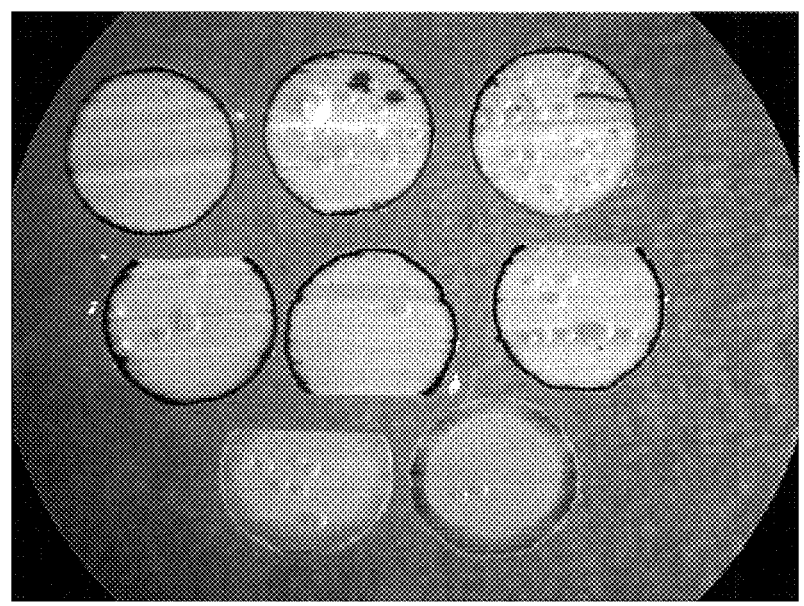
FIGS. 10A–B are pictographs of transgenic rice plants transformed with various constructs containing the gus genes of the present invention.
Figure 10B:
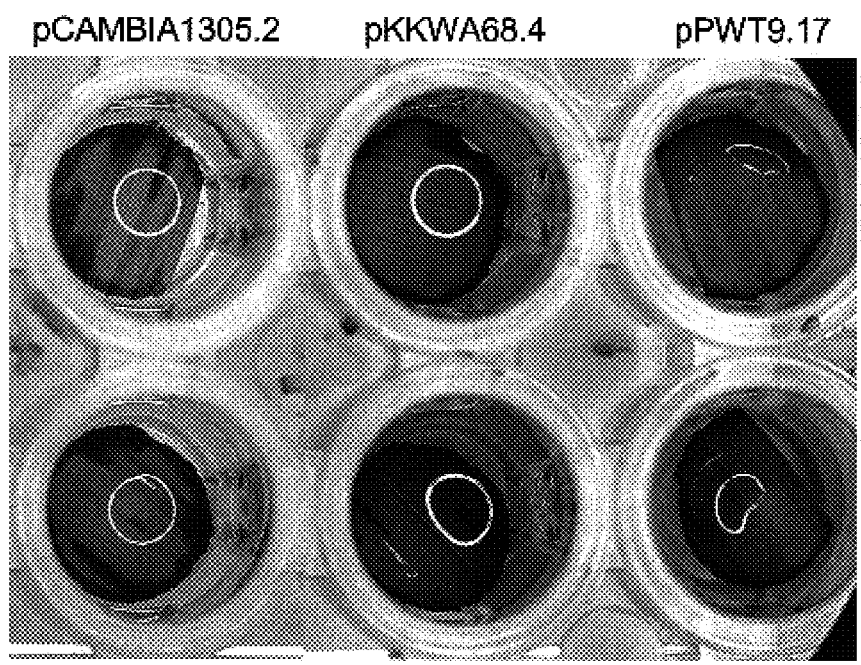

Leaves of T0 and T1 plants are excised and incubated in a 50 mM sodium phosphate buffer (pH 7.0) containing 1 mg $mL^{-1}$ X-GlcA for up to 16 hours at 37° C. (Jefferson, Plant Mol Biol Reporter 5: 387–405, 1987). GUS activity is visible in plants transformed with both fungal gus gens or the Staphylococcus gus gene in as little as 1 hour as indicated by the presence of a blue precipitate in leaf tissue (Table 5; FIG. 10A). No GUS activity (staining) is detected in leaves of untransformed plants. Leaf discs of plants transformed with pKKWA68.4 (gus from Scopulariopsis) and pPWT9.17 (gus from Penicillium canescens) stain the incubation medium significantly stronger than those of plants transformed with pCAMBIA1305.2 (gus from Staphylococcus) (FIG. 10B). This suggests that secretion of fungal β-glucuronidases in plants is particularly efficient in plants.

TABLE 7

Identification of SEQ ID NOs.

| | |
|---|---|
| SEQ ID NO: 1. | DNA sequence of the gus gene of Scopulariopsis sp. isolate RP38.3 |
| SEQ ID NO: 2. | Amino acid sequence of GUS protein from Scopulariopsis sp. isolate RP38.3 |
| SEQ ID NO: 3. | DNA sequence of the gus gene of Penicillium canescens isolate RPK |
| SEQ ID NO: 4. | Amino acid sequence of GUS protein from Penicillium canescens isolate RPK |
| SEQ ID NO: 5. | DNA sequence of the gus gene of Penicillium canescens isolate DSM1215 |
| SEQ ID NO: 6. | Amino acid sequence of GUS protein from Scopulariopsis sp. isolate DSM1215 |
| SEQ ID NO: 7. | DNA sequence of the gus gene of Gibberella zeae |
| SEQ ID NO: 8. | Amino acid sequence of GUS protein from Gibberella zeae |
| SEQ ID NO: 9. | DNA sequence of the gus gene of Aspergillus nidulans |
| SEQ ID NO: 10. | Amino acid sequence of GUS protein from Aspergillus nidulans |
| SEQ ID NO: 11. | Amino acid sequence of GUS protein from C. elegans |
| SEQ ID NO: 12. | Amino acid sequence of GUS protein from D. melanogaster |
| SEQ ID NO: 13. | Amino acid sequence of GUS protein from M. musculus |
| SEQ ID NO: 14. | Amino acid sequence of GUS protein from R. norvegicus |
| SEQ ID NO: 15. | Amino acid sequence of GUS protein from F. catus |
| SEQ ID NO: 16. | Amino acid sequence of GUS protein from C. familiaris |
| SEQ ID NO: 17. | Amino acid sequence of GUS protein from C. aethiops |
| SEQ ID NO: 18. | Amino acid sequence of GUS protein from H. sapiens |
| SEQ ID NO: 19. | Amino acid sequence of GUS protein from S. solfataricus |
| SEQ ID NO: 20. | Amino acid sequence of GUS protein from T. maritima |
| SEQ ID NO: 21. | Amino acid sequence of GUS protein from L. gasseri |

TABLE 7-continued

Identification of SEQ ID NOs.

| | |
|---|---|
| SEQ ID NO: 22. | Amino acid sequence of GUS protein from E. coli |
| SEQ ID NO: 23. | Amino acid sequence of GUS protein from Staphylococcus sp. |
| SEQ ID NO: 24. | Primer ITS-fwd1 |
| SEQ ID NO: 25. | Primer ITS-rev4 |
| SEQ ID NO: 26. | Primer NS3 |
| SEQ ID NO: 27. | Primer NS6 |
| SEQ ID NO: 28. | ITS sequence from isolate RP38.3 |
| SEQ ID NO: 29. | ITS sequence from isolate RPK |
| SEQ ID NO: 30. | 18S rRNA gene sequence from isolate RP38.3 |
| SEQ ID NO: 31. | 18S rRNA gene sequence from isolate RPK |
| SEQ ID NO: 32. | Primer gus-fwd + T3 |
| SEQ ID NO: 33. | Primer gus-rev + T7 |
| SEQ ID NO: 34. | Primer gus(Scop)-fwd + SpeI |
| SEQ ID NO: 35. | Primer gus(Scop)-rev + PmlI |
| SEQ ID NO: 36. | Primer gus(Pcan)-fwd + SpeI |
| SEQ ID NO: 37. | Primer gus(Pcan)-rev + PmlI |

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An isolated nucleic acid molecule comprising nucleotides 1–1905 of SEQ ID NO:3 or nucleotides 54–1905 of SEQ ID NO:3.

2. An isolated nucleic acid molecule that encodes SEQ ID No: 4 or encodes residues 19–634 of SEQ ID NO:4.

3. An expression vector, comprising a nucleic acid sequence encoding a fungal β-glucuronidase in operative linkage with a heterologous promoter, wherein the sequence encodes SEQ ID No: 4 or residues 19–634 of SEQ ID NO:4.

4. The expression vector of claim 3, wherein the fungal β-glucuronidase is encoded by nucleotides 1–1905 of SEQ ID NO:3 or nucleotides 54–1905 of SEQ ID NO:3.

5. The expression vector of claim 3, wherein the promoter is functional in a cell selected from the group consisting of a plant cell, a bacterial cell, an animal cell and a fungal cell.

6. The expression vector of claim 3, wherein the vector is a binary *Agrobacterium tumefaciens* plasmid vector.

7. The expression vector of claim 3, further comprising a nucleic acid sequence encoding a product of a gene of interest.

8. The expression vector of claim 7, wherein the product is a protein.

9. The expression vector of claim 3, wherein the fungal β-glucuronidase is an enzymatically active portion thereof.

10. A host cell containing the vector according to claim 3.

11. The host cell of claim 10, wherein the host cell is selected from the group consisting of a plant cell, an insect cell, a fungal cell, an animal cell and a bacterial cell.

12. A transgenic plant cell comprising the vector according to claim 3.

13. A transgenic plant comprising the plant cell of claim 12.

14. A method for monitoring expression of a gene of interest or a portion thereof in a host cell, comprising:
   (a) introducing into the host cell a vector construct, the vector construct comprising a nucleic acid molecule according to claim 1, and which encodes a functional β-glucuronidase and a nucleic acid molecule encoding a product of the gene of interest; wherein the β-glucuronidase and the gene of interest are co-expressed;
   (b) detecting the presence of the β-glucuronidase, thereby monitoring expression of the gene of interest.

15. A method for transforming a host cell with a gene of interest or portion thereof, comprising:
   (a) introducing into the host cell a vector construct, the vector construct comprising a nucleic acid molecule according to claim 1, and which encodes a functional β-glucuronidase, such that the vector construct integrates into the genome of the host cell; wherein the β-glucuronidase and the gene of interest a co-expressed;
   (b) detecting the presence of the β-glucuronidase, thereby establishing that the host cell is transformed.

16. A method for positive selection for a transformed cell, comprising:
   (a) introducing into a host cell a vector construct, the vector construct comprising a nucleic acid molecule according to claim 1, and which encodes a functional β-glucuronidase;
   (b) exposing the host cell to a sample comprising a glucuronide, wherein the glucuronide is cleaved by the β-glucuronidase, such that an aglycone is released, wherein the aglycone is advantageous for growth of the host cell; wherein a host cell that expresses the β-glucuronidase grows, thereby positively selecting a transformed cell.

17. The method of claim 16, further comprising introducing into the host cell a vector construct comprising a nucleic acid sequence encoding a fungal glucuronide transporter.

18. The method of claim 16, wherein the β-glucuronidase is fused to a nucleic acid molecule encoding a signal peptide.

19. The method of either of claim 16 or 18, wherein the host cell is selected from the group consisting of a plant cell, an animal cell, an insect cell, a fungal cell and a bacterial cell.

20. The method according to claim 16, wherein the aglycone is an auxin or a hormone.

21. The method according to claim 20, wherein the auxin is indole-3-ethanol.

22. The method according to claim 16, wherein the glucuronide is cellobiuronic acid.

23. A method of releasing a compound from a glucuronide exposed to a host cell, comprising:
   (a) introducing into the host cell a vector construct, the vector construct comprising a nucleic acid molecule encoding a β-glucuronidase; wherein the β-glucuronidase comprises SEQ ID NO: 4 or residues 19–634 of SEQ ID NO:4, and
   (b) exposing the host cell to the glucuronide, wherein the glucuronide is cleaved by the β-glucuronidase, such that the compound is released.

24. A method of monitoring activity of a regulatory sequence in a host cell comprising
   (a) introducing into the host cell a vector construct, the vector construct comprising nucleic acid sequence encoding a β-glucuronidase and a nucleic acid sequence of the regulatory sequence, wherein the nucleic acid sequence encoding the β-glucuronidase (i) encodes a protein comprising the amino sequence of SEQ ID No; 4, residues 19–634 of SEQ ID NO:4, or
   (ii) hybridizes under stringent conditions to the complement of nucleotides 1–1905 of SEQ ID NO:3, nucleotides 54–1905 of SEQ ID NO:3, and which encodes a functional β-glucuronidase, and wherein the nucleic acid sequence encoding the β-glucuronidase is in operative linkage with the regulatory sequence and
   (b) detecting the presence of the β-glucuronidase, thereby monitoring activity of the regulatory sequence.

25. The method according to claim 24, wherein the regulatory sequence is a promoter or an enhancer.

* * * * *